US012161382B2

(12) United States Patent
Pham et al.

(10) Patent No.: US 12,161,382 B2
(45) Date of Patent: Dec. 10, 2024

(54) FLOW MANIFOLD FOR CRYOABLATION CATHETER

(71) Applicant: Adagio Medical, Inc., Laguna Hills, CA (US)

(72) Inventors: Cuong Pham, Westminister, CA (US); Kevin D. Rupp, Irvine, CA (US); Alexei V. Babkin, Dana Point, CA (US); Pedram Nourian, Tustin, CA (US); Thu Tran, Garden Grove, CA (US); Steven W. Kovalcheck, San Diego, CA (US)

(73) Assignee: Adagio Medical, Inc., Laguna Hills, CA (US)

( * ) Notice: Subject to any disclaimer, the term of this patent is extended or adjusted under 35 U.S.C. 154(b) by 543 days.

(21) Appl. No.: 17/386,154

(22) Filed: Jul. 27, 2021

(65) Prior Publication Data

US 2022/0071680 A1 Mar. 10, 2022

Related U.S. Application Data

(60) Provisional application No. 63/065,892, filed on Aug. 14, 2020.

(51) Int. Cl.
*A61B 18/02* (2006.01)
*A61B 18/00* (2006.01)
(Continued)

(52) U.S. Cl.
CPC ......... *A61B 18/02* (2013.01); *A61M 25/0068* (2013.01); *A61M 25/0136* (2013.01); *A61M 25/0147* (2013.01); *A61B 2018/00083* (2013.01); *A61B 2018/00101* (2013.01); *A61B 2018/00363* (2013.01);
(Continued)

(58) Field of Classification Search
None
See application file for complete search history.

(56) References Cited

U.S. PATENT DOCUMENTS 5,108,390 A 4/1992 Potocky et al.
6,161,543 A 12/2000 Cox et al.
(Continued)

FOREIGN PATENT DOCUMENTS

EP 2311398 A1 4/2011
JP 2020518305 A 6/2020
(Continued)

OTHER PUBLICATIONS

Bunch TJ, Cutler MJ. Is pulmonary vein isolation still the cornerstone in atrial fibrillation ablation? J Thorac Dis. Feb. 2015;7(2):132-41.
(Continued)

*Primary Examiner* — Ronald Hupczey, Jr.
(74) *Attorney, Agent, or Firm* — Batt IP A Law Corporation; Richard Batt

(57) ABSTRACT

An ablation apparatus for creating a lesion in target tissue has a handle, an elongate shaft extending from the handle and a distal ablation portion. The distal ablation portion includes a cryogen flow manifold defining a plurality of fluid pathways between an insert body and a sleeve. Cryogen is circulated through the plurality of fluid pathways to create the lesion in the target tissue.

19 Claims, 34 Drawing Sheets

(51) Int. Cl.
  *A61M 25/00* (2006.01)
  *A61M 25/01* (2006.01)
(52) U.S. Cl.
  CPC .............. *A61B 2018/00577* (2013.01); *A61B 2018/00791* (2013.01); *A61B 2018/00839* (2013.01); *A61B 2018/0212* (2013.01); *A61B 2018/0262* (2013.01)

(56) References Cited

U.S. PATENT DOCUMENTS

| | | | |
|---|---|---|---|
| 6,190,382 B1 | 2/2001 | Ormsby et al. | |
| 6,270,493 B1 | 8/2001 | Lalonde et al. | |
| 6,551,309 B1* | 4/2003 | LePivert | A61B 18/02 606/23 |
| 6,941,953 B2 | 9/2005 | Feld et al. | |
| 7,083,612 B2 | 8/2006 | Littrup et al. | |
| 7,273,479 B2 | 9/2007 | Littrup et al. | |
| 7,410,484 B2 | 8/2008 | Littrup et al. | |
| 7,507,233 B2 | 3/2009 | Littrup et al. | |
| 7,921,657 B2 | 4/2011 | Littrup et al. | |
| 7,967,815 B1 | 6/2011 | Berzak et al. | |
| 8,177,780 B2 | 5/2012 | Cox et al. | |
| 8,387,402 B2 | 3/2013 | Littrup et al. | |
| 8,591,503 B2 | 11/2013 | Littrup et al. | |
| 8,740,891 B2 | 6/2014 | Babkin et al. | |
| 8,740,892 B2 | 6/2014 | Babkin et al. | |
| 9,408,656 B2 | 8/2016 | Littrup et al. | |
| 10,543,032 B2 | 1/2020 | Babkin | |
| 10,575,156 B2 | 2/2020 | Shedletsky et al. | |
| 10,617,459 B2 | 4/2020 | Yu et al. | |
| 2003/0040740 A1* | 2/2003 | Kovalcheck | A61B 18/02 606/21 |
| 2007/0149959 A1* | 6/2007 | DeLonzor | A61B 18/02 606/23 |
| 2013/0104993 A1 | 5/2013 | Groves et al. | |
| 2015/0018809 A1 | 1/2015 | Mihalik | |
| 2015/0196345 A1 | 7/2015 | Newell et al. | |
| 2016/0249859 A1 | 9/2016 | Babkin et al. | |
| 2016/0302841 A1 | 10/2016 | Williams et al. | |
| 2017/0049495 A1 | 2/2017 | Yu et al. | |
| 2019/0008572 A1 | 1/2019 | Lalonde et al. | |
| 2022/0000532 A1* | 1/2022 | Grimm | A61B 18/02 |

FOREIGN PATENT DOCUMENTS

| | | |
|---|---|---|
| WO | 2013013098 A1 | 1/2013 |
| WO | 2013013099 A1 | 1/2013 |
| WO | 2015160574 A1 | 10/2015 |
| WO | 2017048965 A1 | 3/2017 |
| WO | 2018142411 A1 | 8/2018 |
| WO | 2019140105 A1 | 7/2019 |
| WO | 2020028282 A1 | 2/2020 |

OTHER PUBLICATIONS

Callans DJ, Gerstenfeld EP, Dixit S, et al. Efficacy of repeat pulmonary vein isolation procedures in patients with recurrent atrial fibrillation. J Cardiovasc Electrophysiol 2004;15:1050-5.

International Search and Written Opinion for PCT/US21/43280 (Nov. 2, 2011).

Kim et al. Linear ablation in addition to circumferential pulmonary vein isolation (Dallas lesion set) does not improve clinical outcome in patients with paroxysmal atrial fibrillation: a prospective randomized study. Europace. Mar. 2015; 17 (3):388-95.

Kowalski M, Grimes MM, Perez FJ, et al. Histopathologic characterization of chronic radiofrequency ablation lesions for pulmonary vein isolation. J Am Coll Cardiol 2012;59:930-8.

Mcgann CJ, Kholmovski EG, Oakes RS, et al. New magnetic resonance imaging-based method for defining the extent of left atrial wall injury after the ablation of atrial fibrillation. J Am Coll Cardiol 2008;52:1263-71.

Ouyang F, Tilz R, Chun J, et al. Long-term results of catheter ablation in paroxysmal atrial fibrillation: lessons from a 5-year follow-up. Circulation 2010;122:2368-77.

Ranjan R, Kato R, Zviman MM, et al. Gaps in the ablation line as potential cause of recovery from electrical solation and their visualization using MRI. Circ Arrhythm Electrophysiol 2011;4:279-86.

Sawhney N, Anousheh R, Chen WC, et al. Five-year outcomes after segmental pulmonary vein isolation for paroxysmal atrial fibrillation. Am J Cardiol 2009;104:366-72.

Verma A, Kilicaslan F, Pisano E, et al. Response of atrial fibrillation to pulmonary vein antrum isolation is directly related to resumption and delay of pulmonary vein conduction. Circulation 2005;112:627-35.

Extended European Search Report of EP 21856427.6, dated Jul. 25, 2024.

* cited by examiner

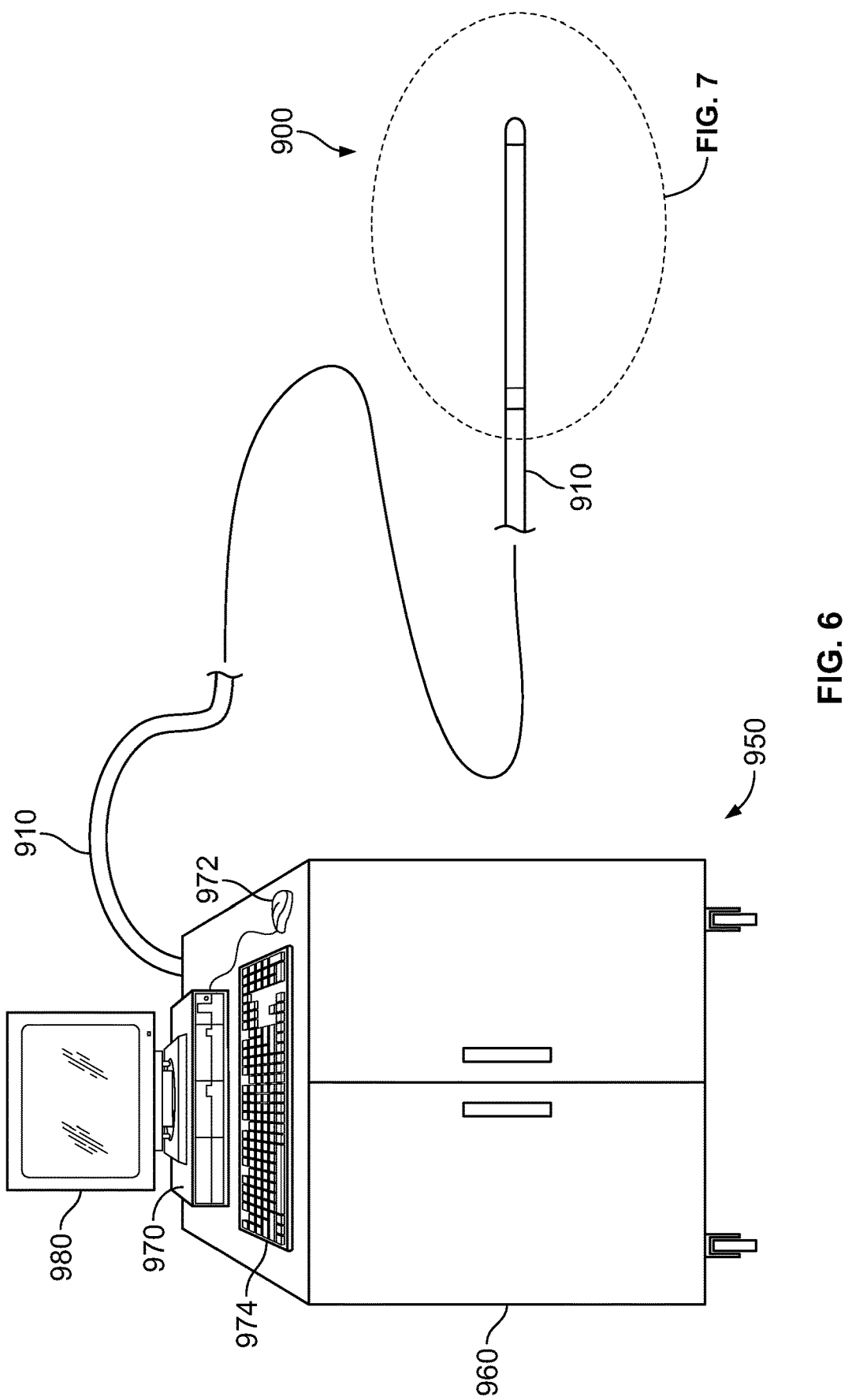

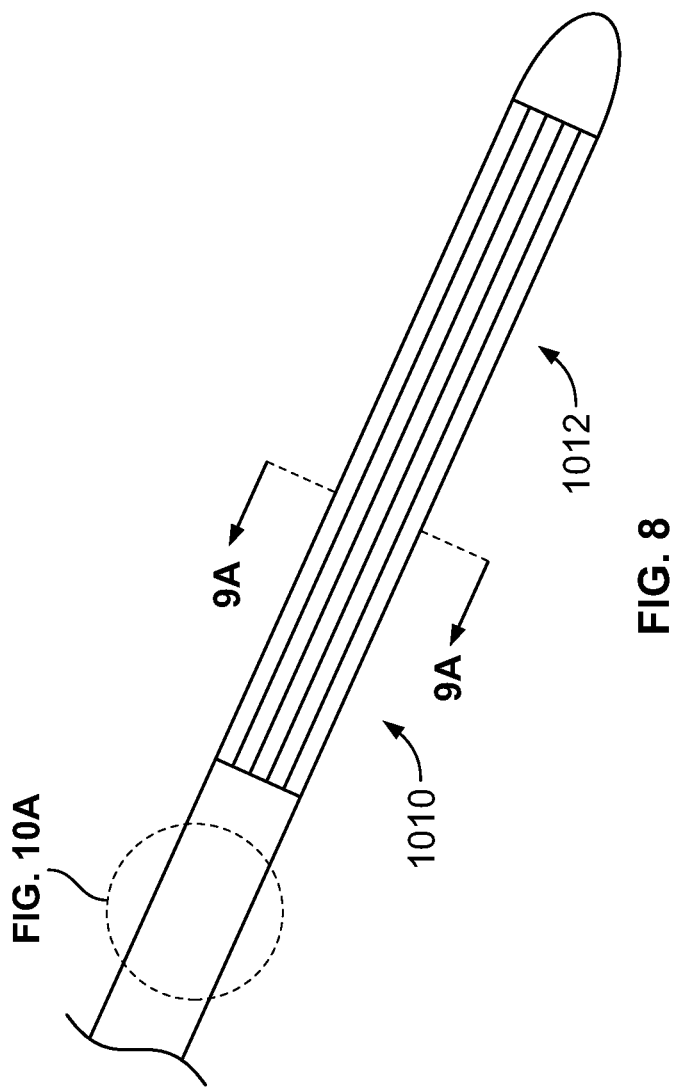

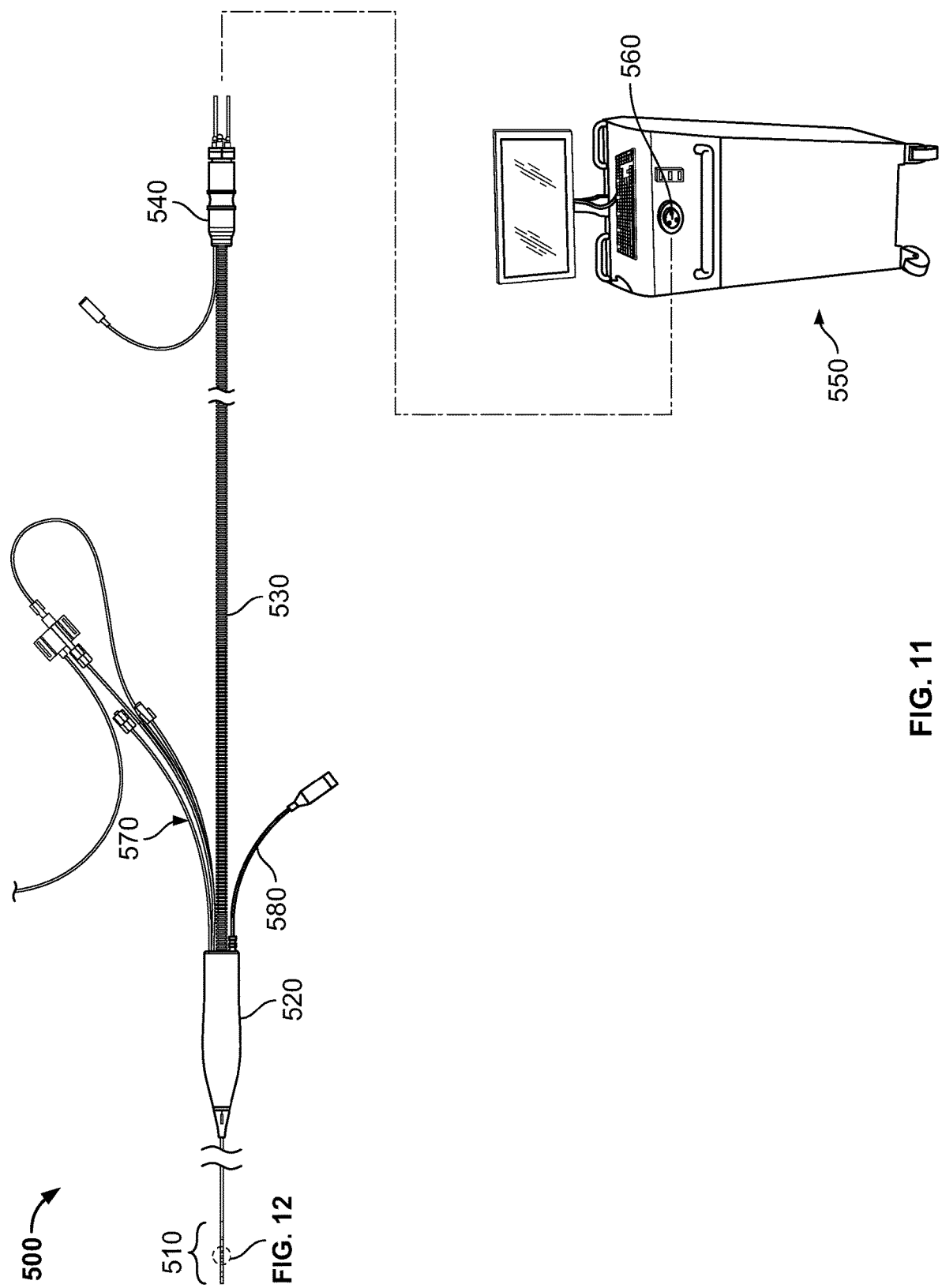

FLOW MANIFOLD FOR CRYOABLATION CATHETER

CROSS-REFERENCE TO RELATED APPLICATIONS

This application claims priority to U.S. provisional patent application No. 63/065,892, filed Aug. 14, 2020, and entitled "NOVEL FLOW MANIFOLD FOR CRYOABLATION CATHETER."

BACKGROUND

1. Field of the Invention

Embodiments of the invention relate to cryosurgery and more particularly to cryoablation systems and catheters for the treatment of heart disease.

2. Description of the Related Art

Atrial flutter and atrial fibrillation are heart conditions in which the left or right atrium of the heart beat improperly. Atrial flutter is a condition when the atria beat very quickly, but still evenly. Atrial fibrillation is a condition when the atria beat very quickly, but unevenly.

These conditions are often caused by aberrant electrical behavior of some portion of the atrial wall. Certain parts of the atria, or nearby structures such as the pulmonary veins, can misfire in their production or conduction of the electrical signals that control contraction of the heart, creating abnormal electrical signals that prompt the atria to contract between normal contractions caused by the normal cascade of electrical impulses. This can be caused by spots of ischemic tissue, referred to as ectopic foci, or by electrically active fibers in the pulmonary veins, for example.

Ventricular tachycardia (VT) is a type of regular and fast heart rate that arises from improper electrical activity in the ventricles of the heart. In ventricular tachycardia, the abnormal electrical signals in the ventricles cause the heart to beat faster than normal, usually 100 or more beats a minute, out of sync with the upper chambers. When this happens, the heart may not be able to pump enough blood to the body and lungs because the chambers are beating so fast or out of sync with each other that the chambers do not have time to fill properly. Thus, VT may result in cardiac arrest and may turn into ventricular fibrillation.

Premature ventricular contractions (PVCs) is another heart condition associated with the ventricles. PVCs are extra heartbeats that begin in one of the ventricles. These extra beats disrupt the regular heart rhythm, sometimes causing one to feel a fluttering or a skipped beat. PVCs, especially when another heart condition is present, can result in more severe cardiac events.

Of various heart conditions mentioned above, atrial fibrillation is one of the more prevalent types. Failing to treat atrial fibrillation can lead to a number of undesirable consequences including heart palpitations, shortness of breath, weakness and generally poor blood flow to the body.

Various techniques are practiced to treat atrial fibrillation. One technique to treat AF is pulmonary vein isolation (PVI). PVI is performed by creating lesions circumscribing the pulmonary veins. The PVI serves to block the errant or abnormal electrical signals.

A challenge in performing PVI, however, is to obtain a lasting or permanent isolation of the pulmonary veins. This shortcoming is highlighted in various studies. In one long-term follow-up study that investigated the rate of pulmonary vein reconnection after initial isolation, 53% of 161 patients were free of AF. In 66 patients, a repeat ablation was performed for repeat arrhythmia. The rate of pulmonary vein reconnection was high at 94% (62 of 66 patients). (Ouyang F, Tilz R, Chun J, et al. Long-term results of catheter ablation in paroxysmal atrial fibrillation: lessons from a 5-year follow-up. Circulation 2010; 122:2368-77.)

One reason that some PVI treatments are not durable is because of the phenomena of pulmonary vein (or electrical) reconnection. (Sawhney N, Anousheh R, Chen W C, et al. Five-year outcomes after segmental pulmonary vein isolation for paroxysmal atrial fibrillation. Am J Cardiol 2009; 104:366-72) (Callans D J, Gerstenfeld E P, Dixit S, et al. Efficacy of repeat pulmonary vein isolation procedures in patients with recurrent atrial fibrillation. J Cardiovasc Electrophysiol 2004; 15:1050-5) (Verma A, Kilicaslan F, Pisano E, et al. Response of atrial fibrillation to pulmonary vein antrum isolation is directly related to resumption and delay of pulmonary vein conduction. Circulation 2005;112:627-35)

Pulmonary vein reconnection may be attributed to gaps and incomplete or discontinuous isolation of the veins. (Bunch T J, Cutler M J. Is pulmonary vein isolation still the cornerstone in atrial fibrillation ablation? J Thorac Dis. 2015 February; 7(2):132-41). Incomplete isolation is a result of residual gap(s) within the encircling lesion or lack of transmural lesions. (McGann C J, Kholmovski E G, Oakes R S, et al. New magnetic resonance imaging-based method for defining the extent of left atrial wall injury after the ablation of atrial fibrillation. J Am Coll Cardiol 2008; 52:1263-71.) (Ranjan R, Kato R, Zviman M M, et al. Gaps in the ablation line as a potential cause of recovery from electrical isolation and their visualization using MRI. Circ Arrhythm Electrophysiol 2011; 4:279-86.)

Additionally, early recurrence of AF post ablation may be an early marker of incomplete pulmonary vein isolation. This is supported by a study of 12 patients that underwent a maze procedure after a failed radiofrequency ablation. Notably, myocardial biopsies showed anatomic gaps and/or non-transmural lesions in pulmonary veins that had reconnected. (Kowalski M, Grimes M M, Perez F J, et al. Histopathologic characterization of chronic radiofrequency ablation lesions for pulmonary vein isolation. J Am Coll Cardiol 2012; 59:930-8.)

This is further supported in a canine study in which endocardial conduction block was demonstrated and post procedural gaps were identified using MRI within the line of ablation. Long-term follow up data demonstrated that those pulmonary veins with the MRI-identified gaps were more likely to become electrically reconnected with symptomatic recurrences. (Ranjan R, Kato R, Zviman M M, et al. Gaps in the ablation line as potential cause of recovery from electrical isolation and their visualization using MRI. Circ Arrhythm Electrophysiol 2011; 4:279-86.)

Various attempts to solve the above referenced problem include making linear ablations in combination with circumferential pulmonary vein isolation (CPVI). One study, for example, compared clinical outcomes of CPVI with additional linear ablations and CPVI in a prospective randomized controlled study among patients with paroxysmal AF. The study enrolled 100 paroxysmal AF patients (male 75.0%, 56.4 f 11.6 years old) who underwent radio frequency circumferential ablation (RFCA) and were randomly assigned to the CPVI group (n=50) or the catheter Dallas lesion group (CPVI, posterior box lesion, and anterior linear ablation, n=50). The catheter Dallas lesion group required longer procedure (190.3±46.3 vs. 161.1±30.3 min, P<0.001) and ablation times (5345.4±1676.4 vs. 4027.2±878.0 s, P<0.001) than the CPVI group. Complete bidirectional conduction block rate was 68.0% in the catheter Dallas lesion group and 100% in the CPVI group. Procedure-related complication rates were not significantly different between the catheter Dallas lesion (0%) and CPVI groups (4%, P=0.157). During the 16.3±4.0 months of follow-up, the clinical recurrence rates were not significantly different between the two groups, regardless of complete bidirectional conduction block achievement after linear ablation. (Kim et al. Linear ablation in addition to circumferential pulmonary vein isolation (Dallas lesion set) does not improve clinical outcome in patients with paroxysmal atrial fibrillation: a prospective randomized study. Europace. 2015 March; 17(3):388-95.)

Thus, in view of the above referenced study, adding more ablation points around the vein entries, and/or attempting to add a linear lesion by using point by point ablation, does not appear to be an optimal solution to prevent gap(s) along the encircling lesion. Additionally, adding multiple points and lines undesirably increases the procedure time.

In view of the above shortcomings, various ablation catheters have been proposed for creation of the lesion, including flexible cryoprobes or cryocatheters, bipolar RF catheters, monopolar RF catheters (using ground patches on the patient's skin), microwave catheters, laser catheters, and ultrasound catheters. U.S. Pat. No. 6,190,382 to Ormsby and U.S. Pat. No. 6,941,953 to Feld, for example, describe RF ablation catheters for ablating heart tissue. These approaches are attractive because they are minimally invasive and can be performed on a beating heart. However, these approaches have a low success rate. The low success rate may be due to incomplete lesion formation. A fully transmural lesion is required to ensure that the electrical impulse causing atrial fibrillation are completely isolated from the remainder of the atrium, and this is difficult to achieve with beating heart procedures.

Thus, the challenge for the surgeon is to place the catheter/probe along the correct tissue contour such that the probe makes complete contact with the tissue. Due to the nature of the procedure and the anatomical locations where the lesions must be created, the catheter must be sufficiently flexible and adjustable such that they can match the shape and contour of the tissue to be ablated.

Malleable and flexible cryoprobes are described in U.S. Pat. Nos. 6,161,543 and 8,177,780, both to Cox, et al. The described probes have a malleable shaft. In embodiments, a malleable metal rod is coextruded with a polymer to form the shaft. The malleable rod permits the user to plastically deform the shaft into a desired shape so that a tip can reach the tissue to be ablated.

U.S. Pat. No. 5,108,390, issued to Potocky et al, discloses a highly flexible cryoprobe that can be passed through a blood vessel and into the heart without external guidance other than the blood vessel itself.

A challenge with some of the above apparatuses, however, is making continuous contact along the anatomical surface such that a continuous lesion may be created. This challenge is amplified not only because of the varying contours and shapes of the target tissue because of the location in the body but also because of variations in anatomy between patients. Thus, different treatment procedures and patient anatomy require different catheters to be designed and used. Another challenge is to be able to adjust the shape of the catheter in situ to address these variations in anatomy, etc.

Additional challenges with some of the above apparatuses is with efficient thermal conductivity, i.e., cooling/heat transfer, between the internal cooling/heating elements of the devices and the exterior jackets/sleeves of the devices. Thus, freezing and heating temperatures may need be efficiently transferred to the tissue to be ablated.

Accordingly, there is a need for improved methods and systems for providing minimally invasive, adjustably shaped, safe and efficient cryogenic cooling of tissues. These improved systems include improved apparatuses and methods to form continuous lesions in target tissue regardless of the condition being treated and variations in patient anatomy.

There is also a need for an improved apparatus and method to treat AF, atrial flutter and VT and to achieve more complete, durable, and safe electrical signal isolation within the various chambers of the heart, including pulmonary vein isolation.

SUMMARY

An embodiment of the invention is an ablation apparatus for creating a lesion in target tissue having a handle, a flexible elongate shaft extending from the handle and a distal ablation portion. The distal ablation portion includes a cryogen flow manifold defining a plurality of fluid pathways between an insert body and a tubular sleeve. Cryogen is circulated through the plurality of fluid pathways to create the lesion in the target tissue.

In embodiments, the insert body has a polygon shaped cross section such that the plurality of fluid pathways are defined between the sides of the insert body and the inner lumen of the sleeve. Optionally, the sides of the insert body may vary along its circumference such that flat sides are separated by a bowed or curved side, corresponding to fluid pathways of relatively high and low cryogen flow rates respectively. Without intending to being bound to theory, the varying geometry and fluid pathways serve to increase turbulent flow, increasing cooling power efficiency.

In embodiments, the handle includes an actuator assembly to bend the catheter shaft through a range of angles from 0 to 180 or more based on a corresponding amount the actuator member is manipulated by the physician.

In embodiments, the handle includes a frictional brake assembly which the physician activates to lock or set the catheter bend at a desired angle. The brake is releasable, after which the shaft angle may be adjusted as desired.

In embodiments, a method includes advancing the distal ablation portion of the catheter into a ventricle of the heart, bending the shaft to a target angle in the range of 120 to 180 degrees, locking the shaft at the target angle; placing the distal ablation portion against the target tissue, and circulating a cryogen through a plurality of fluid pathways in a flow manifold of the distal ablation portion to create a lesion in the target tissue.

In embodiments, a method for treating ventricular tachycardia by creating a lesion comprises: advancing a distal ablation portion of a catheter into a ventricle of the heart; placing the distal ablation portion against a target tissue selected from the RV septum, LV septum, LV lateral wall, and the LV apex, and creating a plurality of discrete turbulent cryogen flowpaths extending lengthwise and arranged about the circumference of the distal ablation portion to create the lesion in the target tissue.

The description, objects and advantages of embodiments of the present invention will become apparent from the detailed description to follow, together with the accompanying drawings.

BRIEF DESCRIPTION OF THE DRAWINGS

The above-mentioned aspects, as well as other features, aspects and advantages of the present technology will now be described in connection with various embodiments, with reference to the accompanying drawings. The illustrated embodiments, however, are merely examples and are not intended to be limiting. Throughout the drawings, similar symbols typically identify similar components, unless context dictates otherwise. Note that the relative dimensions of the following figures may not be drawn to scale.

FIG. 6 is an illustration of a cryoablation system including a cryoablation catheter, according to an embodiment of the invention;

FIG. 8 is a perspective view of another embodiment of a cryoablation catheter having a flexible distal treatment section;

FIG. 11 is a perspective view of another embodiment of a cryoablation catheter having a flexible distal treatment section;

DETAILED DESCRIPTION

Figure 1:
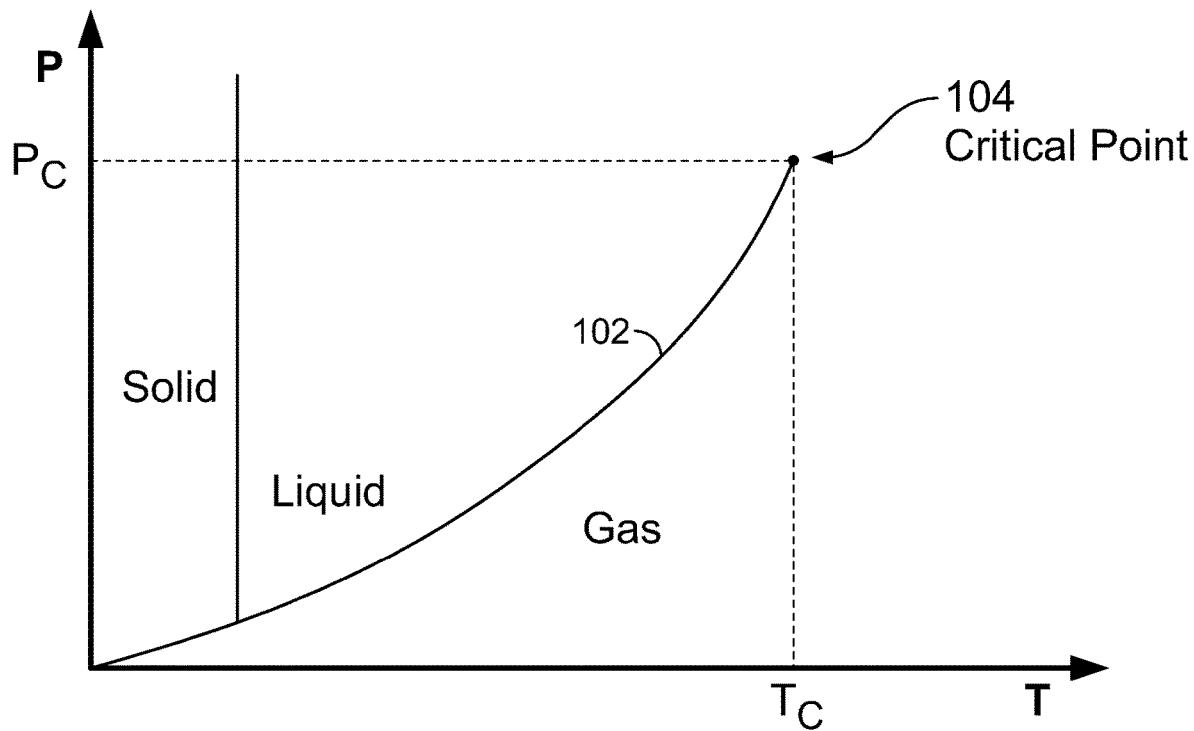
FIG. 1 illustrates a typical cryogen phase diagram.

It is to be understood that the embodiments of the invention described herein are not limited to particular variations set forth herein as various changes or modifications may be made to the embodiments of the invention described and equivalents may be substituted without departing from the spirit and scope of the embodiments of the invention. As will be apparent to those of skill in the art upon reading this disclosure, each of the individual embodiments described and illustrated herein has discrete components and features that may be readily separated from or combined with the features of any of the other several embodiments without departing from the scope or spirit of the embodiments of the present invention. In addition, many modifications may be made to adapt a particular situation, material, composition of matter, process, process act(s) or step(s) to the objective(s), spirit or scope of the embodiments of the present invention. All such modifications are intended to be within the scope of the claims made herein.

Moreover, while methods may be depicted in the drawings or described in the specification in a particular order, such methods need not be performed in the particular order shown or in sequential order, and that all methods need not be performed, to achieve desirable results. Other methods that are not depicted or described can be incorporated in the example methods and processes. For example, one or more additional methods can be performed before, after, simultaneously, or between any of the described methods. Further, the methods may be rearranged or reordered in other implementations. Also, the separation of various system components in the implementations described above should not be understood as requiring such separation in all implementations, and it should be understood that the described components and systems can generally be integrated together in a single product or packaged into multiple products. Additionally, other implementations are within the scope of this disclosure.

Conditional language, such as "can," "could," "might," or "may," unless specifically stated otherwise, or otherwise understood within the context as used, is generally intended to convey that certain embodiments include or do not include, certain features, elements, and/or steps. Thus, such conditional language is not generally intended to imply that features, elements, and/or steps are in any way required for one or more embodiments.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It will be understood that when an element is referred to as being "connected" or "coupled" to another element, it can be directly connected or coupled to the other element or intervening elements may be present. In contrast, if an element is referred to as being "directly connected" or "directly coupled" to another element, there are no intervening elements present.

It will also be understood that, although the terms first, second, etc. may be used herein to describe various elements, these elements should not be limited by these terms. These terms are only used to distinguish one element from another. Thus, a first element could be termed a second element without departing from the teachings of the present invention.

Language of degree used herein, such as the terms "approximately," "about," "generally," and "substantially," represent a value, amount, or characteristic close to the stated value, amount, or characteristic that still performs a desired function or achieves a desired result. For example, the terms "approximately," "about," "generally," and "substantially" may refer to an amount that is within less than or equal to 10% of, within less than or equal to 5% of, within less than or equal to 1% of, within less than or equal to 0.1% of, and within less than or equal to 0.01% of the stated amount. If the stated amount is 0 (e.g., none, having no), the above recited ranges can be specific ranges, and not within a particular % of the value. Additionally, numeric ranges are inclusive of the numbers defining the range, and any individual value provided herein can serve as an endpoint for a range that includes other individual values provided herein. For example, a set of values such as 1, 2, 3, 8, 9, and 10 is also a disclosure of a range of numbers from 1-10, from 1-8, from 3-9, and so forth.

Some embodiments have been described in connection with the accompanying drawings. The figures are drawn to scale, but such scale should not be limiting, since dimensions and proportions other than what are shown are contemplated and are within the scope of the disclosed inventions. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

While a number of embodiments and variations thereof have been described in detail, other modifications and methods of using the same will be apparent to those of skill in the art. Accordingly, it should be understood that various applications, modifications, materials, and substitutions can be made of equivalents without departing from the unique and inventive disclosure herein or the scope of the claims.

All existing subject matter mentioned herein (e.g., publications, patents, patent applications and hardware) is incorporated by reference herein in its entirety except insofar as the subject matter may conflict with that of the present invention (in which case what is present herein shall prevail).

Embodiments of the invention make use of thermodynamic processes using cryogens that provide cooling without encountering the phenomenon of vapor lock.

Cryogen Phase Diagram and Near Critical Point

This application uses phase diagrams to illustrate various thermodynamic processes. An example phase diagram is shown in FIG. 1. The phase diagram includes axes that correspond to pressure P and temperature T, and a phase line 102 that delineates the locus of all (P, T) points where liquid and gas coexist. For (P, T) values to the left of the phase line 102, the cryogen is in a liquid state, generally achieved with higher pressures and lower temperatures, while (P, T) values to the right of the phase line 102 define regions where the cryogen is in a gaseous state, generally achieved with lower pressures and higher temperatures. The phase line 102 ends abruptly in a single point known as the critical point 104. In the case of nitrogen N$_2$, the critical point is at P$_c$=3.396 MPa and T$_c$=−147.15° C.

When a fluid has both liquid and gas phases present during a gradual increase in pressure, the system moves up along the liquid-gas phase line 102. In the case of N$_2$, the liquid at low pressures is up to two hundred times more dense than the gas phase. A continual increase in pressure causes the density of the liquid to decrease and the density of the gas phase to increase, until they are equal only at the critical point 104. The distinction between liquid and gas disappears at the critical point 104. The blockage of forward flow by gas expanding ahead of the liquid cryogen ("vapor lock") is thus avoided when a cryogen flows at conditions surrounding the critical point, defined herein as "near-critical conditions." Factors that allow greater departure from the critical point while maintaining a functional flow include greater speed of cryogen flow, larger diameter of the flow lumen and lower heat load upon the thermal exchanger, or cryo-treatment region.

As the critical point is approached from below, the vapor phase density increases and the liquid phase density decreases until right at the critical point, where the densities of these two phases are exactly equal. Above the critical point, the distinction of liquid and vapor phases vanishes, leaving only a single, supercritical phase, where the fluid has the properties of both a liquid and a gas (i.e., a dense fluid without surface tension capable of frictionless flow).

Van der Waals thermodynamic equation of state is a well-established equation for describing gases and liquids:

$$(p+3/v^2)(3v-1)=8t \qquad [\text{Eq. 1}]$$

where p=P/P$_c$, v=V/V$_c$, and t=T/T$_c$, and P$_c$, V$_c$, and T$_c$ are the critical pressure, critical molar volume, and the critical temperature respectively.

The variables v, p, and t are often referred to as the "reduced molar volume," the "reduced pressure," and the "reduced temperature," respectively. Hence, any two substances with the same values of p, v, and t are in the same thermodynamic state of fluid near its critical point. Eq. 1 is thus referred to as embodying the "Law of Corresponding States." This is described more fully in H. E. Stanley, *Introduction to Phase Transitions and Critical Phenomena* (Oxford Science Publications, 1971), the entire disclosure of which is incorporated herein by reference in its entirety for all purposes.

In embodiments of the present invention, the reduced pressure p is fixed at a constant value of approximately one, and hence at a fixed physical pressure near the critical pressure, while the reduced temperature t varies with the heat load applied to the device. If the reduced pressure p is a constant set by the engineering of the system, then the reduced molar volume v is an exact function of the reduced temperature t.

In other embodiments of the present invention, the operating pressure p may be adjusted so that over the course of variations in the temperature t of the device, v is maintained below some maximum value at which the vapor lock condition will result. It is generally desirable to maintain p at the lowest value at which this is true because boosting the pressure to achieve higher values of p may involve use of a more complex and more expensive compressor, resulting in more expensive procurement and maintenance of the entire apparatus support system and lower overall cooling efficiency.

The conditions for v depend in a complex way on the volume flow rate dV/dt, the heat capacity of the liquid and vapor phases, and the transport properties such as the thermal conductivity, viscosity, etc., in both the liquid and the vapor. The exact relationship is not derived here in closed form algebraically, but may be determined numerically by integrating the model equations that describe mass and heat transport within the cooling device. Conceptually, vapor lock occurs when the rate of heating of the tip (or other device structure for transporting the cryogen and cooling the tissue) produces the vapor phase. The cooling power of this vapor phase, which is proportional to the flow rate of the vapor multiplied by its heat capacity divided by its molar volume, is not able to keep up with the rate of heating to the tip. When this occurs, more and more of the vapor phase is formed in order to absorb the excess heat through the conversion of the liquid phase to vapor in the cryogen flow. This creates a runaway condition where the liquid converts into vapor phase to fill the tip, and effectively all cryogen flow stops due to the large pressure that results in this vapor phase as the heat flow into the tip increases its temperature and pressure rapidly. This condition is called "vapor lock."

In accordance with one embodiment of the present invention, the liquid and vapor phases are substantially identical in their molar volume. The cooling power is at the critical point, and the cooling system avoids vapor lock. Additionally, at conditions slightly below the critical point, the apparatus may avoid vapor lock as well.

Cryoablation System

Figure 2:
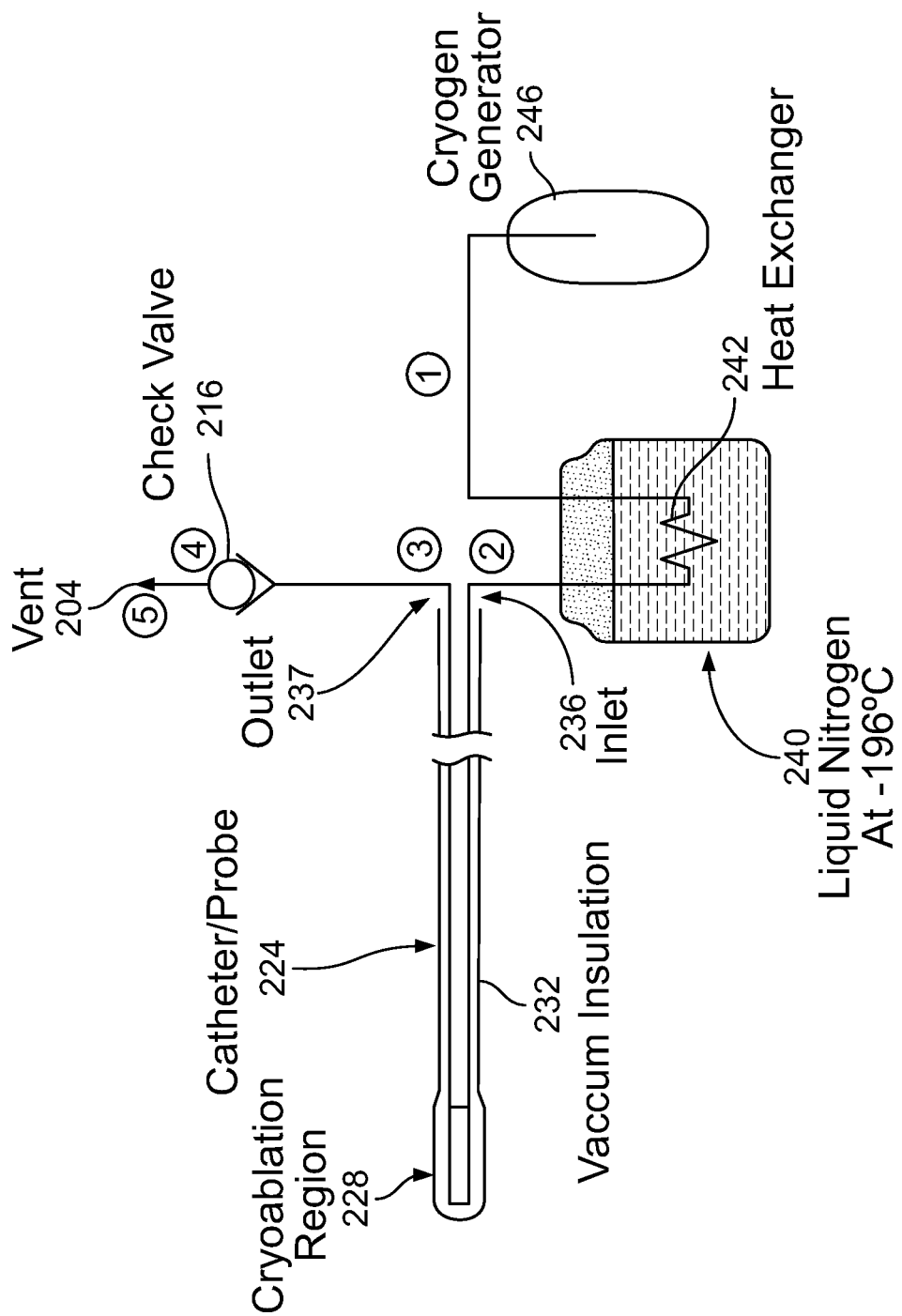
FIG. 2 is a schematic illustration of a cryogenic cooling system.
Figure 3:
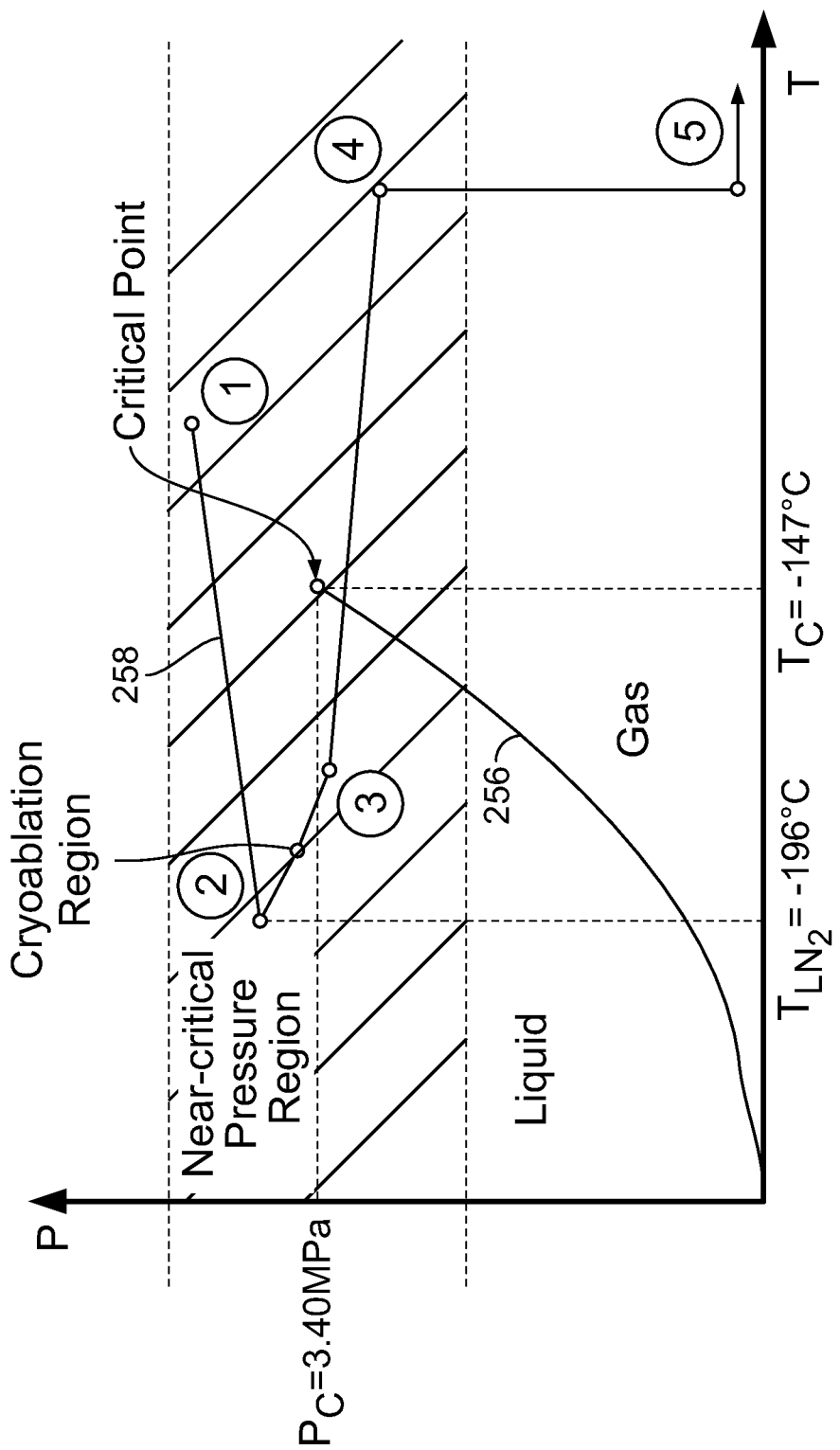
FIG. 3 is a cryogen phase diagram corresponding to the system shown in FIG. 2 where the cryogen is $N_2$.

FIG. 2 provides a schematic illustration of a structural arrangement for a cryogenic system in one embodiment, and FIG. 3 provides a phase diagram that illustrates a thermodynamic path taken by the cryogen when the system of FIG. 2 is operated. The circled numerical identifiers in the two figures correspond so that a physical position is indicated in FIG. 2 where operating points identified along the thermodynamic path are achieved. The following description thus sometimes makes simultaneous reference to both the structural drawing of FIG. 2 and to the phase diagram of FIG. 3 in describing physical and thermodynamic aspects of the cooling flow.

For purposes of illustration, both FIGS. 2 and 3 make specific reference to a nitrogen cryogen, but this is not intended to be limiting. Embodiments of the invention may more generally be used with any suitable cryogen such as, for example, argon, neon, helium, hydrogen, and oxygen.

In FIG. 3, the liquid-gas phase line is identified with reference label 256 and the thermodynamic path followed by the cryogen is identified with reference label 258.

A cryogenic generator 246 is used to supply the cryogen at a pressure that exceeds the critical-point pressure P$_c$ for the cryogen at its outlet, referenced in FIGS. 2 and 3 by label 0. The cooling cycle may generally begin at any point in the phase diagram having a pressure above or slightly below P$_c$, although it is advantageous for the pressure to be near the critical-point pressure P$_c$. The cooling efficiency of the process described herein is generally greater when the initial pressure is near the critical-point pressure P, so that at higher pressures there may be increased energy requirements to achieve the desired flow. Thus, embodiments may sometimes incorporate various higher upper boundary pressure but generally begin near the critical point, such as between 0.8 and 1.2 times P$_c$, and in one embodiment at about 0.85 times P$_c$.

As used herein, the term "near critical" is meant to refer to near the liquid-vapor critical point. Use of this term is equivalent to "near a critical point" and it is the region where the liquid-vapor system is adequately close to the critical point, where the dynamic viscosity of the fluid is close to that of a normal gas and much less than that of the liquid; yet, at the same time its density is close to that of a normal liquid state. The thermal capacity of the near critical fluid is even greater than that of its liquid phase. The combination of gas-like viscosity, liquid-like density and very large thermal capacity makes it a very efficient cooling agent. Reference to a near critical point refers to the region where the liquid-vapor system is adequately close to the critical point so that the fluctuations of the liquid and vapor phases are large enough to create a large enhancement of the heat capacity over its background value. The near critical temperature is a temperature within ±10% of the critical point temperature. The near critical pressure is between 0.8 and 1.2 times the critical point pressure.

Referring again to FIG. 2, the cryogen is flowed through a tube, at least part of which is surrounded by a reservoir 240 of the cryogen in a liquid state, reducing its temperature without substantially changing its pressure. In FIG. 2, reservoir is shown as liquid $N_2$, with a heat exchanger 242 provided within the reservoir 240 to extract heat from the flowing cryogen. Outside the reservoir 240, thermal insulation may be provided around the tube to prevent unwanted warming of the cryogen as it is flowed from the cryogen generator 246. At point ②, after being cooled by being brought into thermal contact with the liquid cryogen, the cryogen has a lower temperature but is at substantially the initial pressure. In some instances, there may be a pressure change, as is indicated in FIG. 3 in the form of a slight pressure decrease, provided that the pressure does not drop substantially below the critical-point pressure $P_c$, i.e. does not drop below the determined minimum pressure. In the example shown in FIG. 3, the temperature drop as a result of flowing through the liquid cryogen is about 50° C.

The cryogen is then provided to a device for use in cryogenic applications. In the exemplary embodiment shown in FIG. 2, the cryogen is provided to an inlet 236 of a catheter 224, such as may be used in medical cryogenic endovascular applications, but this is not a requirement.

Indeed, the form of the medical device may vary widely and include without limitation: instruments, appliances, catheters, devices, tools, apparatus', and probes regardless of whether such probe is short and rigid, or long and flexible, and regardless of whether it is intended for open, minimal, non-invasive, manual or robotic surgeries.

In embodiments, the cryogen may be introduced through a proximal portion of a catheter, continue along a flexible intermediate section of the catheter, and into the distal treatment section of the catheter. As the cryogen is transported through the catheter, and across the cryoablation treatment region 228, between labels ② and ③ in FIGS. 2 and 3, there may be a slight change in pressure and/or temperature of the cryogen as it moves through the interface with the device, e.g. cryoablation region 228 in FIG. 2. Such changes may typically show a slight increase in temperature and a slight decrease in pressure. Provided the cryogen pressure remains above the determined minimum pressure (and associated conditions), slight increases in temperature do not significantly affect performance because the cryogen simply moves back towards the critical point without encountering the liquid-gas phase line 256, thereby avoiding vapor lock.

Flow of the cryogen from the cryogen generator 246 through the catheter 224 or other device may be controlled in the illustrated embodiment with an assembly that includes a check valve 216, a flow impedance, and/or a flow controller. The catheter 224 itself may comprise a vacuum insulation 232 (e.g., a cover or jacket) along its length and may have a cold cryoablation region 228 that is used for the cryogenic applications. Unlike a Joule-Thomson probe, where the pressure of the working cryogen changes significantly at the probe tip, these embodiments of the invention provide relatively little change in pressure throughout the apparatus. Thus, at point ④, the temperature of the cryogen has increased approximately to ambient temperature, but the pressure remains elevated. By maintaining the pressure above or near the critical-point pressure $P_c$ as the cryogen is transported through the catheter, vapor lock are avoided.

The cryogen pressure returns to ambient pressure at point ⑤. The cryogen may then be vented through vent 204 at substantially ambient conditions.

Examples of cryoablation systems, their components, and various arrangements are described in the following commonly-assigned U.S. patents and U.S. patent applications: U.S. patent application Ser. No. 10/757,768, which issued as U.S. Pat. No. 7,410,484, on Aug. 12, 2008 entitled "CRYOTHERAPY PROBE," filed Jan. 14, 2004 by Peter J. Littrup et al.; U.S. patent application Ser. No. 10/757,769, which issued as U.S. Pat. No. 7,083,612 on Aug. 1, 2006, entitled "CRYOTHERAPY SYSTEM," filed Jan. 14, 2004 by Peter J. Littrup et al.; U.S. patent application Ser. No. 10/952,531, which issued as U.S. Pat. No. 7,273,479 on Sep. 25, 2007 entitled "METHODS AND SYSTEMS FOR CRYOGENIC COOLING," filed Sep. 27, 2004 by Peter J. Littrup et al.; U.S. patent application Ser. No. 11/447,356, which issued as U.S. Pat. No. 7,507,233 on Mar. 24, 2009 entitled "CRYOTHERAPY SYSTEM," filed Jun. 6, 2006 by Peter Littrup et al.; U.S. patent application Ser. No. 11/846,226, which issued as U.S. Pat. No. 7,921,657 on Apr. 12, 2011 entitled "METHODS AND SYSTEMS FOR CRYOGENIC COOLING," filed Aug. 28, 2007 by Peter Littrup et al.; U.S. patent application Ser. No. 12/018,403, which issued as U.S. Pat. No. 8,591,503 on Nov. 26, 2013 entitled "CRYOTHERAPY PROBE," filed Jan. 23, 2008 by Peter Littrup et al.; U.S. patent application Ser. No. 13/046,274, which issued as U.S. Pat. No. 8,387,402 on Mar. 5, 2013 entitled "METHODS AND SYSTEMS FOR CRYOGENIC COOLING," filed Mar. 11, 2011 by Peter Littrup et al., U.S. patent application Ser. No. 14/087,947, which is pending entitled "CRYOTHERAPY PROBE," filed Nov. 22, 2013 by Peter Littrup et al.; U.S. patent application Ser. No. 12/744,001, which issued as U.S. Pat. No. 8,740,891, on Jun. 3, 2014 entitled "FLEXIBLE MULTI-TUBULAR CRYOPROBE," filed Jul. 29, 2010 by Alexei Babkin et al.; U.S. patent application Ser. No. 12/744,033, which issued as U.S. Pat. No. 8,740,892, on Jun. 3, 2014 entitled "EXPANDABLE MULTI-TUBULAR CRYOPROBE," filed Jul. 29, 2010 by Alexei Babkin et al. and U.S. patent application Ser. No. 14/915,632 entitled "ENDOVASCULAR NEAR CRITICAL FLUID BASED CRYOABLATION CATHETER AND RELATED METHODS," filed Sep. 22, 2014 by Alexei Babkin, et al., the contents of each of the above-identified U.S. patents/applications are incorporated herein by reference in their entireties for all purposes.

Figure 4:
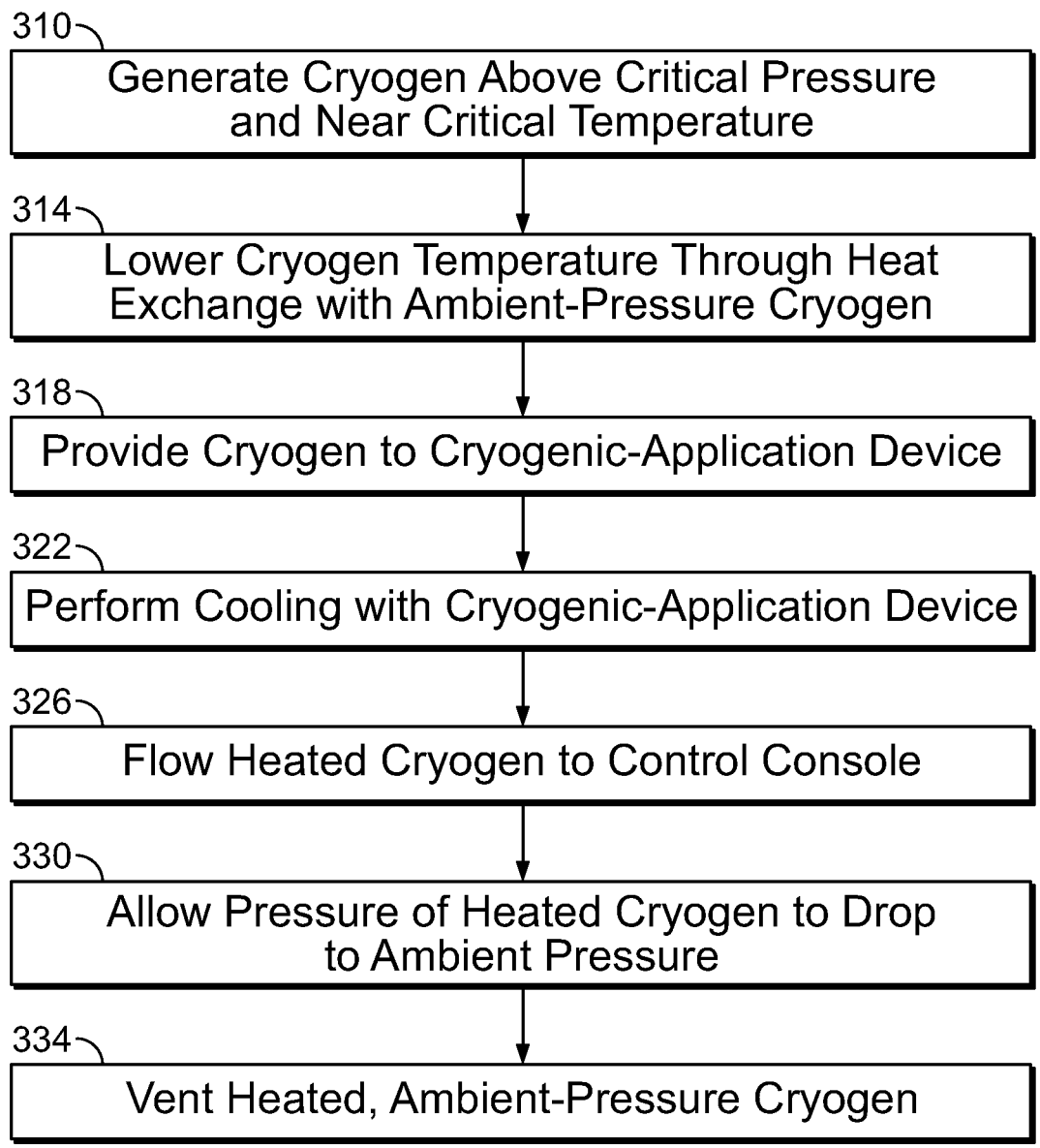
FIG. 4 provides a flow diagram that summarizes aspects of the cooling system of FIG. 2.

A method for cooling a target tissue in which the cryogen follows a thermodynamic path similar to that shown in FIG. 3 is illustrated with the flow diagram of FIG. 4. At block 310, the cryogen is generated with a pressure that exceeds the critical-point pressure and is near the critical-point temperature. The temperature of the generated cryogen is lowered at block 314 through heat exchange with a substance having a lower temperature. In some instances, this may conveniently be performed by using heat exchange with an ambient-pressure liquid state of the cryogen, although the heat exchange may be performed under other conditions in different embodiments. For example, a different cryogen might be used in some embodiments, such as by providing heat exchange with liquid nitrogen when the working fluid is argon. Also, in other alternative embodiments, heat exchange may be performed with a cryogen that is at a pressure that differs from ambient pressure, such as by providing the cryogen at lower pressure to create a colder ambient.

The further cooled cryogen is provided at block 318 to a cryogenic-application device, which may be used for a cooling application at block 322. The cooling application may comprise chilling and/or freezing, depending on whether an object is frozen with the cooling application. The temperature of the cryogen is increased as a result of the cryogen application, and the heated cryogen is flowed to a control console at block 326. While there may be some variation, the cryogen pressure is generally maintained greater than the critical-point pressure throughout blocks 310-326; the principal change in thermodynamic properties of the cryogen at these stages is its temperature. At block 330, the pressure of the heated cryogen is then allowed to drop to ambient pressure so that the cryogen may be vented, or recycled, at block 334. In other embodiments, the remaining pressurized cryogen at block 326 may also return along a path to block 310 to recycle rather than vent the cryogen at ambient pressure.

Cryoablation Catheters

Figures 5A, 5B:
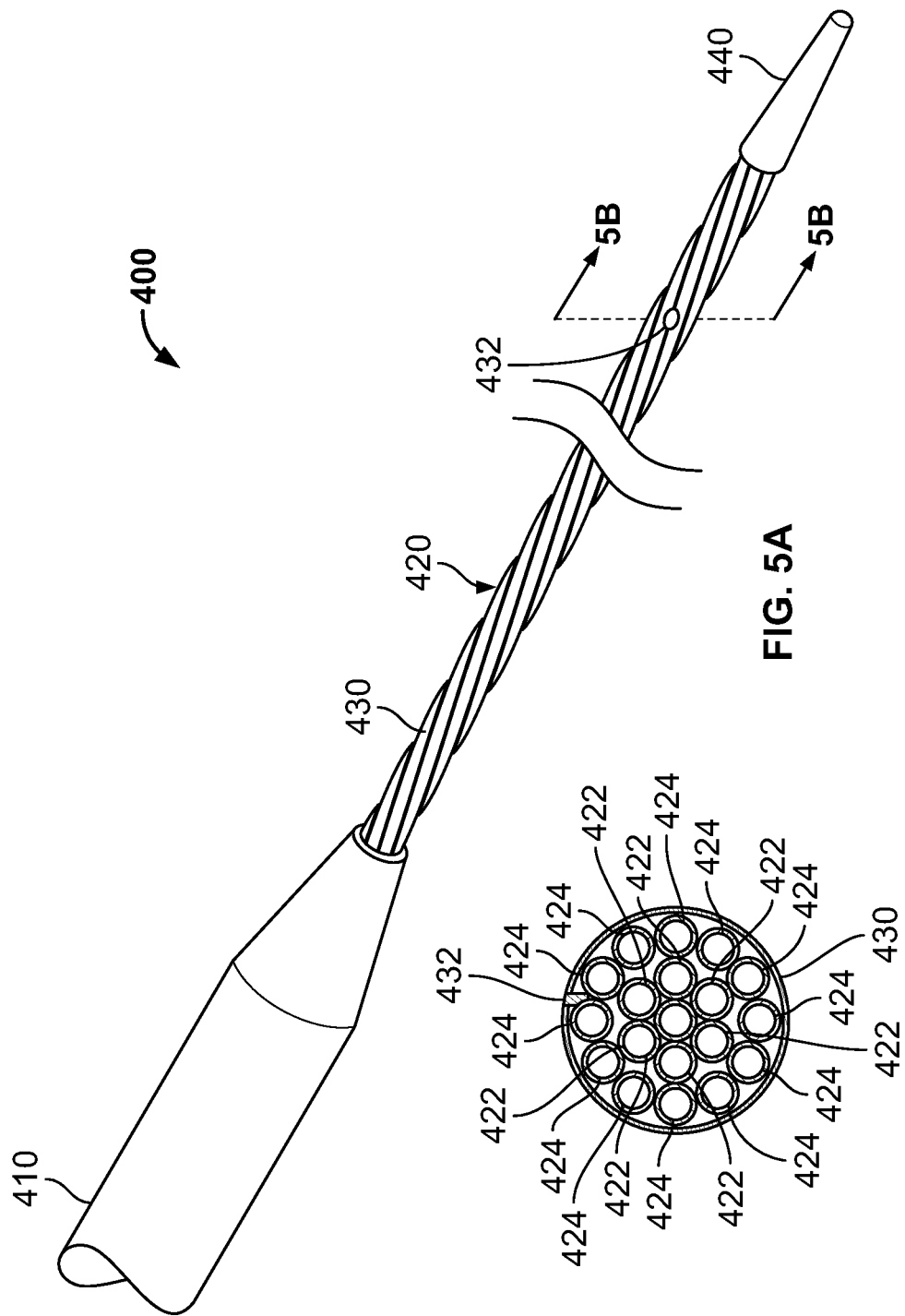
FIG. 5A is a perspective view of a cryoablation catheter, according to an embodiment of the invention.
FIG. 5B is a cross-sectional view taken along line 5B-5B of FIG. 5A.

Embodiments of the cryoablation apparatus of the present invention may have a wide variety of configurations. For example, one embodiment of the present invention is a flexible catheter 400 as shown in FIG. 5A. The catheter 400 includes a proximally disposed housing or connector 410 adapted to fluidly connect to a fluid source (not shown).

A plurality of fluid transfer tubes 420 are shown extending from the connector 410. These tubes include a set of inlet fluid transfer tubes 422 for receiving the inlet flow from the connector and a set of outlet fluid transfer tubes 424 for discharging flow from the connector 410.

In embodiments each of the fluid transfer tubes is formed of material that maintains structural and mechanical integrity in a full range of temperatures from −200° C. to ambient temperature. In embodiments, the fluid transfer tubes 420 are formed of annealed stainless steel or a polymer such as polyimide. In such configurations, the material may maintain flexibility at near critical temperature. In embodiments, each fluid transfer tube has an inside diameter in a range of between about 0.1 mm and 1 mm (preferably between about 0.2 mm and 0.5 mm). Each fluid transfer tube may have a wall thickness in a range of between about 0.01 mm and 0.3 mm (preferably between about 0.02 mm and 0.1 mm).

An end cap 440 is positioned at the ends of the fluid transfer tubes to provide fluid transfer from the inlet fluid transfer tubes to the outlet fluid transfer tubes. The endcap 440 is shown having an atraumatic tip. The endcap 440 may be any suitable element for providing fluid transfer from the inlet fluid transfer tubes to the outlet fluid transfer tubes. For example, endcap 440 may define an internal chamber, cavity, or passage serving to fluidly connect tubes 422,424.

With reference to FIG. 5B, an outer sheath 430 is shown surrounding the tube bundle 420. The outer sheath serves to hold the tubes in a tubular arrangement, and protect the construct from being penetrated or disrupted by foreign objects and obstacles.

A temperature sensor 432 is shown on the surface of the distal section. Temperature sensor may be a thermocouple to sense a temperature corresponding to the adjacent tissue, and sends the signal back through a wire in the tube bundle to the console for processing. Temperature sensor may be placed elsewhere along the shaft or within one or more of the fluid transport tubes to determine a temperature difference between inflow and outflow.

There are many configurations for tube arrangements. In embodiments the fluid transfer tubes are formed of a circular array, wherein the set of inlet fluid transfer tubes comprises at least one inlet fluid transfer tube 422 defining a central region of a circle and wherein the set of outlet fluid transfer tubes 424 comprises a plurality of outlet fluid transfer tubes spaced about the central region in a circular pattern. In the configuration shown in FIG. 5B, the fluid transfer tubes 422,424 fall within this class of embodiments.

During operation, the cryogen/cryogenic fluid arrives at the catheter through a supply line from a suitable cryogen source at a temperature close to −200° C. The cryogen is circulated through the multi-tubular freezing zone provided by the exposed fluid transfer tubes, and returns to the connector. Cryogen flows into the freeze zone through the inlet fluid transfer tube 422 and flows out of the freeze zone through the outlet fluid transfer tubes 424.

In embodiments, the nitrogen flow does not form gaseous bubbles inside the small diameter tubes under any heat load, so as not to create a vapor lock that limits the flow and the cooling power. By operating at the near critical condition for at least an initial period of energy application, the vapor lock is eliminated as the distinction between the liquid and gaseous phases disappears. After initially operating under near critical conditions, e.g., for nitrogen, at a temperature near the critical temperature of −147.15° C. and a pressure near the critical pressure of 3.396 MPa, the operating pressure may be decreased as is disclosed and described in commonly assigned U.S. patent application Ser. No. 14/919,681 entitled "PRESSURE MODULATED CRYOABLATION SYSTEM AND RELATED METHODS," filed Oct. 21, 2015 by Alexei Babkin, the contents of which are incorporated herein by reference in their entirety for all purposes.

A multi-tube design may be preferably to a single-tube design because the additional tubes can provide a substantial increase in the heat exchange area between the cryogen and tissue. Depending on the number of tubes used, cryoinstruments can increase the contact area several times over previous designs having similarly sized diameters with single shafts/tubes. However, embodiments of the invention are not intended to be limited to a single or multi-tubular design except where specifically recited in the appended claims.

Cryoablation Console

FIG. 6 illustrates a cryoablation system 950 having a cart or console 960 and a cryoablation catheter 900 detachably connected to the console via a flexible elongate tube 910. The cryoablation catheter 900, which shall be described in more detail below in connection with FIG. 7, contains one or more fluid transport tubes to remove heat from the tissue.

The console 960 may include or house a variety of components (not shown) such as, for example, a generator, controller, tank, valve, pump, etc. A computer 970 and display 980 are shown in FIG. 6 positioned on top of cart for convenient user operation. Computer may include a controller, timer, or communicate with an external controller to drive components of the cryoablation systems such as a pump, valve or generator. Input devices such as a mouse 972 and a keyboard 974 may be provided to allow the user to input data and control the cryoablation devices.

In embodiments computer 970 is configured or programmed to control cryogen flowrate, pressure, and temperatures as described herein. Target values and real time measurement may be sent to, and shown, on the display 980.

Figure 7:
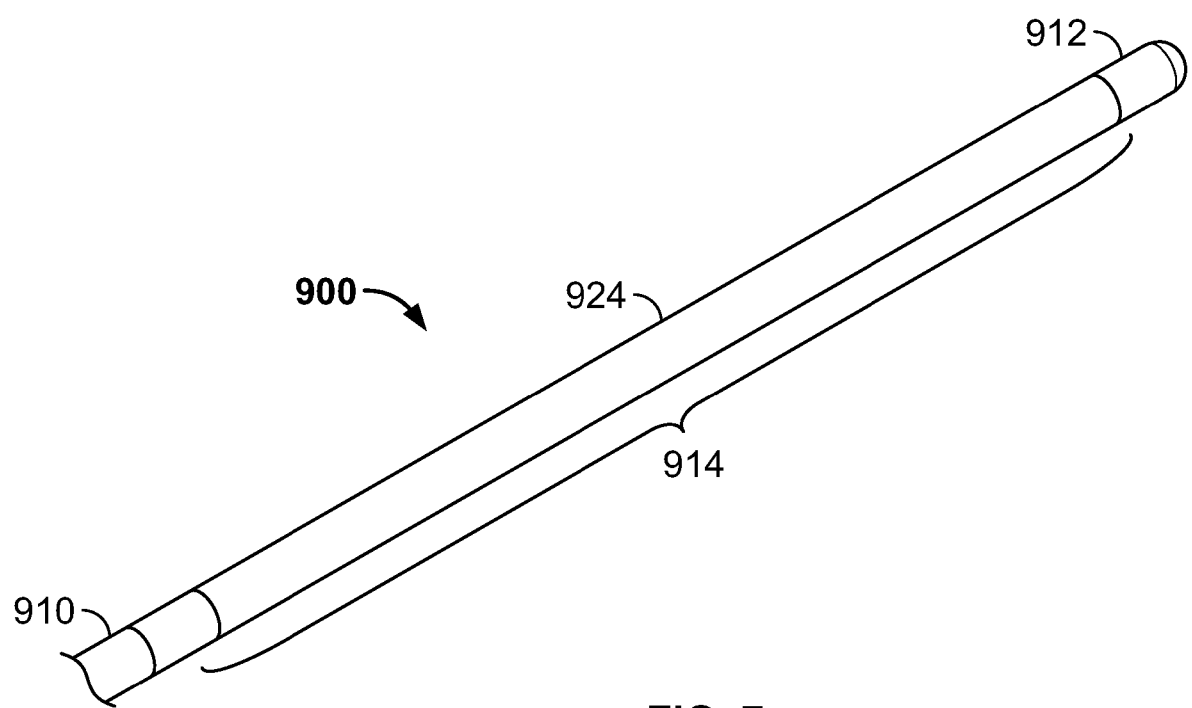
FIG. 7 is an enlarged perspective view of a distal section of the cryoablation catheter shown in FIG. 6.

FIG. 7 shows an enlarged view of distal section of cryoablation apparatus 900. The distal section 900 is similar to designs described above except that treatment region 914 includes a flexible protective cover 924. The cover serves to contain leaks of the cryogen in the event one of the fluid transport tubes is breached. Although a leak is not expected or anticipated in any of the fluid delivery transport tubes, the protective cover provides an extra or redundant barrier that the cryogen would have to penetrate in order to escape the catheter during a procedure. In embodiments the protective cover may be formed of metal.

Additionally, a thermally conducting liquid may be disposed within spaces or gaps between the transport tubes and the inner surface of the cover to enhance the device's thermal cooling efficiency during treatment. In embodiments the thermally conductive liquid is water.

Cover 924 is shown being tubular or cylindrically shaped and terminates at distal tip 912. As described herein, the cooling region 914 contains a plurality of fluid delivery and fluid return tubes to transport a cooling fluid through the treatment region 914 causing heat to be transferred/removed from the target tissue. In embodiments, the cryogen is transported through the tube bundle under physical conditions near the fluid's critical point in the phase diagram. The cover serves to, amongst other things, contain the cooling fluid and prevent it from escaping from the catheter in the event a leak forms in one of the delivery tubes.

Although a cover is shown in FIGS. 6-7, the invention is not intended to be so limited except as where recited in the appended claims. The apparatus may be provided with or without a protective cover and used to cool a target tissue.

Tube Within Tube

FIG. 8 shows a partial view of a cryoablation catheter 1010 according to another embodiment of the invention having a protective means to mitigate leaks in the event a cooling fluid/cryogen escapes from the cryogen delivery tubes described above. In particular, catheter 1010 comprises a plurality or bundle 1012 of flexible multi-layer cryoenergy transfer tubes, each of which comprises two tubes in a coaxial arrangement, namely a tube within a tube.

Figure 9A:
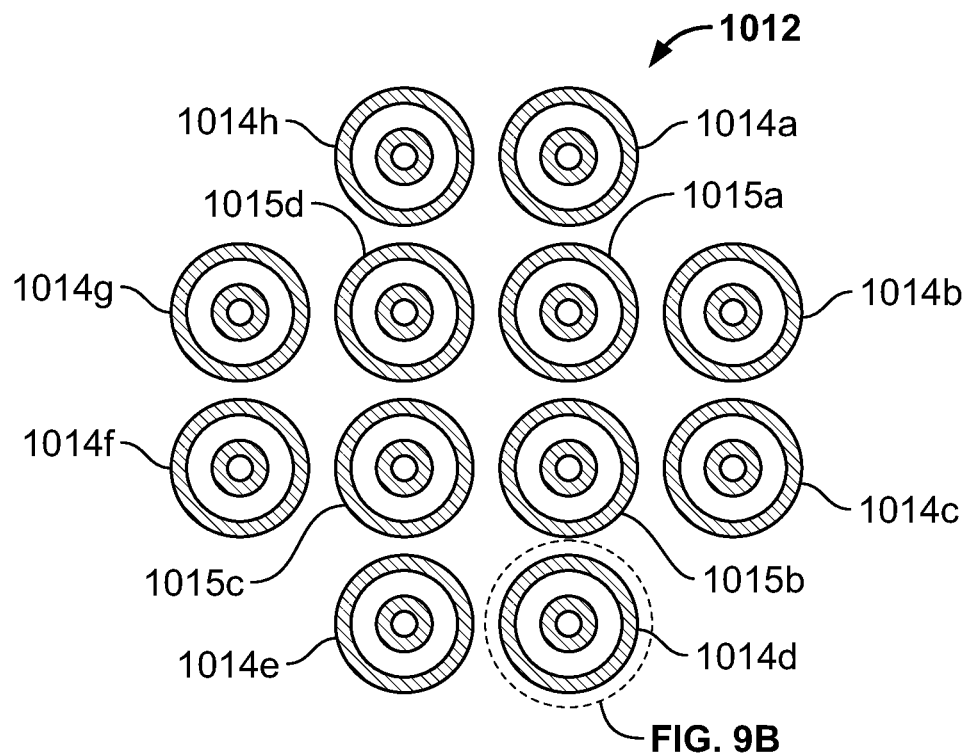
FIG. 9A is a cross-sectional view of an embodiment of a catheter shown in FIG. 8 taken along line 9A-9A in FIG. 8.

FIG. 9A shows a cross-sectional view taken along line 9A-9A of FIG. 8. The bundle 1012 of multilayer tubes is shown with the fluid delivery tubes 1014 and the fluid return tubes 1015 assembled in a parallel arrangement. The tube bundle 1012 is shown having 12 tubes/lines including four (4) fluid return tubes 1015a-1015d and eight (8) fluid delivery tubes 1014a-1014h. The fluid delivery tubes 1014a-1014h form a perimeter around the fluid return tubes 1015a-1015d. This arrangement ensures that colder delivery fluid/cryogen is adjacent to the tissue to be ablated/frozen and warmer return fluid/cryogen is shielded from the tissue to be ablated/frozen.

Figure 9B:
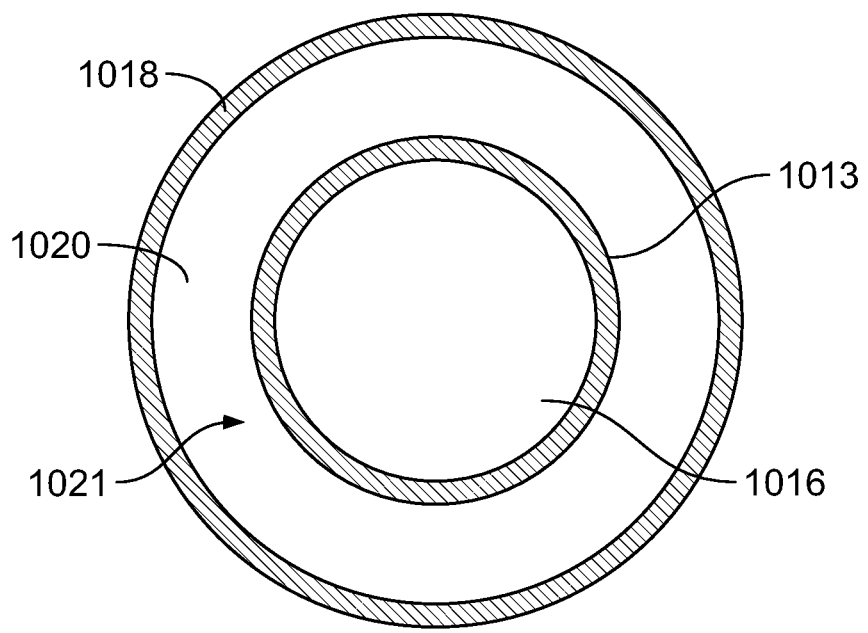
FIG. 9B is an enlarged view of one of the multi-layered tubes shown in FIG. 9A.

FIG. 9B shows an enlarged cross-sectional view of fluid delivery tube 1014d of FIG. 9A. The first or inner tube 1013 is shown coaxially surrounded by a second or outer tube 1018. A space or gap 1020 between the exterior surface of the inner tube 1013 and the interior surface of the outer tube 1018 is capable of being filled with a thermally conductive media 1021 as described herein. In embodiments, the gap 1020 has an annular shape. All of the fluid delivery tubes 1014 as well as the fluid return tubes 1015 can have a similar tube within a tube construction.

In the event of a leak of the cooling fluid 1016 or breach of the inner tube 1013 during use, the cooling fluid 1016 is contained within the gap 1020 between the inner tube 1013 and the outer tube 1018. This tube within a tube feature adds an additional safety element to the device as any leaking fluid/cryogen 1016 is contained within the catheter and is prevented from entering the patient. In some embodiments, a pressure sensor/device or gauge may be incorporated to monitor the pressure of the thermally conductive media 1021 in the gap 1020. Therefore, if fluid/cryogen 1016 breaches the inner tube 1013 and leaks into the gap 1020, the pressure in the gap 1020 and hence, the conductive media 1021 will increase. Should a change in pressure occur above a threshold limit, the system can be programmed to halt ablation thereby preventing potential harm to a patient and/or notify the user/physician of this change in pressure.

The inner tube 1013 may be fabricated and made from materials as described herein in connection with other flexible tubes for transporting the cooling fluid.

The outer tube 1018 material should also be flexible to enable elastic deflection of the distal treatment section to allow the distal treatment section to transform its shape as disclosed herein. In some embodiments, the outer tube is not inflatable, distensible nor expandable such that its size and shape remains substantially unaffected by the presence of the thermally conductive media 1021 contained therein. Non-limiting exemplary materials for the outer tube 1018 include polymers and metals or alloys. An example of an outer tube 1018 material is Nitinol or polyimide.

The number of tubes forming the tubular bundle 1012 may vary widely. In some embodiments, the tubular bundle 1012 includes 5-15 tubes, and more preferably, includes between 8-12 tubes comprising fluid delivery tubes 1014 and fluid return tubes 1015.

The cross-sectional profile of the tube bundle 1012 may also vary. Although FIG. 9A shows a substantially circular profile, in embodiments, the profile may be rectangular, square, cross or t-shaped, annular or circumferential, or another shape profile, including some of the arrangements described above. The tubes may also be braided, woven, twisted, or otherwise intertwined together, as depicted in commonly assigned U.S. patent application Ser. No. 14/915, 632 entitled "ENDOVASCULAR NEAR CRITICAL FLUID BASED CRYOABLATION CATHETER AND RELATED METHODS," filed Sep. 22, 2014 by Alexei Babkin, et al., the entire contents of which are incorporated herein by reference for all purposes.

The diameter of the freezing section or tubular bundle may vary. In embodiments, the diameter of the bundle ranges from about 1-3 mm, and is preferably about 2 mm. In embodiments, the diameter of the freezing section is between 2.5 and 3 mm.

Figure 9C:
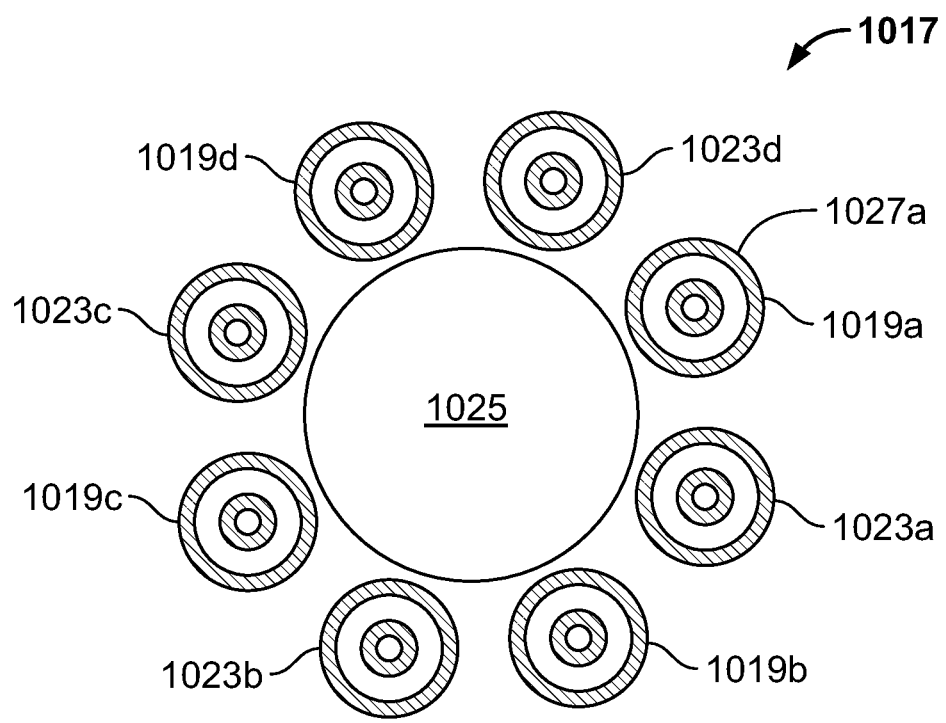
FIG. 9C is a cross sectional view of another embodiment of a cryoablation catheter.

FIG. 9C shows a cross-section of a cryoablation catheter having another tubular arrangement 1017. The eight (8) tubular elements (1019a-1019d and 1023a-1023d) are spaced or distributed circumferentially about a core element 1025. Preferably, as shown, fluid delivery elements/tubes (1019a-1019d) and fluid return elements/tubes (1023a-1023d) alternate along the circumference of the catheter.

Each inner tubular element (e.g., 1019a) includes an outer tubular element (e.g., 1027a) coaxially surrounding the inner tubular element thereby creating a space or gap which can be filled with a thermally conductive media/fluid as described with respect to FIG. 9B.

Steering elements, sensors and other functional elements may be incorporated into the catheter. In embodiments, steering elements are incorporated into a mechanical core such as the mechanical core 1025 shown in FIG. 9C.

Figure 10A:
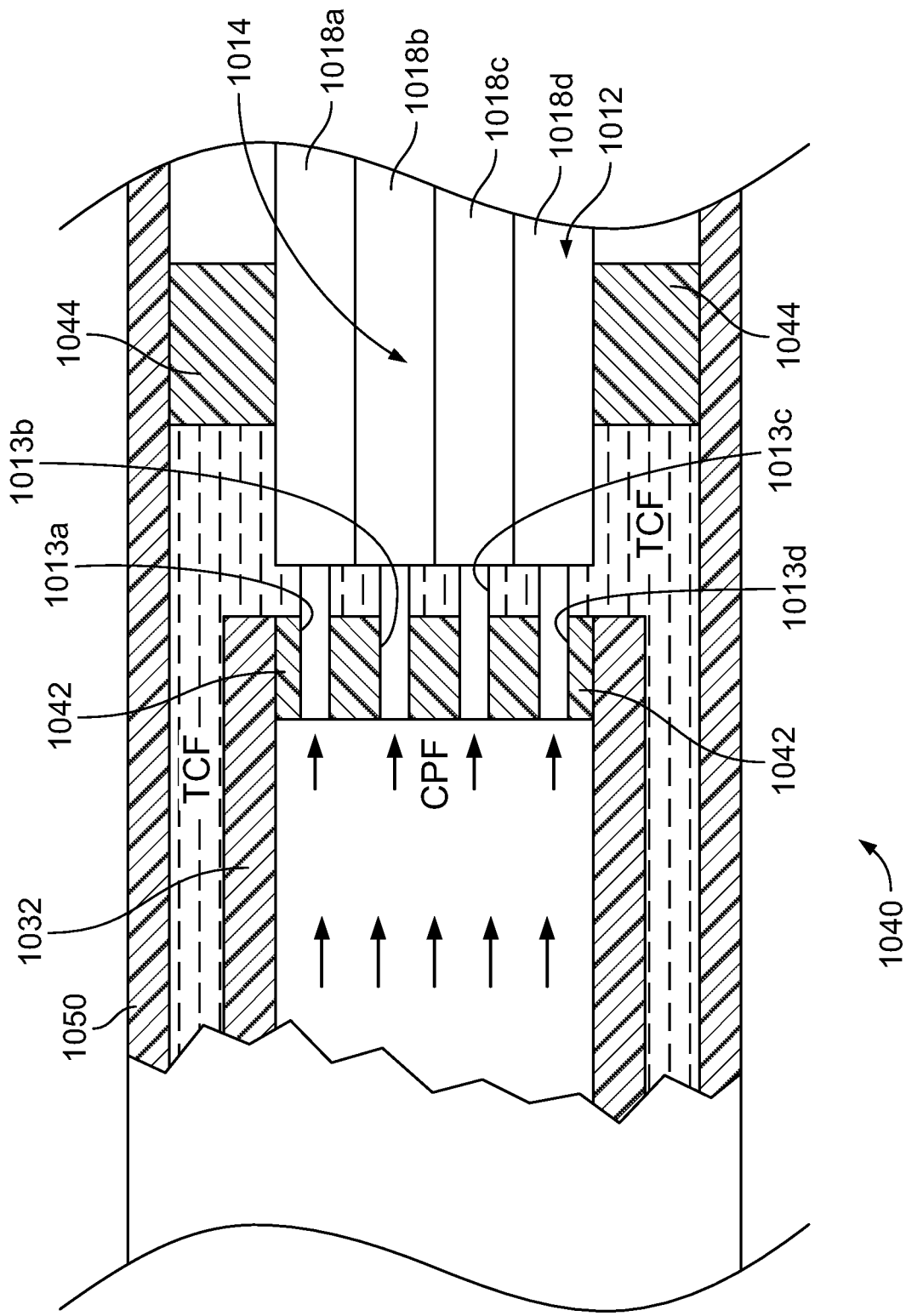
FIG. 10A is a partial sectional view of an embodiment of a catheter shown in FIG. 8.

FIG. 10A shows an enlarged cut-away view of the catheter at detail 10A in FIG. 8, illustrating tube bundle 1012 fluidly connected to the end portion 1040 of an intermediate section of the catheter 1010.

Figure 10B:
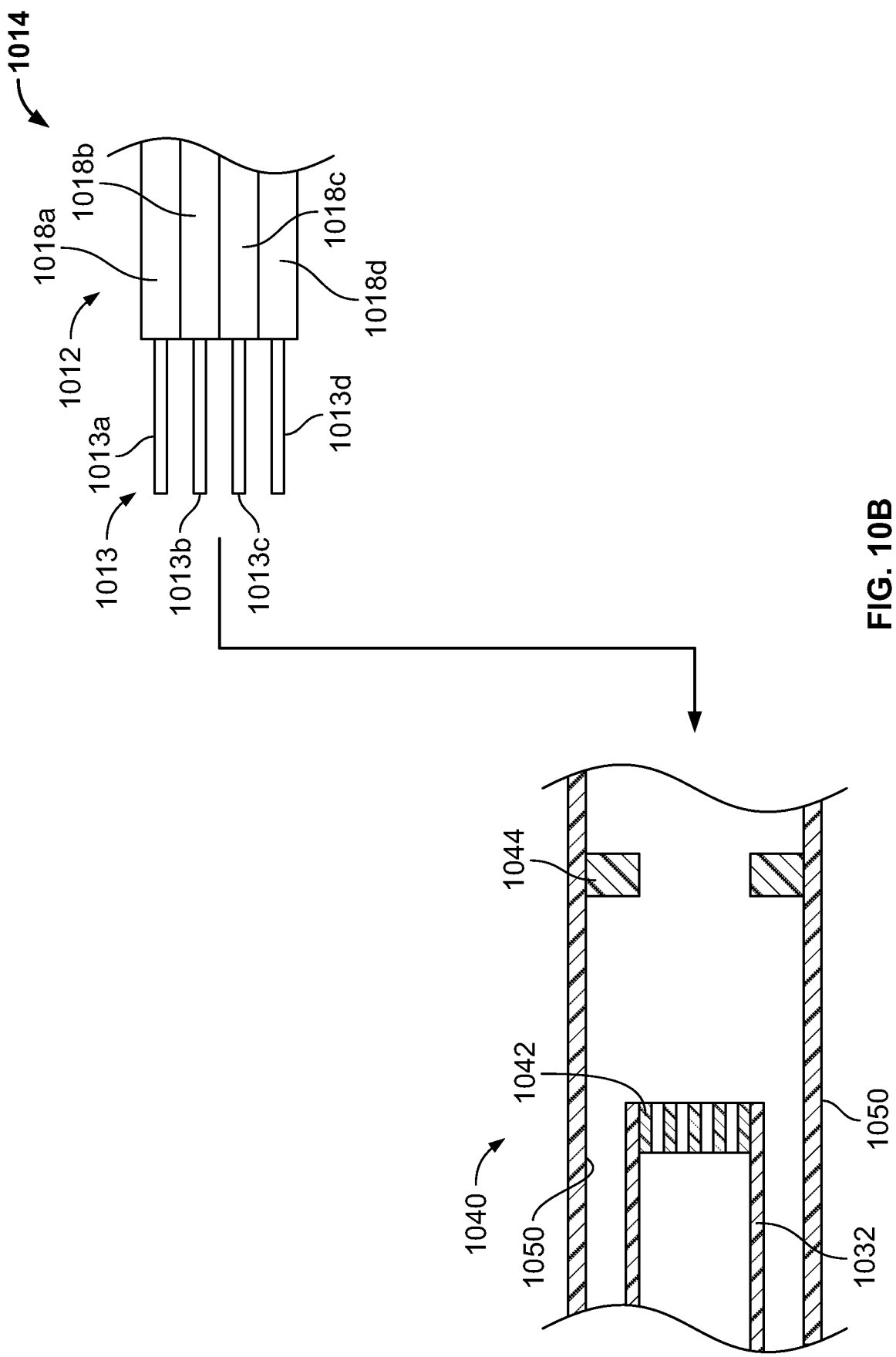
FIG. 10B is a partial exploded view of the proximal ends of the tube elements and the distal end of the intermediate section of an embodiment of a catheter shown in FIG. 8.

FIG. 10B shows an exploded view of a proximal section of the tube bundle 1012 and the intermediate section of catheter 1040. Tube bundle 1012, having inner tubular elements 1013*a*-1013*d* extending beyond outer tubular elements/covers 1018*a*-1018*d* of fluid delivery lines 1014, can be inserted into intermediate section of catheter 1040.

With reference to FIGS. 10A-10B, fluid delivery lines 1014 are shown bundled together and inserted/joined to main line 1032. An adhesive plug 1042 or seal, gasket, or stopper, etc. may be applied to facilitate and ensure a fluid seal between the tube members. The cooling power fluid (CPF) is transported to the fluid delivery lines 1014 from the fluid delivery main line 1032.

The proximal ends of outer tubular elements/covers 1018*a*-*d*, which are offset from proximal ends of inner tubular elements 1013*a*-*d*, are shown inserted into intermediate section 1040 of catheter such that the thermally conductive fluid (TCF) within lumen 1050 can fill gaps 1020 (FIG. 9B) of each of the multi-layer cryoenergy tubular elements. An adhesive plug 1044 (weld or bond) may be applied to facilitate a fluid tight and robust connection. Press fits, heat, and other fabrication techniques can be applied to join components as is known to those of skill in the art.

FIG. 11 shows another cryoablation catheter 500 including a distal treatment section 510, a handle 520, and an umbilical cord 530. The proximal end of the umbilical cord 530 terminates in connector 540, which is inserted into receptacle port 560 on console 550.

One or more ancillary connector lines 570 are shown extending proximally from the handle 520. The tubular lines 570 may serve to provide various functionality including without limitation (a) flushing; (b) vacuum; (c) thermally conductive liquid described above; and/or (d) temperature and pressure sensor conductors.

The catheter 500 is also shown having electrical connector 580 extending proximally from the handle 520. Electrical connector 580 may be coupled to an EP recording system for analyzing electrical information detected in the distal treatment section 510. Examples of systems for analyzing the electrical activity include, without limitation, the GE Healthcare CardioLab II EP Recording System, manufactured by GE Healthcare, USA and the LabSystem PRO EP Recording System manufactured by Boston Scientific Inc. (Marlborough, Mass.). The recorded electrical activity may also be used to evaluate or verify the continuous contact with the target tissue as described in commonly assigned International Patent Application No. PCT/US16/51954, entitled "TISSUE CONTACT VERIFICATION SYSTEM", filed Sep. 15, 2016 by Alexei Babkin, et al., the entire contents of which are incorporated herein by reference for all purposes.

Figure 12:
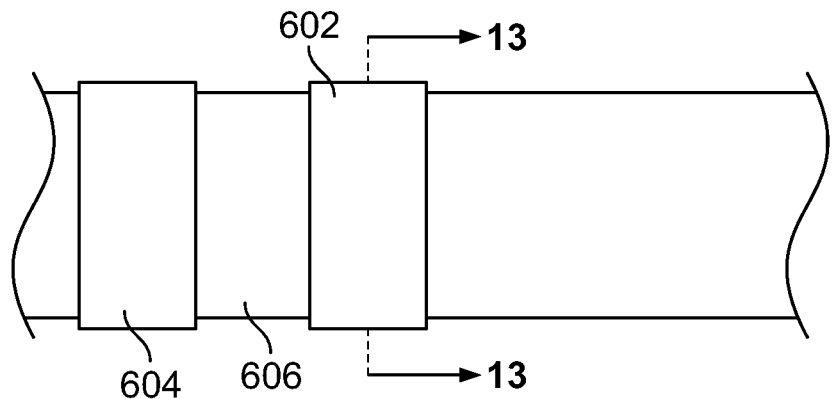
FIG. 12 is an enlarged view of a portion of the distal section shown in FIG. 11.

FIG. 12 shows an enlarged view of a portion of the distal section 510 of the catheter 500. Ring-shaped electrodes 602, 604 are circumferentially disposed about shaft 606. Although two electrodes are shown, more or less electrodes may be present on the shaft for sensing electrical activity. In embodiments, up to 12 or more electrodes are provided on the shaft. In one embodiment, 8 electrodes are axially spaced along the shaft 606.

Figure 13:
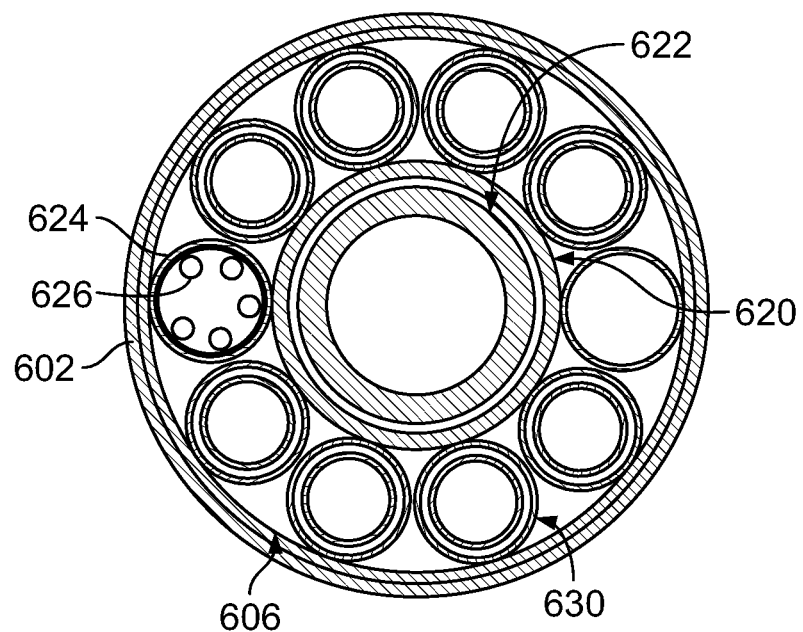
FIG. 13 is a cross sectional view of the catheter shown in FIG. 12 taken along line 13-13 in FIG. 12.

FIG. 13 is a cross section of the catheter shown in FIG. 12 taken along line 13-13. The catheter shaft is shown having a mechanical core 620 extending along the central axis, and a plurality of energy delivering tube constructs 630 extending parallel and circumferentially disposed about the mechanical core.

Each tube construct 630 is shown having dual layers as described above in connection with FIGS. 9-10 and a thermally conductive liquid layer disposed there between.

A tubular line 624 is shown for housing conducting wires 626 for the various sensors described herein.

The mechanical core 620 may be constructed to provide a preset shape to the catheter distal treatment section. With reference to FIG. 13, the mechanical core includes a metal tubular member 622 having a preset shape. The preset shape matches the target anatomy to make continuous contact with the target anatomy. An exemplary material for the preset tubular element 622 is Nitinol. FIG. 13 also shows an exterior layer or cover concentrically surrounding the Nitinol tube. The exterior cover may be a flexible polymer such as, for example, PET. Collectively, the inner PET layer 620 and outer shaft layer 606 form a fluidly-sealed annular chamber to house the plurality of tubular constructs 630.

Figure 14:
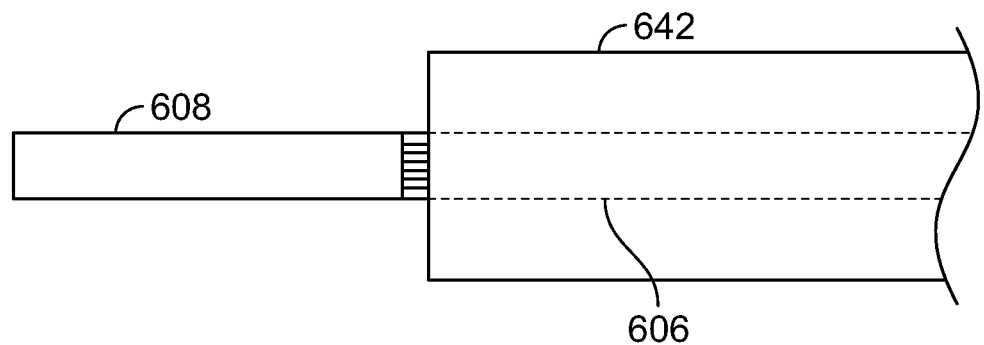
FIGS. 14-15 illustrate sequential deployment of the distal section of catheter shown in FIG. 11 from an outer sheath member.
Figure 15:
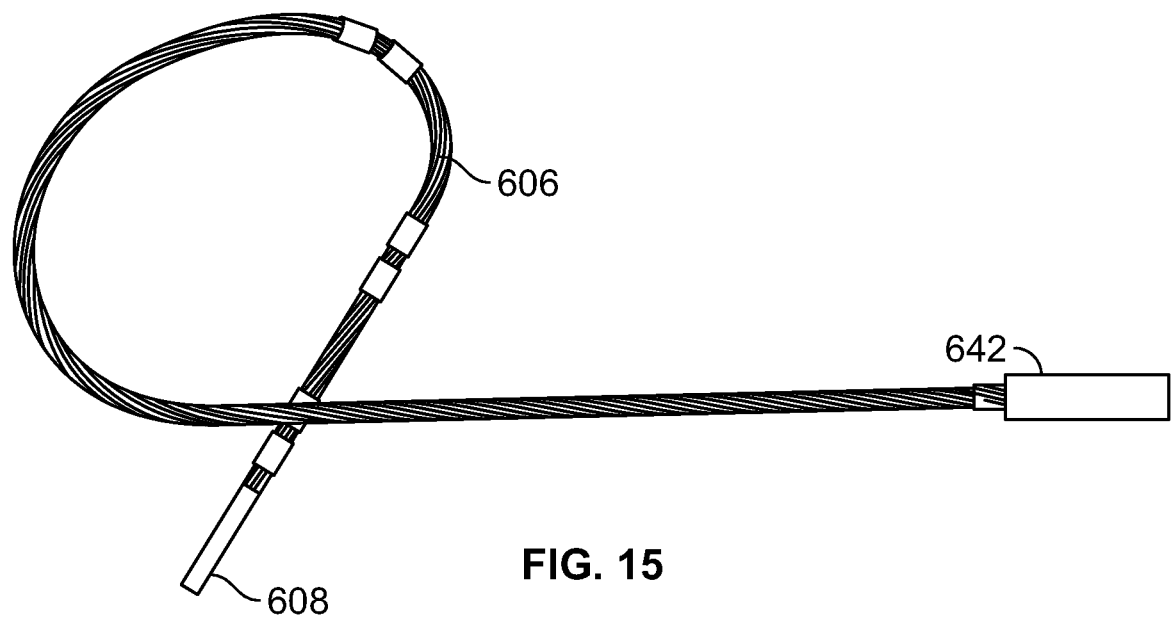

With reference to FIGS. 14-15, a catheter 608 is shown being deployed from an outer sheath 642. Initially, catheter distal section 606 is disposed within a lumen of external sheath 642, and prohibited from assuming its preset shape. The distal section 606 and external sheath 642 are moved axially relative to one another. For example, the catheter may be ejected from the sheath. Once the catheter is free from constraint, it assumes the preset shape as shown in FIG. 15.

Mechanical core assembly biases the shape of the catheter distal section 608, forcing the energy delivering elements into a curvilinear shape. In embodiments, the catheter shape is adapted to create lesions in the right atrium useful in treating atrial flutter. The shape shown in FIG. 15, for example, is a single loop or elliptical shape which has curvature to match target zones of tissue in the right atrium useful in treating atrial flutter. Additional apparatus and methods for treating atrial flutter are described in commonly assigned U.S. Patent Application No. 61/981,110, filed Apr. 17, 2014, now International Patent Application No. PCT/US2015/024778, filed Oct. 21, 2015 entitled "ENDOVASCULAR NEAR CRITICAL FLUID BASED CRYOABLATION CATHETER HAVING PLURALITY OF PREFORMED TREATMENT SHAPES," the contents of both of which are incorporated herein by reference in their entireties for all purposes.

Cryogen Flow Manifold

Figure 16:
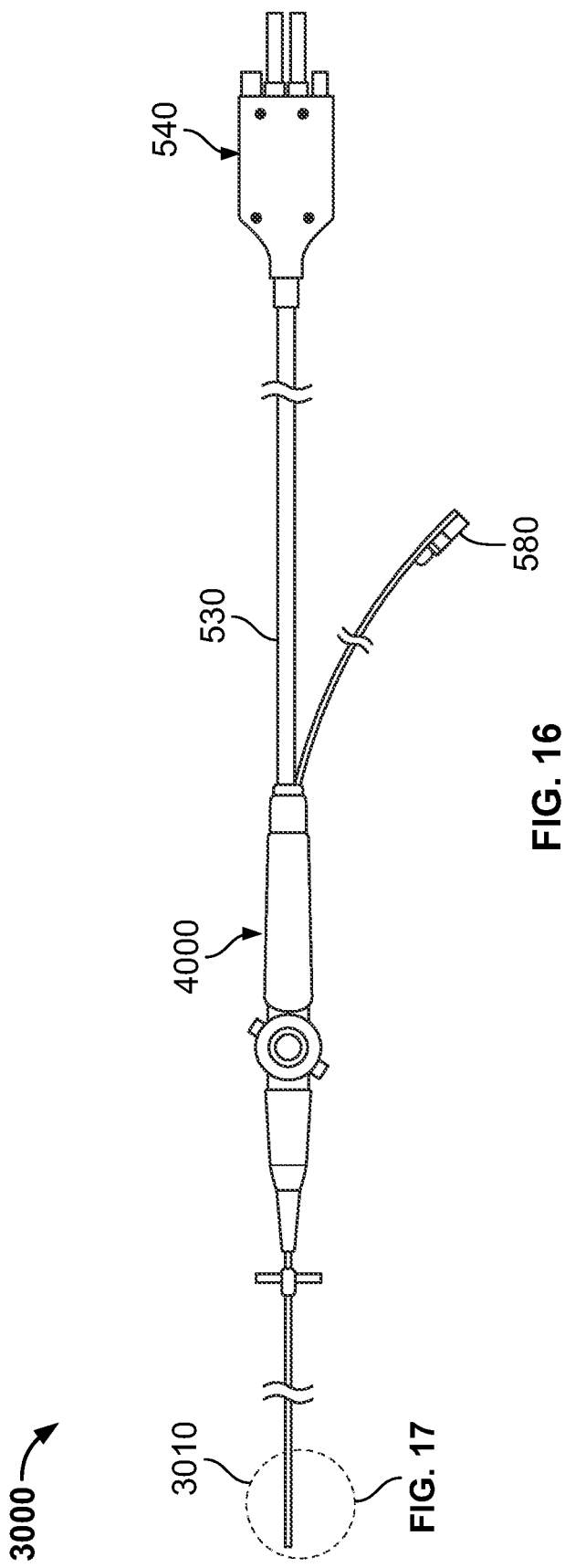
FIG. 16 is a side view of another embodiment of a cryoablation catheter.

FIG. 16 shows a cryoablation catheter 3000 according to another embodiment of the invention including an elongate shaft 3010, a handle 4000, and an umbilical cord 530. The proximal end of the umbilical cord 530 terminates in connector 540, which can be inserted into a receptacle port such as receptable port 560 on console 550 as described above in connection with FIG. 11.

The catheter 3000 is also shown having electrical connector 580. Electrical connector 580 may be coupled to an EP recording system for analyzing electrical information detected in the distal treatment section as described above in connection with FIG. 11.

Figure 17:
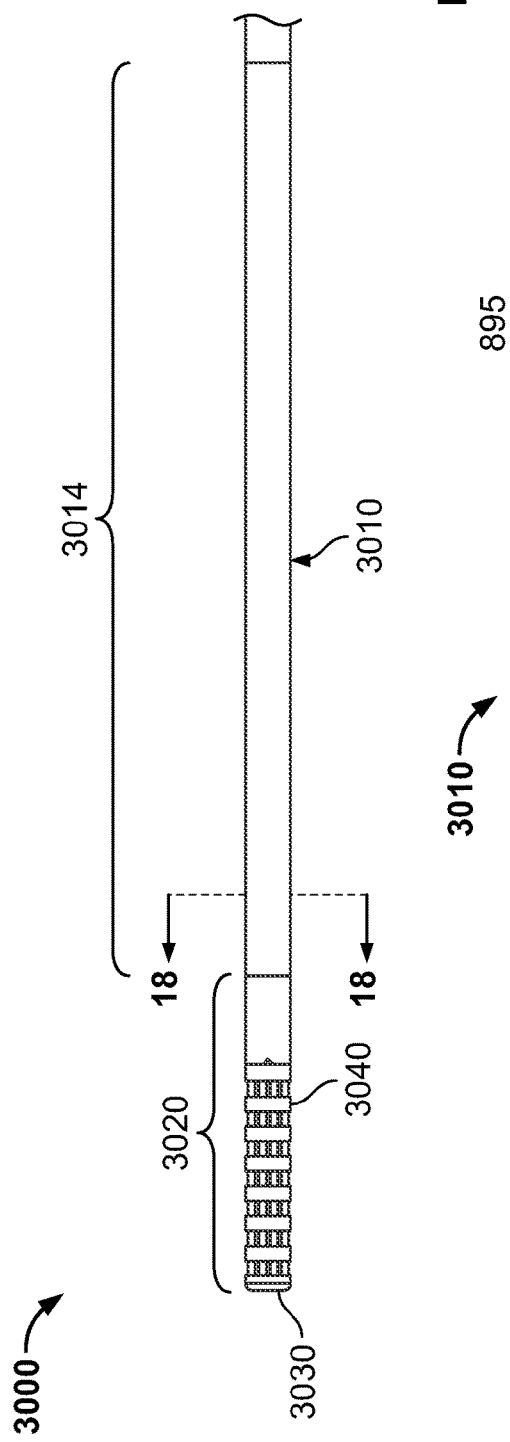
FIG. 17 is an enlarged view of a portion of the catheter shown in 16.

FIG. 17 is an enlarged view of the distal section of the ablation catheter 3000 shown in FIG. 16. In the embodiment shown in FIG. 17, the ablation catheter 3000 has an elongate shaft 3010 comprising a distal ablation portion 3020 and a distal tip 3030. Proximal region of the shaft may be coupled to the handle 4000 for manipulation of the catheter and selectively bending the catheter shaft as described further herein in connection with FIGS. 24-27.

In embodiments, the flexibility of the shaft may vary along its length. For example, in embodiments, a proximal or first shaft portion may be flexible, semi-flexible, semi-rigid or rigid. In some embodiments, a first or proximal shaft portion is less flexible than the shaft intermediate portion, however, the first shaft portion will still be flexible such that it can be delivered through the vasculature/venous system of the body to the target tissue.

The ablation catheter shown in FIG. 17 also includes a plurality of electrodes 3040 axially spaced along the distal ablation portion 3020 that may be used to detect electrical activity in the target tissue in order to evaluate or verify continuous contact of the distal ablation portion with the target tissue as described in commonly assigned International Patent Application No. PCT/US16/51954, entitled "TISSUE CONTACT VERIFICATION SYSTEM", filed Sep. 15, 2016 by Alexei Babkin, et al., the entire contents of which are incorporated herein by reference for all purposes. In some embodiments, electrodes may be included on the distal ablation tip 3030 or the ablation tip 3030 itself can act as an electrode.

Figure 18:
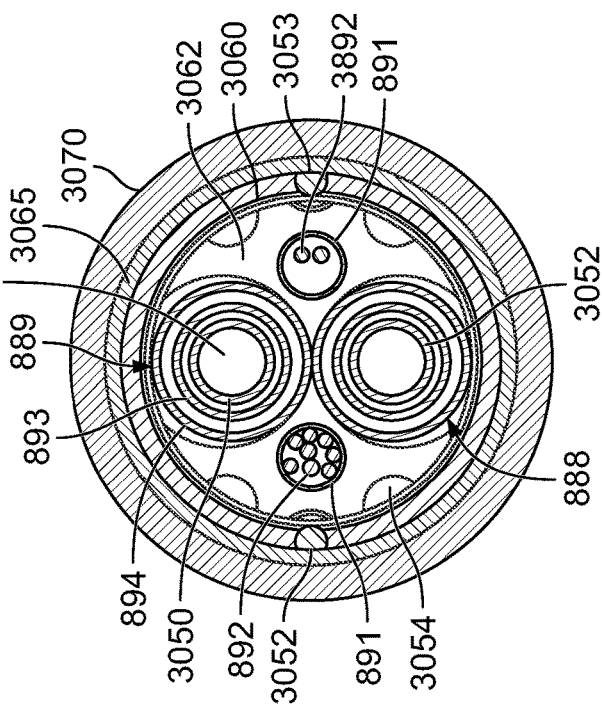
FIG. 18 is a cross sectional view of the catheter shown in FIG. 17 taken along line 18-18 in FIG. 17.

With reference to FIG. 18, a cross-sectional view of the ablation catheter 3000 taken along line 18-18 of FIG. 17 is shown. The ablation shaft 3010 includes multilayer cryogen delivery tubes/lumens 888 for transporting the cryogen to the distal ablation portion 3020 and multilayer cryogen return tubes/lumens 889 for transporting the cryogen away from the distal ablation portion. Cryogen transport tubes 888/889 are fluidly coupled with distal section entry and exit ports 3050, 3052 to circulate cryogen through the distal ablation cryogen manifold, described further herein.

Also shown are a plurality of service tubes/lumens 891 that may include catheter electrode wires 892, thermocouple wires 3892, or any other elements that may be desired.

The cross section FIG. 18 also shows a number of optional elements for manipulating the catheter shape, particularly one or more control wires 3052, 3053, open directional-biasing lumens 3054, and pull ring 3060 are arranged and operable to cause bidirectional deflection. These features may be coupled with a handle to selectively bend the distal section of the catheter as described herein.

FIG. 18 also shows one or more outer tubular sheaths and thermally insulating members 3065, 3070. Preferably, the outer diameter of the distal section is substantially constant along its length and, with reference again to FIG. 17, has a smooth transition between the intermediate portion 3014 and the distal section 3020.

Additionally, the area or space not occupied by the working components may be filled with a material or liner 3062 to facilitate flexibility of curvature.

It is to be understood that although FIG. 18 depicts one (1) multilayer cryogen delivery tube 888, one (1) multilayer cryogen return tubes 889 and two (2) service tubes/lumens 891, the embodiments of the invention are not intended to be so limited and may include any number of multilayer cryogen delivery tubes 888, multilayer cryogen return tubes 889 and service tubes/lumens 891 depending on the desired ablating power of the catheter or the condition that the catheter will be used to treat. Additionally, while FIG. 18 depicts a certain configuration of the multilayer cryogen delivery tubes 888, the multilayer cryogen return tubes 889 and the service tubes/lumens 891, specifically that pairs of multilayer cryogen delivery tubes 888 and multilayer cryogen return tubes 889 are located adjacent to one another and the service tubes/lumens 891 are separated, the embodiments of the invention are not intended to be so limited and may include any number of different configurations for the multilayer cryogen delivery tubes 888, the multilayer cryogen return tubes 889 and the service channels/tubes 891.

Figure 19:
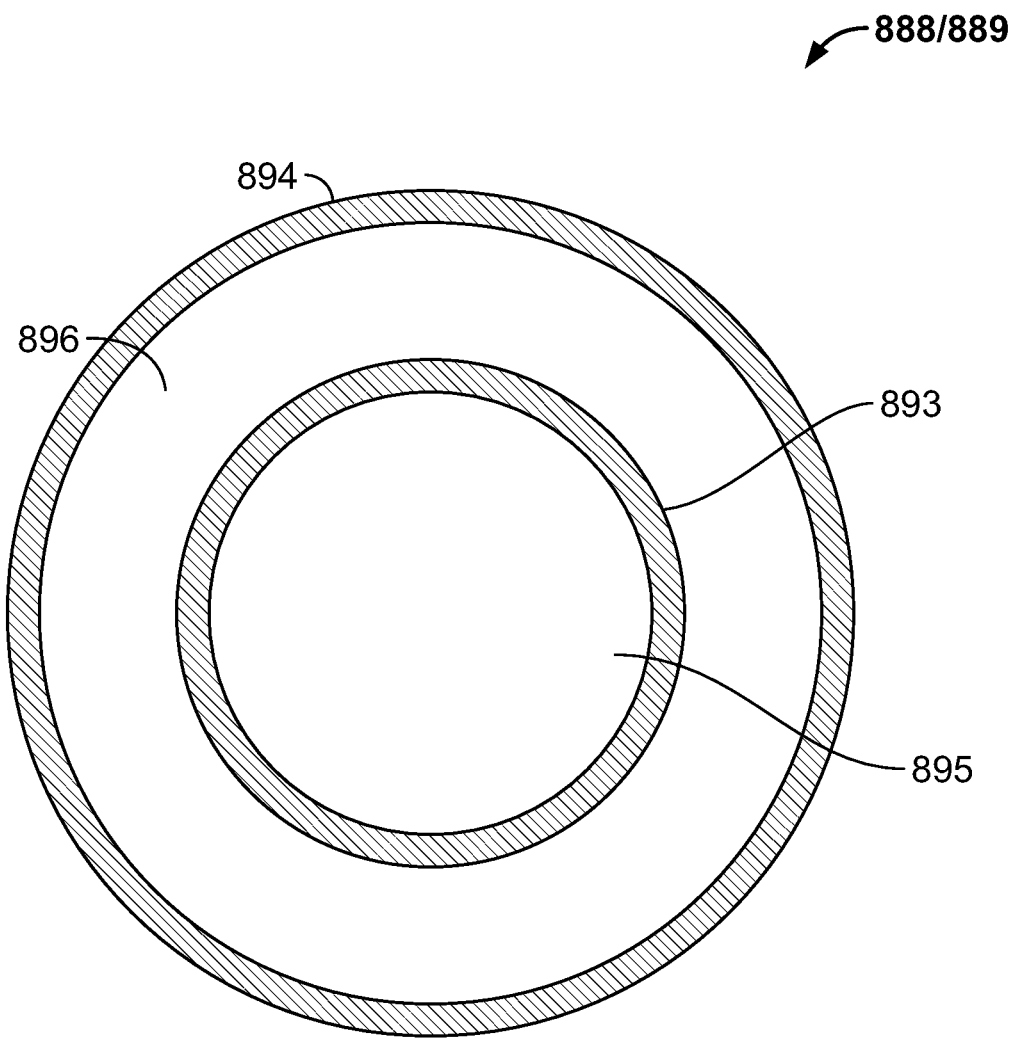
FIG. 19 is an enlarged view of one of the multi-layered cryogen delivery/return tubes shown in FIG. 18.

FIG. 19 shows an enlarged cross-sectional view of the multilayer cryogen delivery tubes 888 and multilayer cryogen return tubes 889 of FIG. 18. The first or inner tube 893 is shown coaxially surrounded by a second or outer tube 894. The lumen 895 of the inner tube 893 is designed to receive the flow of cryogen. The inner tube 893 and outer tube 894 are arranged such that a space or gap 896 is created between the exterior surface of the inner tube 893 and the interior surface of the outer tube 894. This gap 896 may be evacuated, filled with gas or air, or is capable of being filled with a thermally conductive media as described herein. In some embodiments, the gap 896 has an annular shape. All of the multilayer cryogen delivery tubes 888 as well as the multilayer cryogen return tubes 889 can have a similar tube within a tube construction.

In the event of a leak of the cryogen flowing through lumen 895 or breach of the inner tube 893 during use, the leaking cryogen is contained within the gap 896 between the inner tube 893 and the outer tube 894. This tube within a tube construction adds an additional safety element to the device as any leaking fluid/cryogen is contained within the catheter and is prevented from entering the patient. In some embodiments, a pressure sensor/device or gauge may be incorporated to monitor the pressure in the gap 896. Therefore, if fluid/cryogen breaches the inner tube 893 and leaks into the gap 896, the pressure in the gap 896 will increase. Should a change in pressure occur above a threshold limit, the system can be programmed to (a) halt ablation thereby preventing potential harm to a patient and/or (b) notify the surgeon of this change in pressure.

The inner tubes 893 may be fabricated and made from materials as described herein in connection with other flexible tubes for transporting the cryogen/cooling fluid. The outer tubes 894 may also be manufactured from a flexible material to enable elastic deflection of the flexible shaft portion and the distal ablation portion 3020 of the ablation catheter 3000 to allow these portions to transform their shapes as disclosed herein. In some embodiments, the outer tube 894 is not inflatable, distensible nor expandable such that its size and shape remain substantially unaffected by the presence of the thermally conductive media contained therein. Non-limiting exemplary materials for the outer tube 894 include polymers and metals or alloys. An example of an outer tube 894 material is polyimide.

The diameter of the distal ablation portion 3020 may vary. In some embodiments, the outer diameter of the distal ablation portion ranges from about 1-3 mm, and is preferably about 2 mm.

Figure 20:
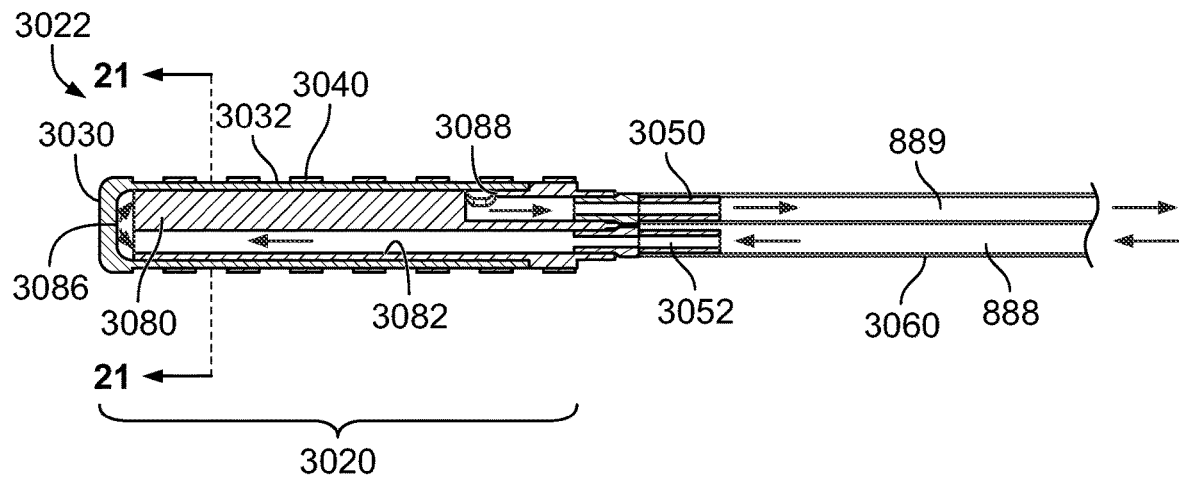
FIG. 20 is a lengthwise sectional view of the distal region of the catheter shown in FIG. 17.

FIG. 20 is a lengthwise sectional view of the distal ablation region 3020 of the catheter shown in FIG. 17 with one or more exterior components removed for facilitating understanding of the invention. In the embodiment shown in FIG. 20, the distal ablation region 3020 has a cryogen manifold assembly 3022 comprising a tubular shaped sleeve 3032 and a body 3080 inserted within the sleeve, and arranged together to define a plurality of small fluid pathways in spaces between the sleeve and the insert, discussed further herein.

Cryogen delivery tube 888 is shown fluidly connected to entry port 3052 of insert 3080 and cryogen return tube 889 is shown fluidly connected to exit port 3050 of insert 3080. In operation, after the distal ablation section is placed in contact with a target tissue, a cryogen is circulated through the cryogen manifold 3022 from the ingress port 3052, along insert channel 3082, into tip space 3086 where the fluid changes direction, and is distributed to the multiple discrete fluid flowpaths arranged about the circumference or perimeter of the insert, and ultimately collected by egress port 3088 and into return transport tube 889. As the cryogen is circulated through the cryogen manifold, heat is transferred from the target tissue to the cryogen, thereby cooling the tissue and forming the lesion.

Figure 21:
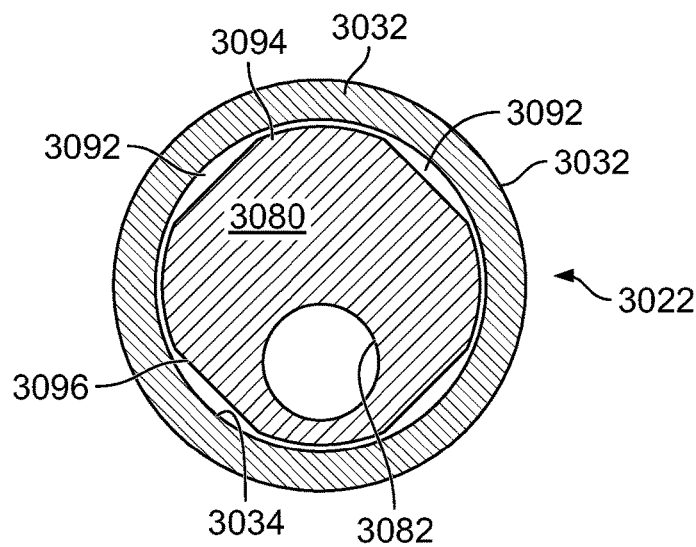
FIG. 21 is a cross sectional view of the catheter shown in FIG. 20 taken along line 21-21 in FIG. 20.

FIG. 21 is an enlarged cross sectional view of the cryogen manifold assembly 3022 shown in FIG. 20 taken along line 21-21. Body 3080 is shown having an octagon-shaped cross sectional shape and is inserted within the circular-shaped lumen 3034 of sleeve 3032. Four fluid pathways 3092 are defined between the flat sides 3096 and the inner surface 3034 of the sleeve. The flats 3096 are separated by low-flow (bowed) sections 3094 of the body which extend to, or nearly match the inner diameter (ID) of the sleeve. In embodiments, an effective diameter of the fluid pathway 3092, namely, the distance between the sleeve and the body along the flats 3096 ranges from 0.05 to 1 mm. The distance between the sleeve and the body along the low-flow sections 3094 is less than that of fluid pathways, and can range from 0 to 0.30 mm, and more preferably ranges from 0.05 to 0.15 mm, and in some low flow regions, can be zero or gapless.

Figure 22:
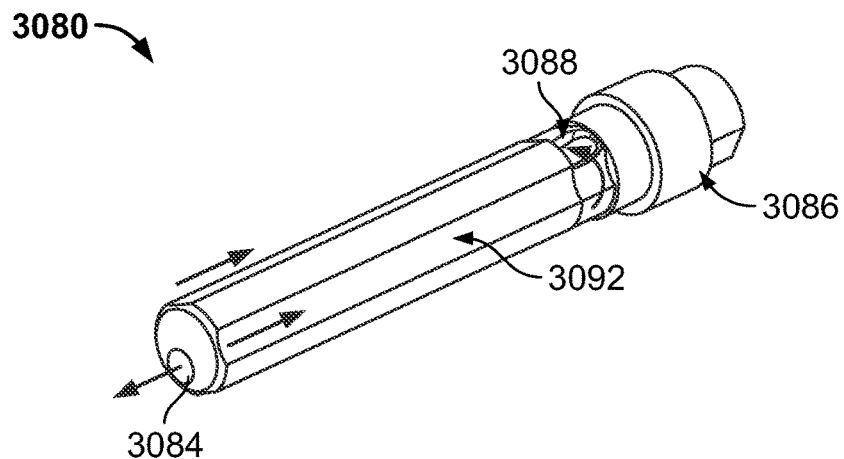
FIG. 22 is a perspective view of the insert shown in FIG. 20.

FIG. 22 is a perspective view of the insert shown in FIGS. 20-21 with the sleeve removed for facilitating understanding of the invention. The embodiment illustrated in FIG. 22 has arrows indicating the direction of fluid flow. Particularly, the fluid is shown exiting central channel outlet 3084, moving along fluid pathways 3092, and collected in egress port 3088. As stated above, collection port 3088 communicates the fluid to return tube 889 (not shown in FIG. 22). The insert body 3080 shown in FIG. 22 also includes a hub portion 3086, which is adapted to mate with exterior outer sheath 3070 of the catheter shaft (not shown in FIG. 22).

Figure 23:
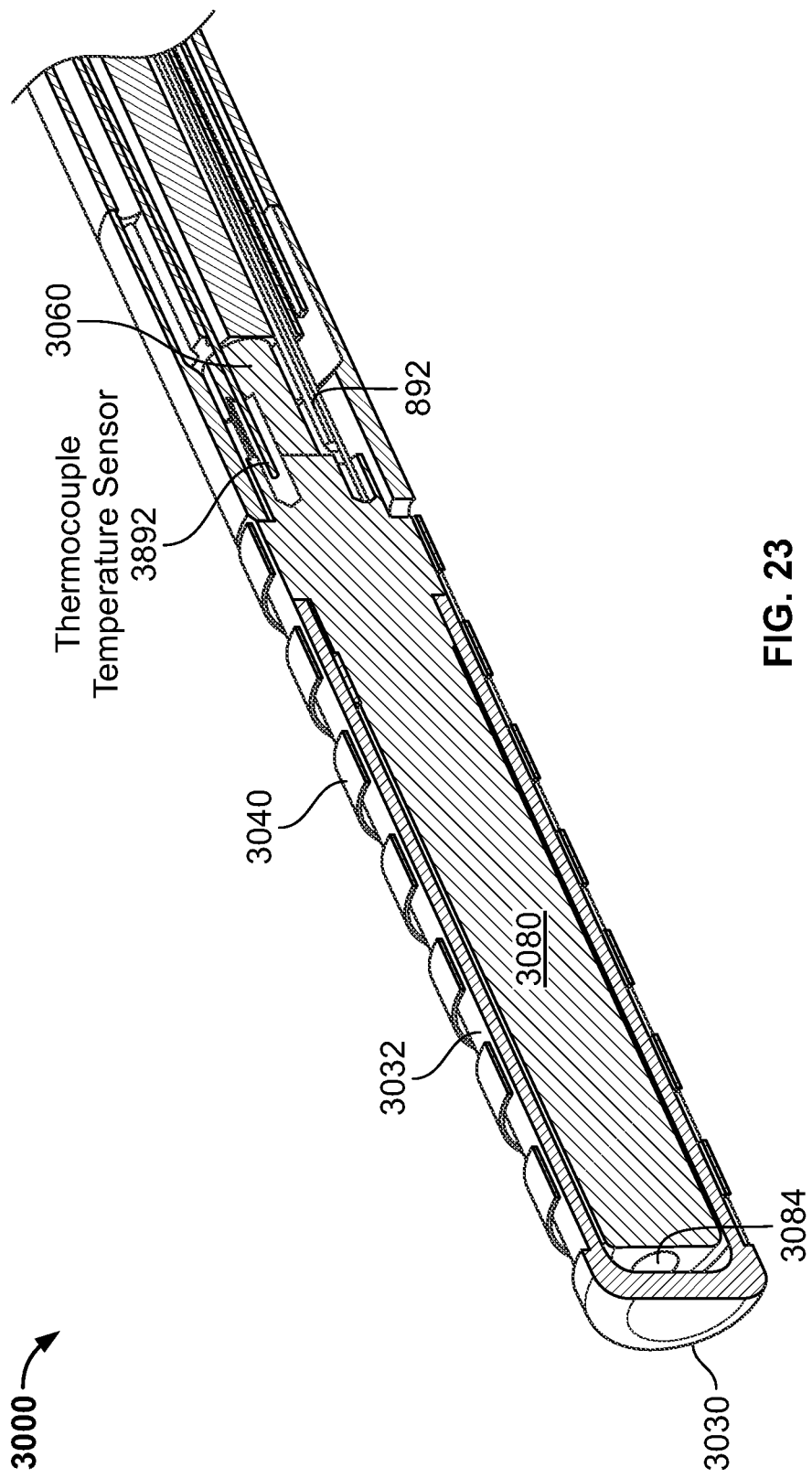
FIG. 23 is another lengthwise sectional view of the distal region of the catheter shown in FIG. 24.

FIG. 23 is another lengthwise sectional view of the distal region of the catheter shown in FIG. 17. FIG. 23 illustrates the arrangement of thermocouple wires 3892 and electrode wires 892 with the cryogen manifold assembly. Thermocouple wires 3892 are nested in a cavity in thermal communication with the insert body 3080. As described herein, measuring temperature of the catheter ablation region can be used to control the amount of power to the catheter. Each electrode wire 892 extends and is connected with a separate ring electrode 3040. Optionally, the spacing between the electrode rings is filled with an electrically insulative and semi-thermally conductive material. An example of an electrically insulative yet semi-thermally conductive material is a thermoplastic elastomer filled with ceramic (e.g. polyether block amide filled with boron nitride).

As described herein, the electrodes 3040 can be used during the procedure to determine tissue contact and location information, as well as gauge the effect of the treatment. Tip 3030 may also be covered with an electrically insulative yet thermally conductive material. An example of an electrically insulative yet thermally conductive material is a thermoplastic elastomer filled with ceramic (e.g. polyether block amide filled with boron nitride). The electrical insulation prevents cross talk between the electrodes, and provides a more accurate signal landscape from the tissue.

Although the insert body 3080 is generally shown having an octagon-type cross section, the invention is not intended to be so limited except as recited in the appended claims. The cross sectional shape of the insert body may vary widely. Exemplary cross sectional shapes include any type of polygon such as, without limitation, triangle, quadrilateral, pentagon, hexagon, decagon, nonagon, hectogon, as well as other shapes whether symmetric or not which differ from the shape of the sleeve lumen. Each side of the polygon may be straight or sides may be modified to extend to the inner surface of the sleeve as described above with reference to edge 3094 shown in FIG. 21. In preferred embodiments, sides of the polygon alternate between straight and curved or outwardly bowed edges. Without intending to being bound to theory, the axial cutouts along the insert body, defining the various discrete fluid pathways, serve to create turbulent type flow, and increase the efficiency of heat transfer.

The materials of the cryogen flow manifold may vary. In embodiments, the insert body and outer sleeve are made of thermally conducting materials such as aluminum or steel. The components may be coupled together with adhesives, press fits, and other bonding techniques as is known to those of ordinary skill in the art.

Handle Actuator for Bidirectional Shaft Bending

Figure 24:
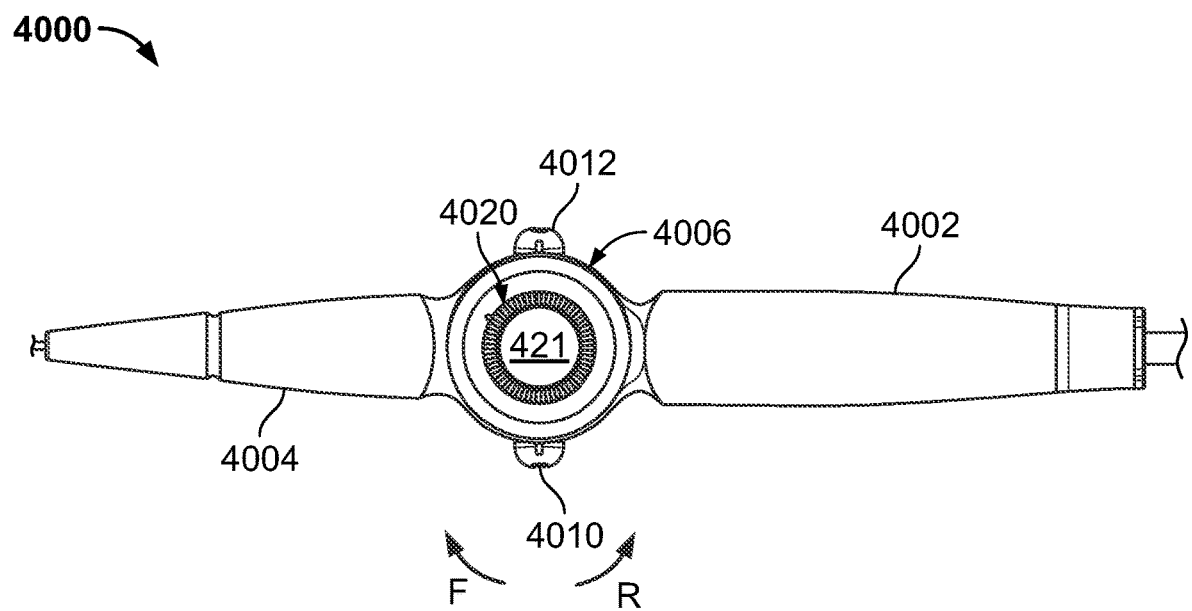
FIG. 24 shows a side view of a handle for an ablation catheter, according to an embodiment of the invention.

FIG. 24 shows a side view of the handle 4000 for an ablation catheter, according to an embodiment of the invention. The handle 4000 shown in FIG. 24 includes proximal grip 4002, a distal grip 4004, and an actuator assembly 4006 located between the proximal and distal grips. Collectively, the handle has an ergonomic, slender, dagger-like appearance.

Figure 25:
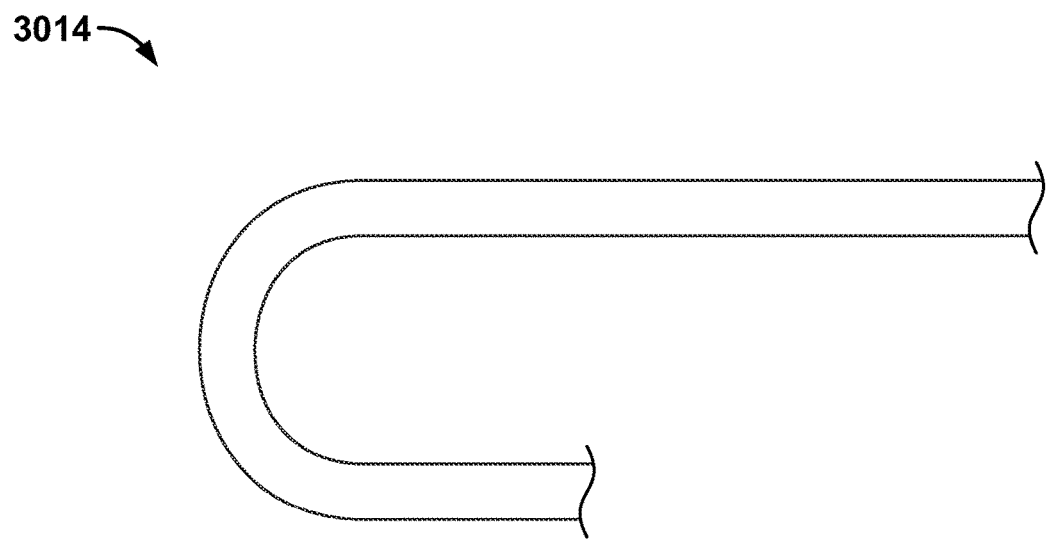
FIG. 25 illustrates a 180 degree bend of the catheter shaft upon activation of the handle in accordance with an embodiment of the invention.

The actuator assembly 4006 has two levers or finger holds 4010, 4012 which can rotate in either direction (R or F), causing the elongate shaft to bend to a desired angle based on the level of rotation of the finger holds. In embodiments, the bend of the shaft is bidirectional and up to (or more than) 180 degrees as shown in FIG. 25. Once the physician has reached or hit the desired level of bend (perhaps by visualizing the shaft in fluoroscopy or another imaging technique), brake 4020 may be set to hold the bend at the desired level. In the embodiment shown in FIG. 24, the brake 4020 is a variable friction brake and set by rotating cover 4021 clockwise until finger tight, as described further herein.

Figure 26:
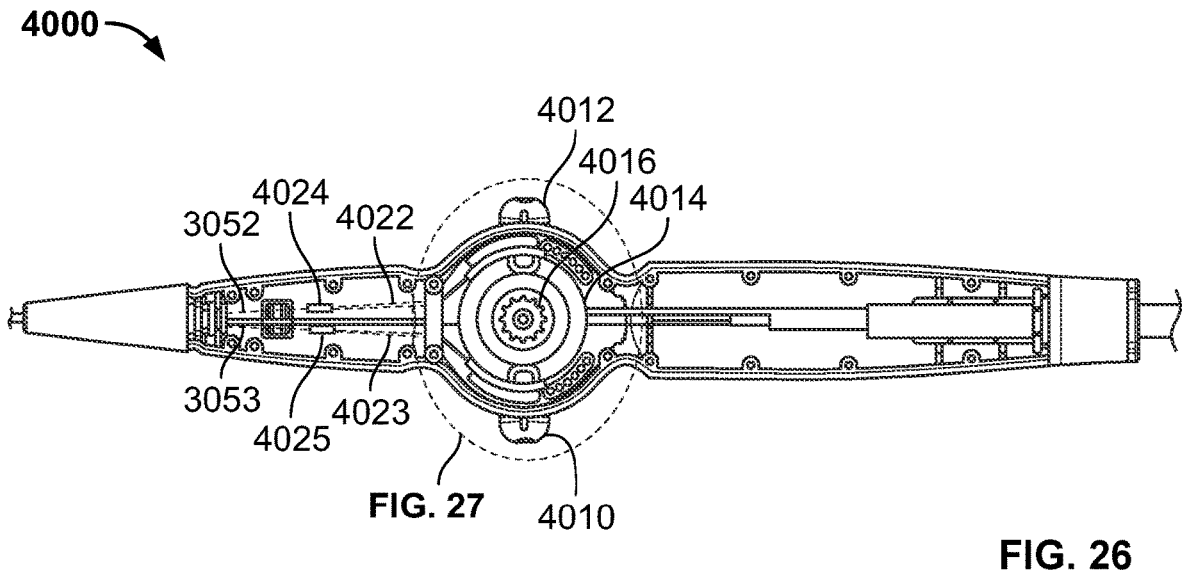
FIG. 26 shows a side view of the handle shown in FIG. 24 with the exterior removed.
Figure 27:
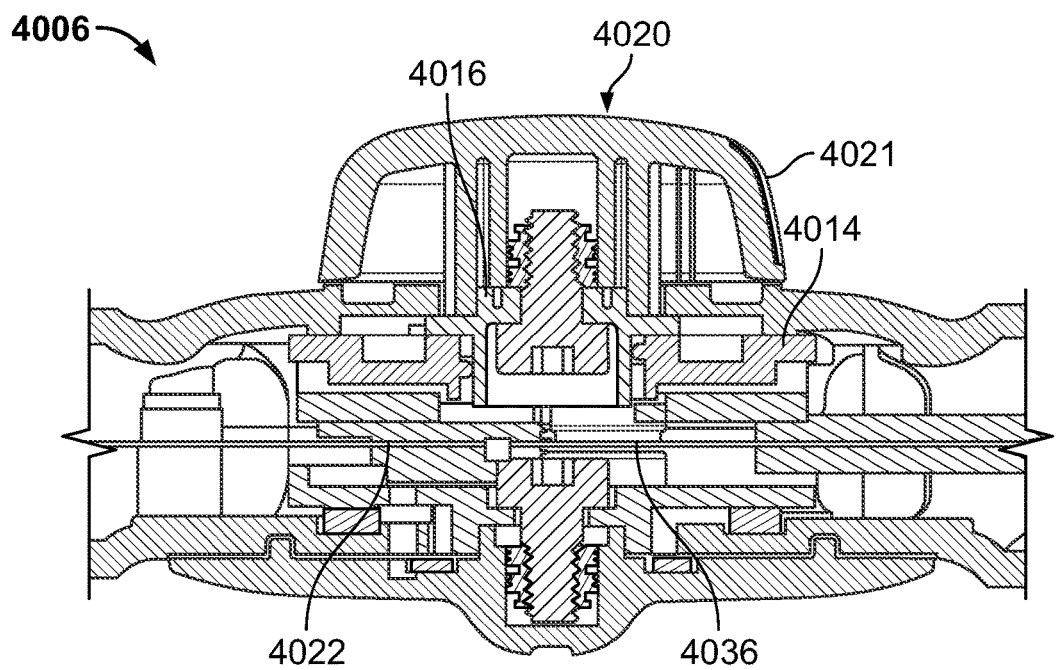
FIG. 27 shows a cross section of a portion of the handle shown in FIG. 26.

With reference to FIGS. 26-27, the handle 4000 is shown with its exterior removed to facilitate understanding of additional details of embodiments of the invention. More specifically, the cooperation of the control wires 3052, 3053 and the actuator assembly are visible. Control wires 3052, 3053, which run to the distal ablation section of the catheter and are coupled to pull ring, as described above, are mechanically coupled to pulley member 4036. Optionally, and as shown in FIGS. 32A and 32B, the control wires are fastened to flexible filaments 4022, 4023 (e.g., suture, nylon, etc.) by ferrule couplers 4024, 4025. Consequently, when the pulley is rotated by manipulation of finger holds or levers 4010, 4012, the control wire and ultimately the distal section of the catheter shaft is bent to the level that the finger holds are manipulated. In the embodiment shown in FIGS. 32A and 32B, the motion arising from the actuator mechanism 4006 is bidirectional. That is, the catheter shaft is forced to bend only one direction (or the opposite direction) from its axis upon actuation of the actuator assembly 4006. However, additional degrees of freedom are available to the physician by manually rotating the entire handle 4000 about its longitudinal axis.

As described herein, the catheter is operable to set or lock the catheter bend at a desired angle by frictional force. In the embodiment shown in FIGS. 32A, 32B, brake assembly 4020 includes knob or button 4021 in threaded engagement via member 4016 with pad 4014 which compresses pulley assembly 4036 as knob is turned. Once the knob 4021 is snug or finger tight, the pulley and finger levers 4010,4012 may not be further manipulated due to the frictional force between the plate 4014 and the pulley and arms 4036.

The brake may be released by unscrewing knob 4021, which serves to loosen or release pulley. Once the pulley is free, the finger levers may be rotated forward or back as desired to bend the catheter shaft a corresponding level. It should be understood that although specific types of components are shown and described in the handle, actuator, and brake assemblies, the invention is not intended to be so limited except where specifically recited in the claims.

Applications

Embodiments of the cryoablation apparatus (catheters, probes, etc.) described herein have a wide range of diagnostic and therapeutic applications including, for example, endovascular-based cardiac ablation and more particularly, the endovascular-based cardiac ablation treatment of atrial fibrillation.

Figure 28:
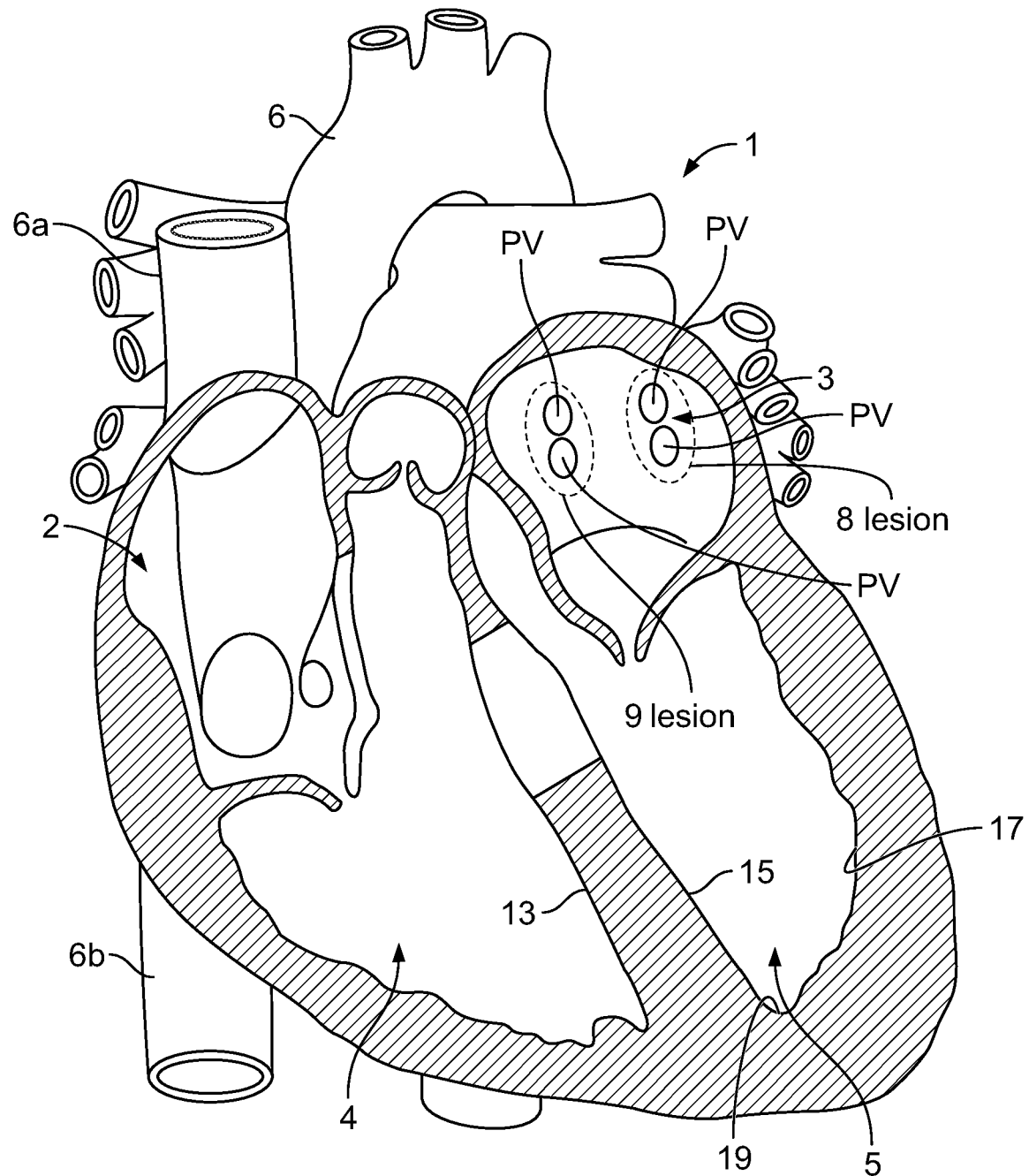
FIG. 28 is an illustration of a heart, and locations of various lesions according to an embodiment of the invention.

FIG. 28 shows examples of target ablation lesions in a pulmonary vein isolation (PVI) procedure for the treatment of atrial fibrillation.

The basic structures of the heart 1 are shown in FIG. 28 including the right atrium 2, the left atrium 3, the right ventricle 4 and the left ventricle 5. The vessels include the aorta 6 (accessed through the femoral artery), the superior vena cava 6a (accessed through the subclavian veins) and the inferior vena cava 6b (accessed through the femoral vein).

Exemplary target lesions for a PVI procedure include lesion 8 which surrounds and isolates all left pulmonary veins (PVs), and lesion 9 which surrounds and isolates all right pulmonary veins (PVs). As described further herein, the invention may include application or creation of additional lesions to increase the effectiveness of the treatment. Also, it is to be understood that although the following discussion primarily focuses on embodiments for performing PVI, the technology and procedure described herein for producing these lesions can be used to create other lesions in an around the heart and other organs such as that described in international patent application nos. PCT/US2012/047484 to Cox et al. and PCT/US2012/047487 to Cox et al. corresponding to International Publication Nos. WO2013/013098 and WO2013/013099 respectively, the contents of each of which is hereby incorporated by reference in their entirety.

Figure 29:
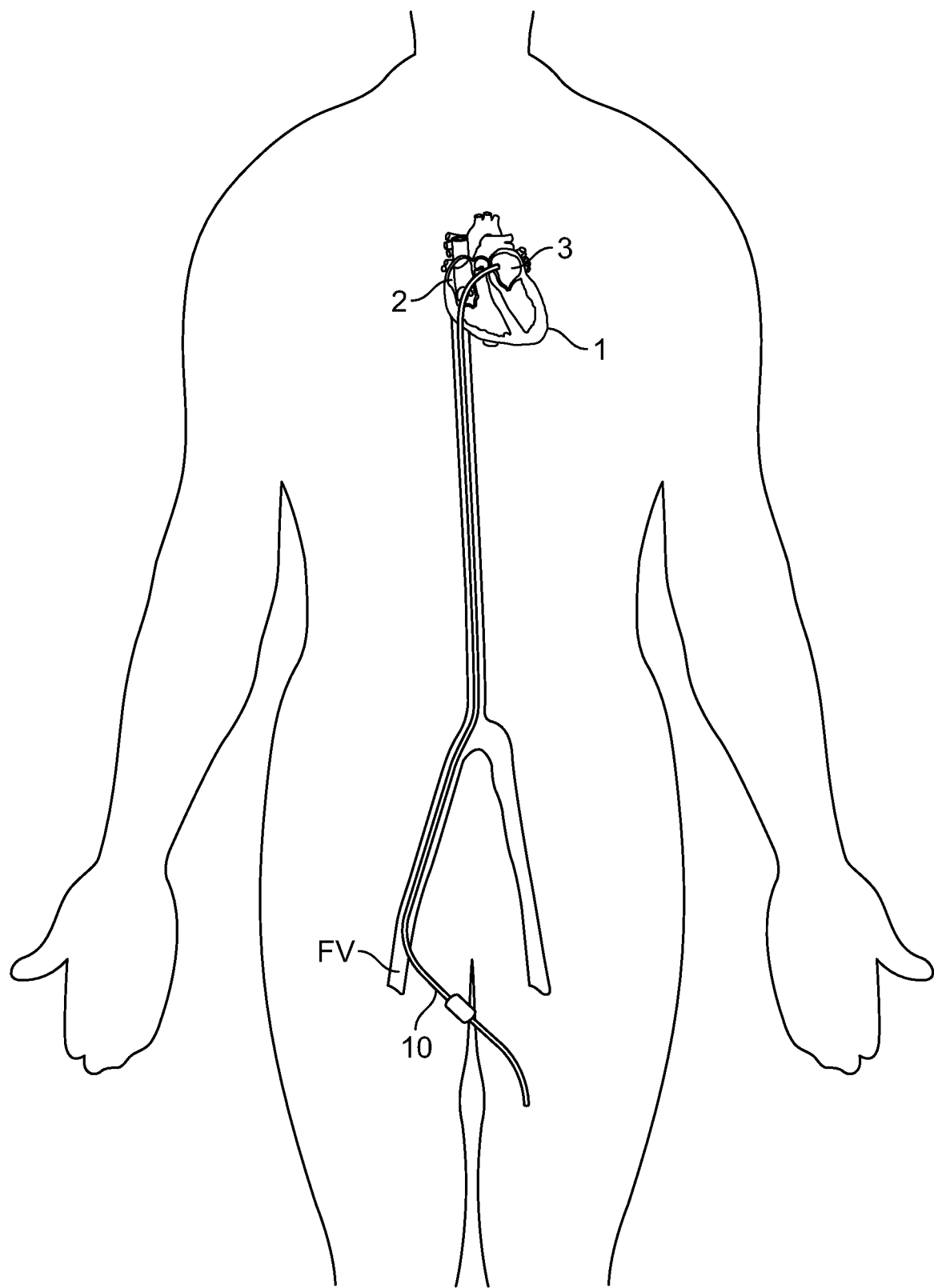
FIG. 29 is an illustration of an embodiment of endovascular catheterization to access the heart.

FIG. 29 illustrates one technique to reach the left atrium with the distal treatment section of a catheter. The procedure may be performed under conscious sedation, or general anesthetic if desired.

A peripheral vein (such as the femoral vein FV) is punctured with a needle. The puncture wound is dilated with a dilator to a size sufficient to accommodate an introducer sheath, and an introducer sheath with at least one hemostatic valve is seated within the dilated puncture wound while maintaining relative hemostasis.

With the introducer sheath in place, the guiding catheter 10 or sheath is introduced through the hemostatic valve of the introducer sheath and is advanced along the peripheral vein, into the target heart region (e.g., the vena cavae, and into the right atrium 2). Fluoroscopic imaging can be used to guide the catheter to the selected site.

Once in the right atrium 2, the distal tip of the guiding catheter is positioned against the fossa ovalis in the intraatrial septal wall. A needle or trocar is then advanced distally through the guide catheter until it punctures the fossa ovalis. A separate dilator may also be advanced with the needle through the fossa ovalis to prepare an access port through the septum for seating the guiding catheter. The guiding catheter thereafter replaces the needle across the septum and is seated in the left atrium through the fossa ovalis, thereby providing access for devices through its own inner lumen and into the left atrium.

Placement of the above tools may be carried out with guidance from one or more of the following: fluoroscopy, intracardiac pressures, transesophageal echocardiography (TEE), and intracardiac echocardiography (ICE).

FIGS. 30-33 illustrate a method for deploying a ring-shaped catheter in the left atrium and around pulmonary vein entries for treating various heart conditions such as atrial fibrillation.

Figure 30:
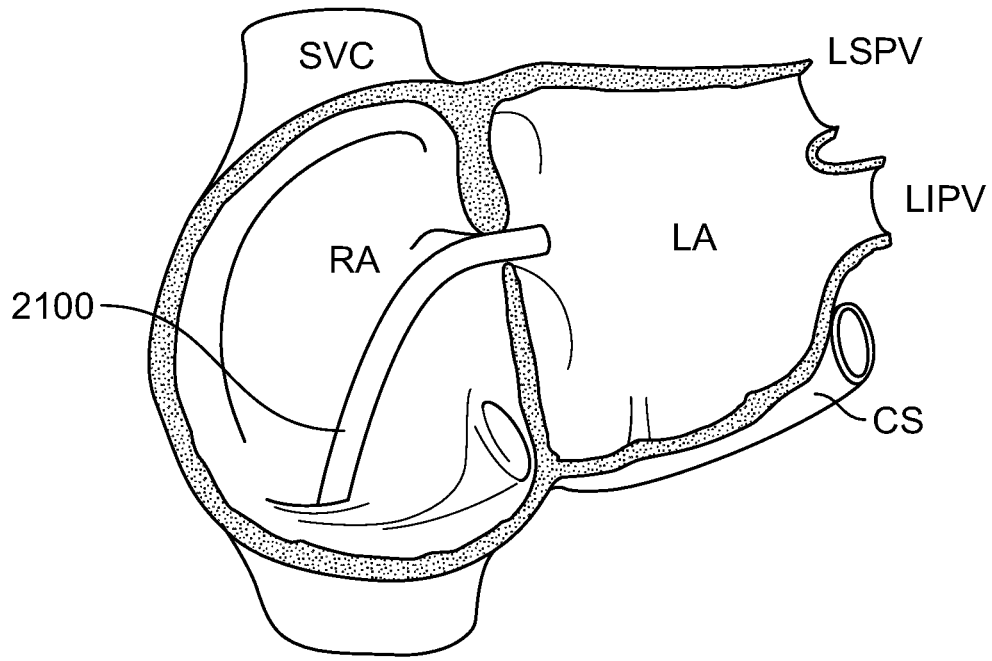
FIGS. 30-31 are illustrations of a procedure to place a distal section of a cryoablation catheter against the endocardial wall in the left atrium, circumscribing the left superior and inferior pulmonary vein entries, according to an embodiment of the invention.

With reference first to FIG. 30, a cross sectional view of the heart includes the right atrium RA 2, left atrium LA 3, left superior pulmonary vein LSPV entry, and left inferior pulmonary vein LIPV entry. Guide catheter 2100 is shown extending through the septum and into the left atrium.

Though not shown, mapping catheters may be positioned in the entry to the LSPV of the left atrium for monitoring electrical signals of the heart. The mapping catheters may be placed in other locations, such as, for example the coronary sinus (CS). Examples of mapping catheters include the WEBSTER® CS Bi-Directional Catheter and the LASSO® Catheter, both of which are manufactured by Biosense Webster Inc. (Diamond Bar, Calif. 91765, USA). Another example of mapping and cryo-treatment system is described in US Patent Publication No. 2015/0018809 to Mihalik.

Optionally, an esophageal warming balloon may be placed in the esophagus to mitigate collateral damage arising from creating the lesions. An esophageal warming balloon prevents the cold temperatures from reaching the inner layer of cells of the esophagus, and can prevent formation of, e.g., an atrio-esophageal fistula. An example of a suitable esophageal warming balloon apparatus that may be used is described in commonly assigned U.S. patent application Ser. No. 15/028,927, entitled "ENDOESOPHAGEAL BALLOON CATHETER, SYSTEM, AND RELATED METHOD," filed Oct. 12, 2014 by Alexei Babkin, et al., the contents of which is incorporated herein by reference in its entirety for all purposes.

Figure 31:
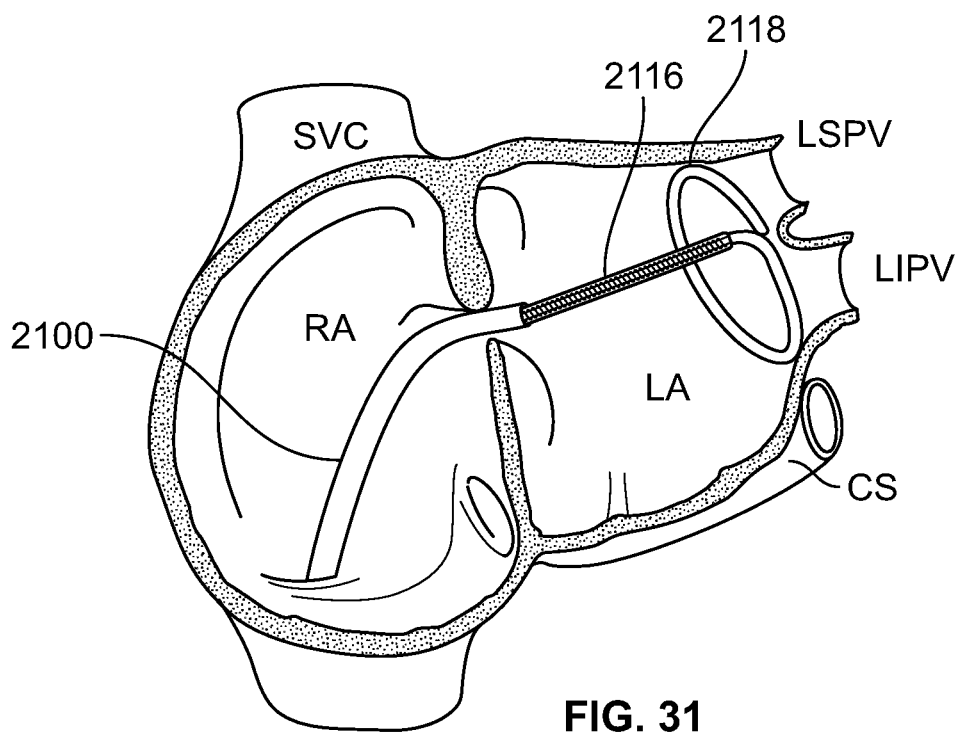

FIG. 31 illustrates a distal section of the cryoablation catheter 2116 advanced through the guide sheath 2100. The energy element 2118 is shown having a circular shape formed as disclosed and described herein and urged against the endocardium. As described herein the shape may be adjusted to make continuous contact with the tissue, and to form an elliptical or circular-shaped continuous lesion (such as lesion 8 shown in FIG. 28) which encloses all the left PV entries.

In embodiments the shape is modified by reducing the diameter of loop, articulating the intermediate section of the shaft, and rotating or steering the catheter distal section. Collectively, the steps of deployment, diameter control, steering and articulation can place the entire circumference of the loop in continuous contact with the endocardium tissue. When energy is applied to the distal treatment section such as, for example, by flowing a cryogen through the distal treatment section, a continuous elongate ring-shaped lesion (frozen tissue) is formed such as the lesion 8 shown in FIG. 28, enclosing all left pulmonary vein entries.

Figure 32:
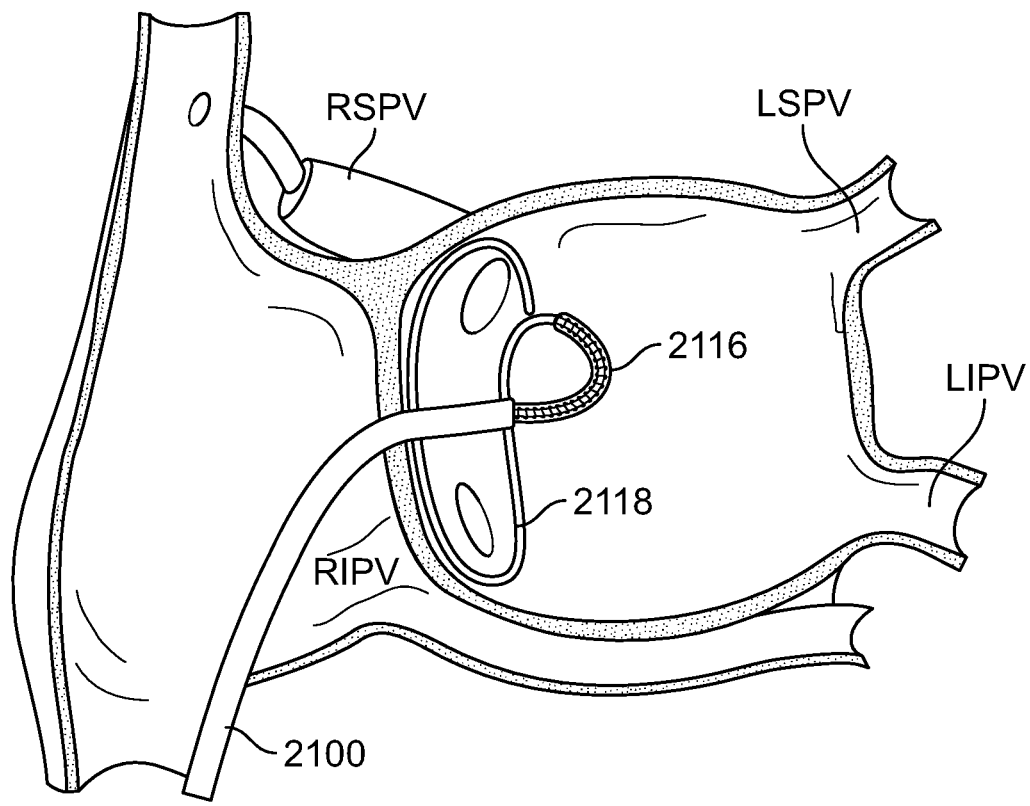
FIGS. 32-33 are illustrations of a procedure to place a distal section of a cryoablation catheter against the endocardial wall in the left atrium, circumscribing the right superior and inferior pulmonary vein entries, according to an embodiment of the invention.

FIG. 32 illustrates formation of a ring-shaped lesion around the right superior pulmonary vein (RSPV) entries and the right inferior pulmonary vein (RLPV) entries such as, for example, lesion 9 shown in FIG. 28. In contrast to the somewhat linear (straight shot) positioning shown in FIGS. 30-31, the catheter neck region 2116 shown in FIG. 32 is deflected nearly 180 degrees to aim towards the right pulmonary veins. Energy element portion 2118 is positioned around the RSPV and RIPV entries.

FIG. 32 shows the energy element 2118 deployed in a circular shape and contacting the endocardium. As described herein the shape may be adjusted to make better contact with the tissue in order to form an elongate ring-shaped, continuous lesion that engulfs or surrounds the RSPV and RIPV entries.

A similar elongate ring-shaped, continuous lesion can be formed to surround the left superior pulmonary vein (LSPV) entries and the left inferior pulmonary vein (LIPV) entries.

Figure 33:
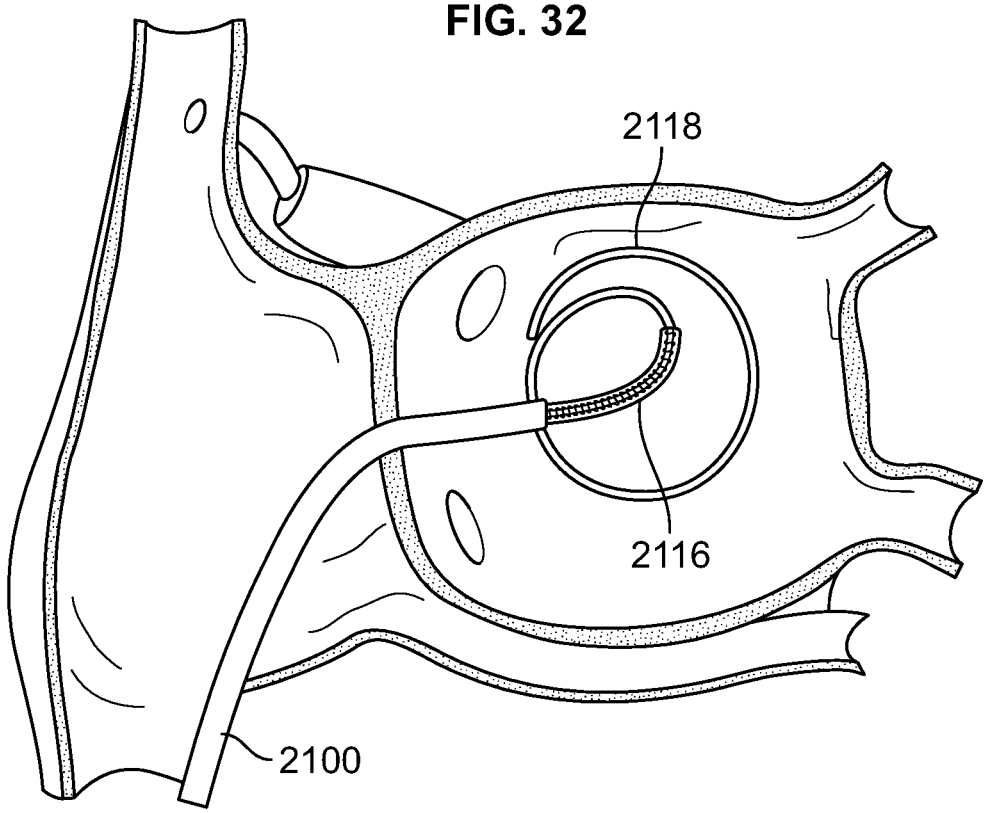

FIG. 33 shows the catheter 2116 deflected to aim towards the posterior wall of the left atrium. Energy element portion 2118 is manipulated to form a loop and urged against the posterior wall, overlapping with previously-formed right and left lesions.

Optionally, and not shown, guidewires can be advanced from the guide sheath and used to navigate the catheter treatment section into position.

The shape of the lesion and pattern may vary. In embodiments, and with reference to FIG. 34, a "box-shaped" lesion 900 is shown surrounding multiple pulmonary vein entries in a PVI procedure. The box-shaped lesion surrounds the pulmonary vein entries on both the left and right sides of the left atrium.

Figure 34:
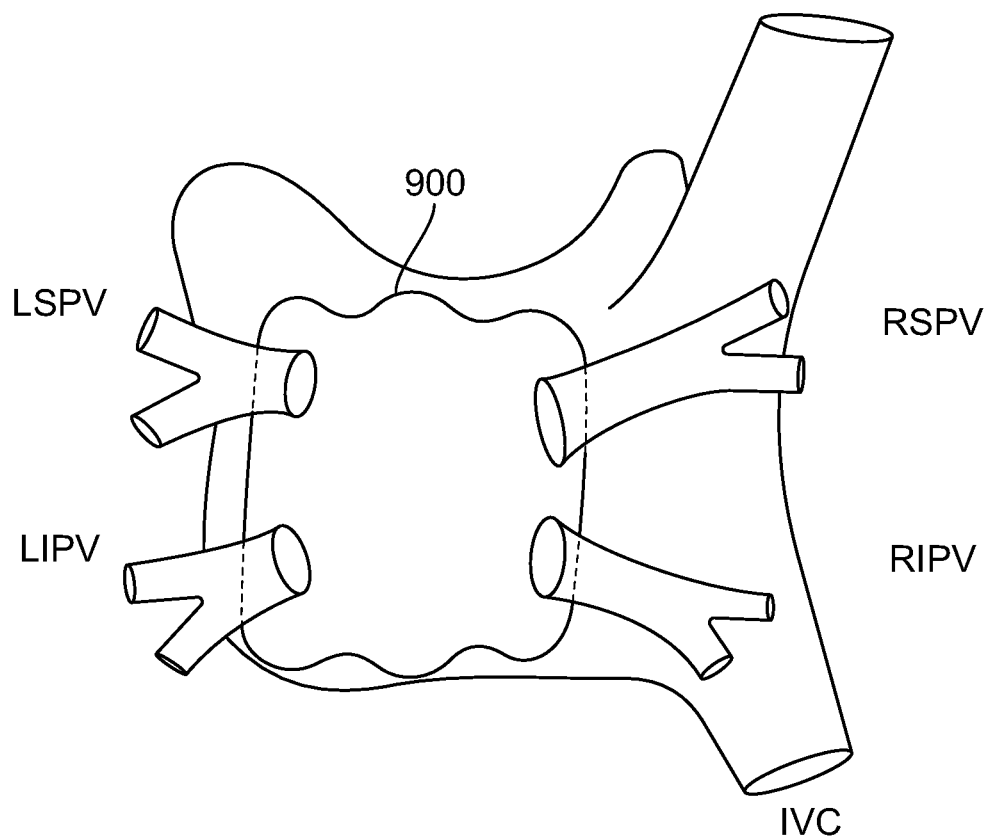
FIGS. 34-35 illustrate a method for creating a box-shaped lesion, according to an embodiment of the invention, where the figures depict the left atrium as viewed from the back of a patient.

The box-shaped lesion 900 may be formed in various ways. In some embodiments, the box-shaped lesion is formed by overlapping a combination of lesions, which can have similar or different shapes (e.g., oval, ellipse, ring, etc.) to form an overall larger continuous lesion, which may have a box-like shape 900 as shown in FIG. 34.

Figure 35:
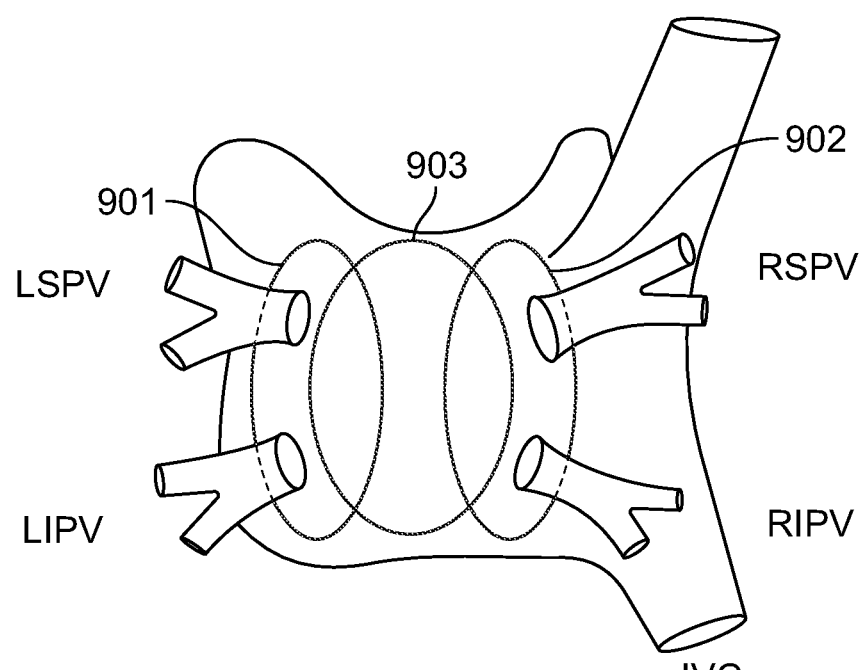
Figure 36:
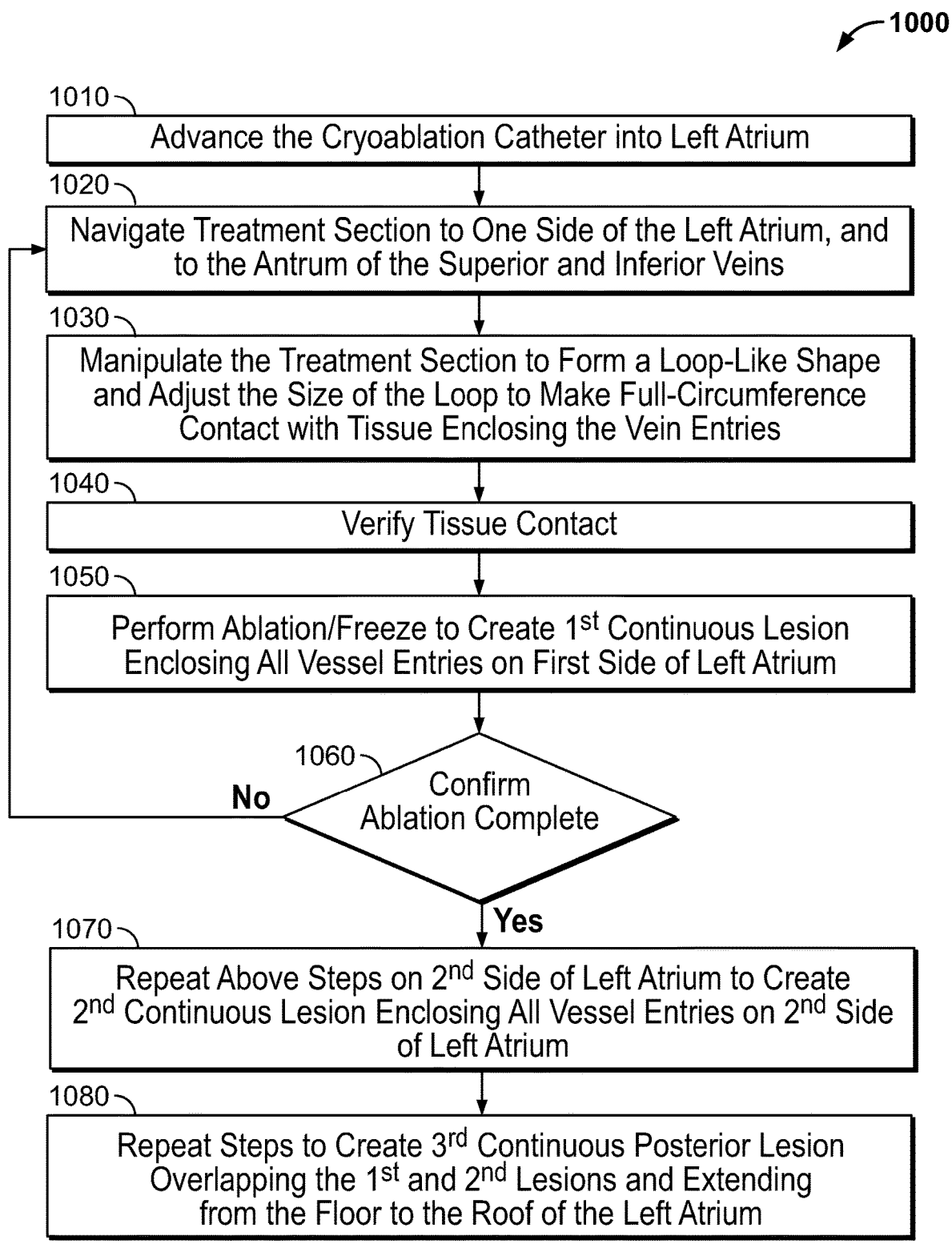
FIG. 36 is flow diagram showing a method of creating a box-shaped lesion to enclose multiple PVs in the left atrium, according to an embodiment of the invention.

With reference to the illustration shown in FIG. 35, and the corresponding flow diagram shown in FIG. 36, a method 1000 for forming a box-shaped lesion in the left atrium that encircles/encloses all pulmonary vein (RSPV, RIPV, LSPV and LIPV) entries, is described.

Step 1010 states to advance the cryoablation catheter into the left atrium, which can be performed using a guide sheath, for example.

Step 1020 states to navigate the treatment section (energy element portion 2118) of the catheter to one side of the left atrium and into the antrum of the superior and inferior pulmonary veins on that side of the atrium.

Step 1030 states to manipulate the treatment section (energy element portion 2118) of the catheter to form a loop-like shape and to adjust the size of the loop to make full circumference tissue contact with tissue to enclose the superior and inferior vein entries on that side of the atrium.

Step 1040 states to verify tissue contact. This step may be performed using, for example, electrodes mounted on the distal treatment section as disclosed and escribed in commonly assigned International Patent Application No. PCT/US16/51954, entitled "TISSUE CONTACT VERIFICATION SYSTEM", filed Sep. 15, 2016 by Alexei Babkin, et al., the entire contents of which are incorporated herein by reference for all purposes. The tissue electrocardiograms (ECGs) may be displayed using an EP recording system.

Optionally, an esophageal balloon (EBB) (as discussed above) is advanced into the esophagus in the vicinity of the heart. The EBB is inflated and a thermally conducting liquid is circulated through the balloon for the duration of the ablation treatment. As described herein, the EEB minimizes collateral damage to tissue adjacent the ablation zone by warming the tissue during the ablation cycle.

Step 1050 states to perform the ablation by freezing the tissue to create a first continuous lesion enclosing/surrounding the pulmonary vein entries on the first side of the left atrium, for example, the left side lesion 901 in FIG. 35. The duration of the tissue freeze may be up to 3 minutes or more, and generally ranges from about 1 to 3 minutes, and preferable is about 2 minutes. In embodiments, the freeze step comprises a single application of uninterrupted ablation energy.

In some embodiments, the duration of the energy application ranges from approximately 10 to 60 seconds, and sometimes is less than or equal to approximately 30 seconds.

The duration of the freeze cycle may vary. A physician or electro physiologist can elect to terminate the freeze cycle as desired (e.g., before or after the anticipated time period has passed). Examples of reasons for early termination include: a desire to reposition the catheter, a desire to improve catheter-tissue contact, or a safety concern.

Step 1060 states to confirm ablation is complete. Electrical activity from the electrodes on the distal treatment section may be monitored. During freezing, the electrocardiograms (ECG) will present abnormal signals due to freezing of the tissue and blood in contact with the freezing tip. After freezing is completed, however, the ECGs should not show any signal or evidence of a voltage potential in the tissue due to tissue necrosis.

If, however, the ECG signals/signatures reappear after the freezing step indicating that there is still electrical activity in the tissue, this is evidence that the ablation was not complete and that PVI may not have been achieved. In the event PVI was not achieved, the above described applicable steps can be repeated.

In some embodiments, another freeze in the same location can be commenced. Or, the catheter may be repositioned or otherwise adjusted to make better contact with the target tissue. Then, an additional freeze may be performed.

Performing an additional freeze can be beneficial especially if the distance between the pulmonary veins is unusually large. When the distance between the pulmonary veins is unusually large, isolating the pulmonary vein entries with only one continuous lesion is a challenge. In a sub population of patients with unusually enlarged hearts, forming an additional lesion around the pulmonary vein entries increases the likelihood of a complete and durable PVI.

Additionally, in some situations, it may be desirable to narrow the ablation loop to accommodate a single vein. In embodiments, the method comprises performing a single vein isolation around the ostium of the single vein. The diameter of the catheter loop is reduced from the relatively large size for isolating multiple veins to the applicable size of the single vein. In embodiments, the single vein isolation is performed subsequent to the larger multiple vein isolations.

Step 1070 states to repeat the applicable steps for the pulmonary veins on the other side of the left atrium. That is, for example, after the left vein antrum is isolated, the catheter loop will be navigated to the right vein antrum and all relevant steps should be repeated to create a second, right side lesion (e.g., lesion 902 of FIG. 35).

Step 1080 states to repeat the applicable above described steps for the posterior wall lesion (lesion 903 in FIG. 35). Once both the LSPV and LIPV antrum and the RSPV and RIPV vein antrum are isolated, the looped treatment section of the catheter is navigated to the posterior wall of the left atrium.

Optionally, the EBB is inflated in the esophagus and activated prior to ablation of the posterior wall. The other applicable steps for placing the left and right lesions are repeated for the posterior lesion. The posterior lesion 903 is more centrally located, and shown in FIG. 35 overlapping the left and right antrum lesions (901 and 902, respectively). Lesion 903 is also shown extending from the floor to the ceiling of the left atrium.

Although the method describes a particular order to create the left pulmonary vein, right pulmonary vein and posterior wall lesions, embodiments of the invention are not intended to be so limited except where specifically recited in the appended claims. The order that the lesions are created may vary. For example, in embodiments, the right side or posterior lesion may be performed prior to the left side lesion.

As can be seen in FIGS. 34-35, collectively, the plurality of independent lesions (901, 902, 903) form a composite box-like shaped continuous lesion 900 (FIG. 34) that encloses all the pulmonary vein entries on all sides (left, right, top and bottom) of the left atrium. In embodiments, the sum of the sub-lesions form an enclosure in the shape of a box, square, or rectangle. Performing the ablations to form this composite, continuous lesion 900 effectively electrically isolates all the pulmonary vein entries in the left atrium.

Figure 37:
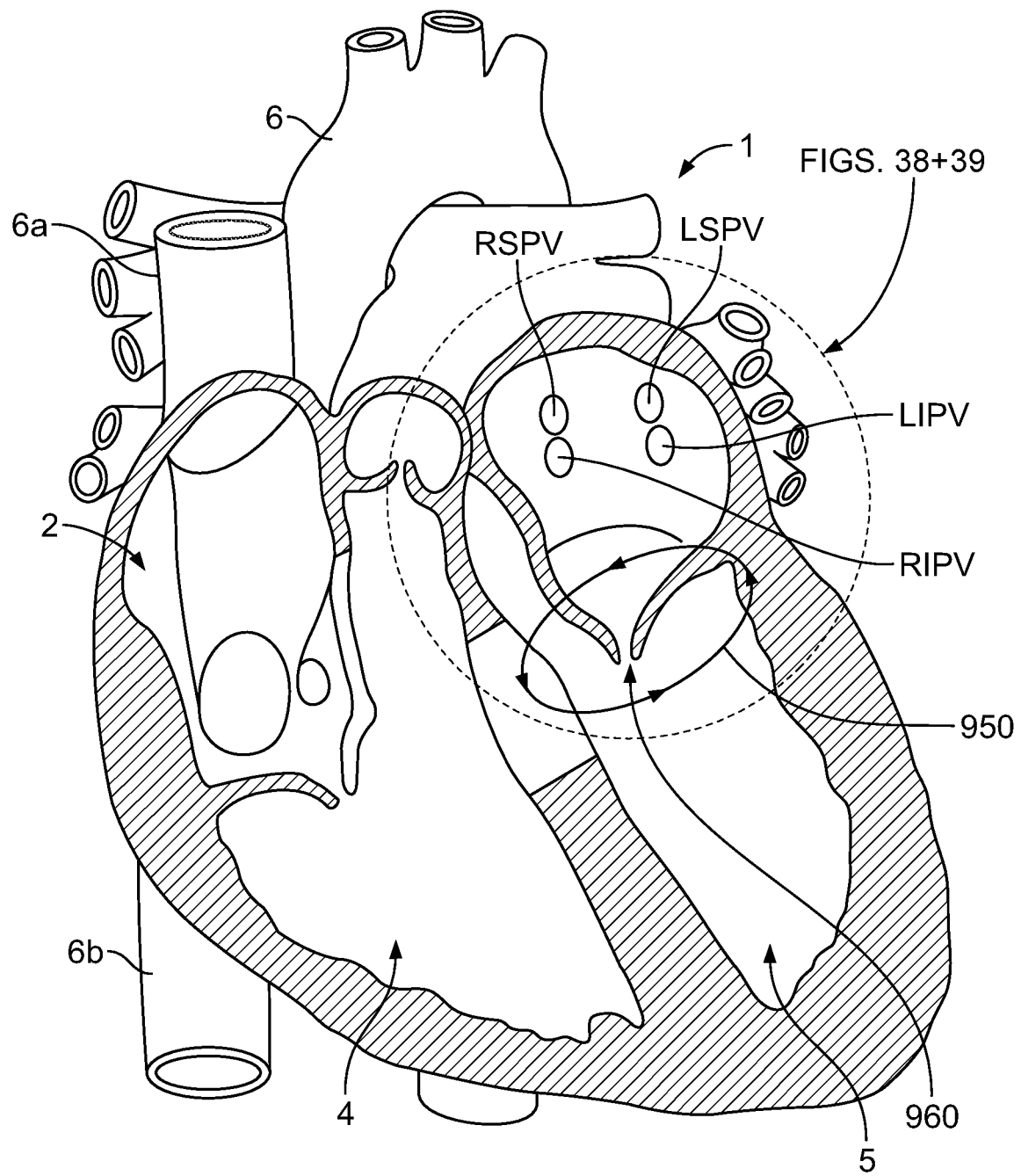
FIG. 37 is an illustration of a heart showing mitral valve electrical activity.
Figure 38:
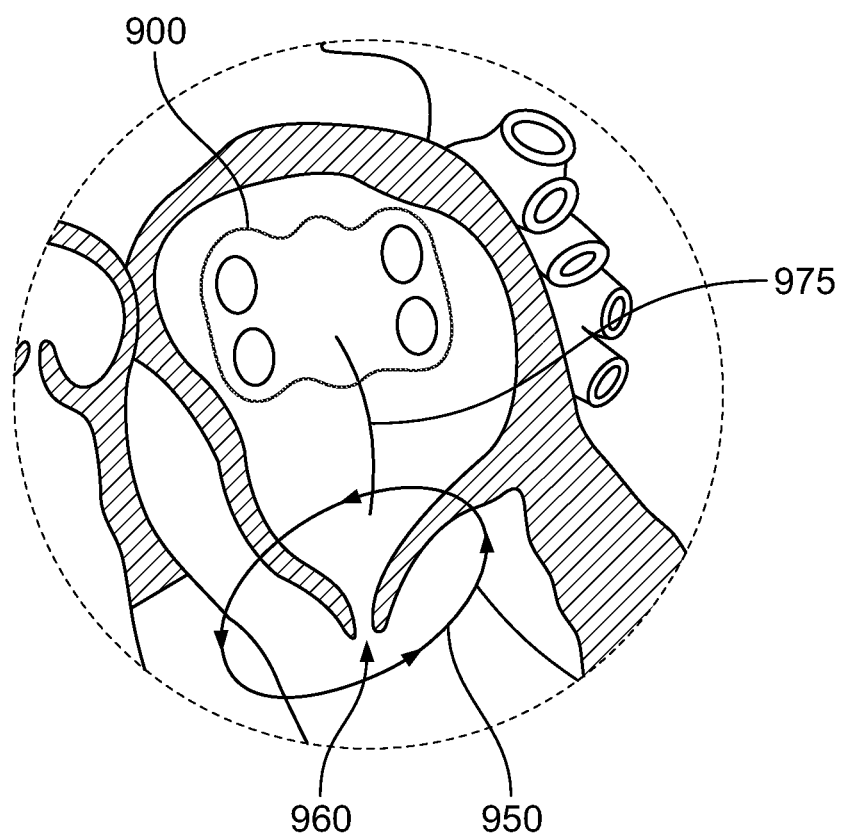
FIG. 38 depicts formation of a lesion to interrupt mitral valve electrical activity, according to an embodiment of the invention.
Figure 39:
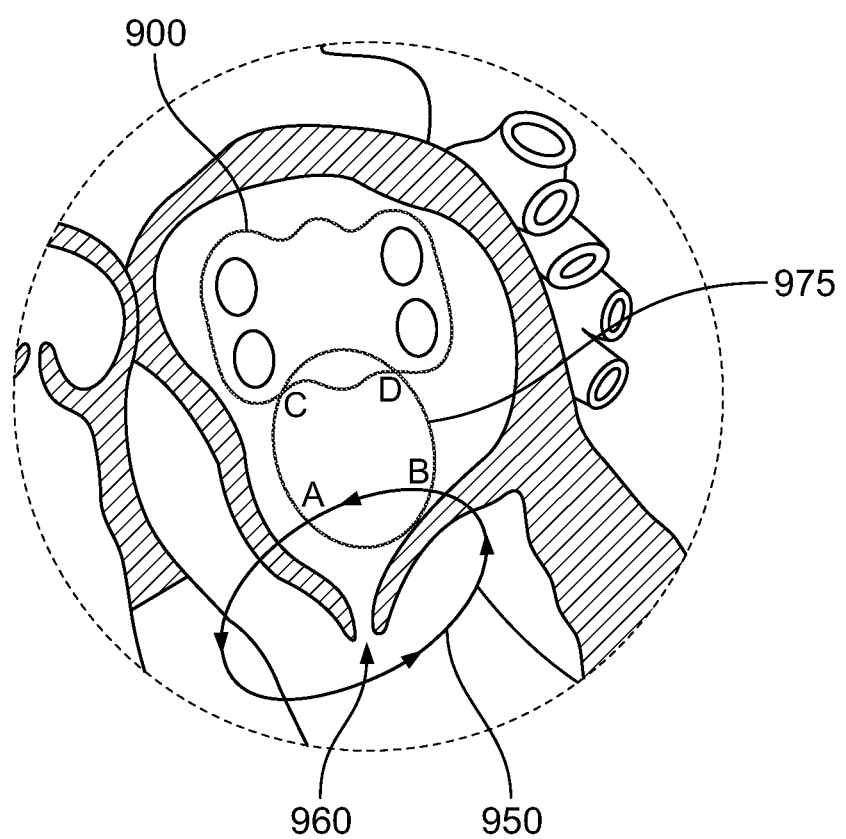
FIG. 39 depicts formation of a lesion to interrupt mitral valve electrical activity, according to an embodiment of the invention.

In patients that have atrial flutter in addition to paroxysmal atrial fibrillation and in patients that have non-paroxysmal atrial fibrillation, in addition to forming the lesions (901, 902, 903) discussed above with reference to FIGS. 34-36, it will be necessary to form an additional lesion to isolate the mitral valve. In these patients, as depicted in FIG. 37, there is electrical activity/current 950 that flows around the mitral valve 960. Therefore, the flow of this electrical activity/current 950, must be interrupted and stopped/prevented in order to treat these patients. Depicted in FIGS. 38-39 are embodiments of lesions that can be formed to interrupt the flow of current 950. As can be seen in the figures, this mitral lesion 975 connects to the box-like lesion 900 formed by the left pulmonary vein lesion 901, the right pulmonary vein lesion 902 and the posterior wall lesion 903.

As depicted in FIG. 38, in one embodiment, the mitral lesion 975 extends from the vicinity of the mitral valve 960 (the mitral valve annulus) and intersects with the flow path of the current 950 and lesion 900. In this and other embodiments, it important that the mitral lesion 975 at least intersects with the flow path of the current 950 and lesion 900. Therefore, the mitral lesion 975 can be formed at various locations within the left atrium as long as it intersects the flow path of the current 950 and connects to lesion 900. This type of lesion can be formed by modifying the shape of the treatment section of the catheter.

In the embodiment depicted in FIG. 39, the same loop-like treatment section of the catheter used to create the left pulmonary vein lesion 901, the right pulmonary vein lesion 902 and the posterior wall lesion 903 can be used to create the mitral lesion 975. As can be seen in FIG. 39, creating a loop-like or circular mitral lesion 975 cause the lesion 975 to intersect the flow path of the current 950 and lesion 900 at multiple points (A, B, C, D) thereby increasing the likelihood of a successful procedure.

Figure 40:
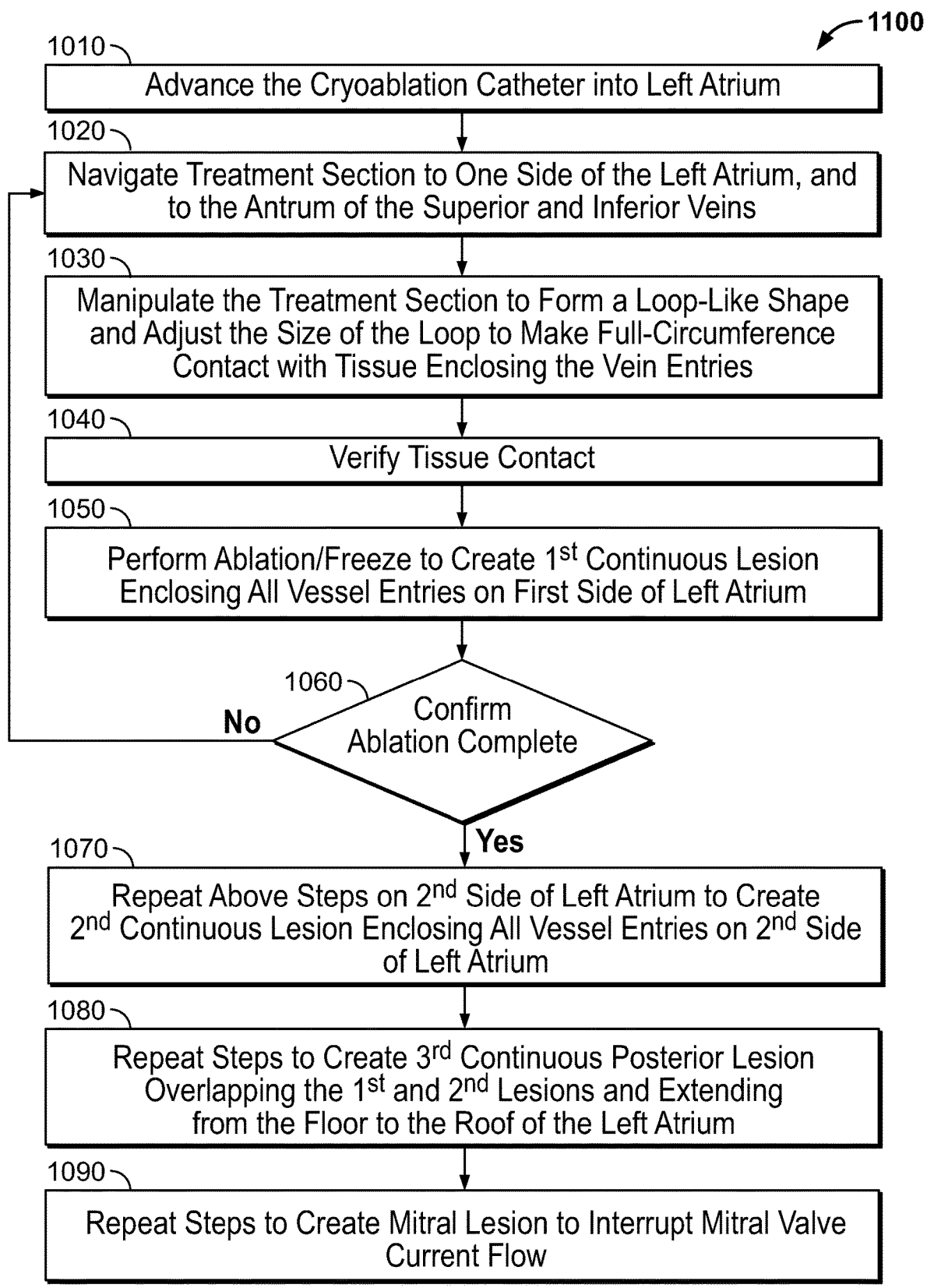
FIG. 40 is flow diagram showing a method of creating a box-shaped lesion to enclose multiple PVs in the left atrium and a lesion to interrupt mitral valve electrical activity, according to an embodiment of the invention.

If necessary, the mitral lesion 975 can be created after the box-like lesion 900 described above with respect to FIG. 36 is formed. A method 1100 for performing a procedure that includes forming the mitral lesion 975 as step 1090 after the box-like lesion 900 is formed is set forth in the flow diagram shown in FIG. 40. It will be readily apparent to those skilled in the art that the steps used in the procedure for forming the left pulmonary vein lesion 901, the right pulmonary vein lesion 902, the posterior wall lesion 903 and the mitral lesion 975 can be performed in any order as long as following the procedure, all the pulmonary vein entries are isolated and the flow path of current 950 is interrupted.

Figure 41:
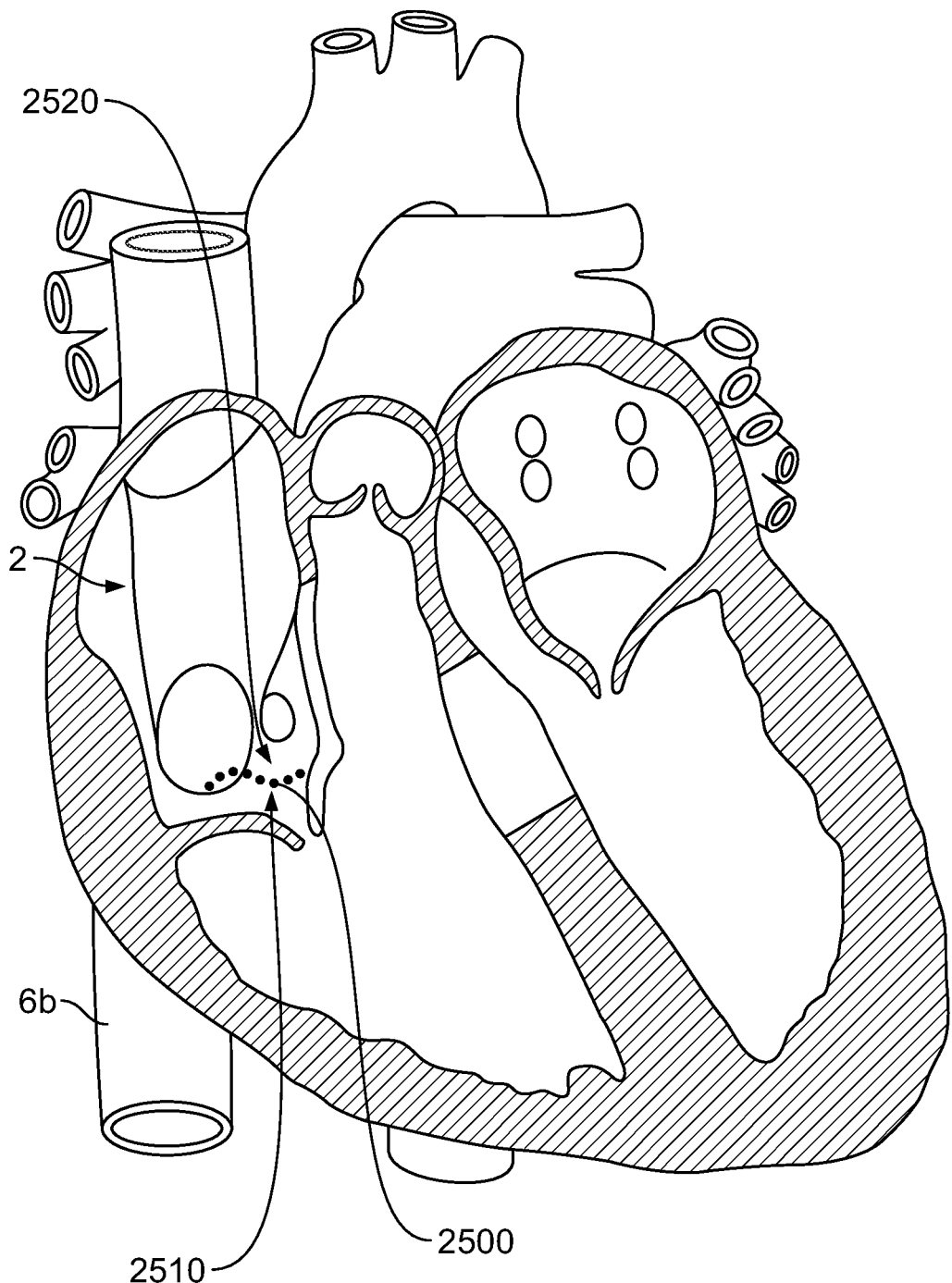
FIG. 41 depicts formation of a lesion to interrupt electrical activity in the right atrium, according to an embodiment of the invention.

In another embodiment, in some patients that suffer from persistent atrial fibrillation, a linear lesion in the right atrium 2 may be necessary. As depicted in FIG. 41, this linear lesion 2500 is created to connect the entrance of the Inferior Vena Cava (IVC) 6b and the annulus of the Tricuspid Valve (TV) 2510 and extends through the Cava Tricuspid Isthmus (CTI) 2520. This CTI lesion is used to prevent/interrupt the majority of potential re-entry circuits in the right atrium such as, for example, right atrial flutter and/or other arrhythmias that originate in the right atrium. This type of lesion is described in commonly assigned U.S. patent application Ser. No. 15/304,524, entitled "ENDOVASCULAR NEAR CRITICAL FLUID BASED CRYOABLATION CATHETER HAVING PLURALITY OF PREFORMED TREATMENT SHAPES," filed Oct. 15, 2016 by Alexei Babkin, et al., the contents of which is incorporated herein by reference in its entirety for all purposes.

In some embodiments, for certain patients, in addition to forming the lesions (901, 902, 903) discussed above with reference to FIGS. 34-36, it will be necessary to form the CTI lesion 2500 discussed above with reference to FIG. 41. It will be readily apparent to those skilled in the art that the steps used in the procedure for forming the left pulmonary vein lesion 901, the right pulmonary vein lesion 902, the posterior wall lesion 903 and the CTI lesion 2500 can be performed in any order as long as following the procedure, all the pulmonary vein entries are isolated and the majority of the potential re-entry circuits in the right atrium are interrupted/prevented.

In some embodiments, for certain patients, in addition to forming the lesions (901, 902, 903) discussed above with reference to FIGS. 34-36 and the mitral lesion 975 discussed above with reference to FIGS. 38, 39, and 40, it will be necessary to form the CTI lesion 2500 discussed above with reference to FIG. 41. It will be readily apparent to those skilled in the art that the steps used in the procedure for forming the left pulmonary vein lesion 901, the right pulmonary vein lesion 902, the posterior wall lesion 903, the mitral lesion 975 and the CTI lesion 2500 can be performed in any order as long as following the procedure, all the pulmonary vein entries are isolated, the flow path of current 950 is interrupted and the majority of the potential re-entry circuits in the right atrium are interrupted/prevented.

Treatment of Ventricular Tachycardia

In another embodiment, in some patients that suffer from ventricular tachycardia, it can be desirable to create one or more linear or focal lesions in the ventricle(s).

Figure 42:
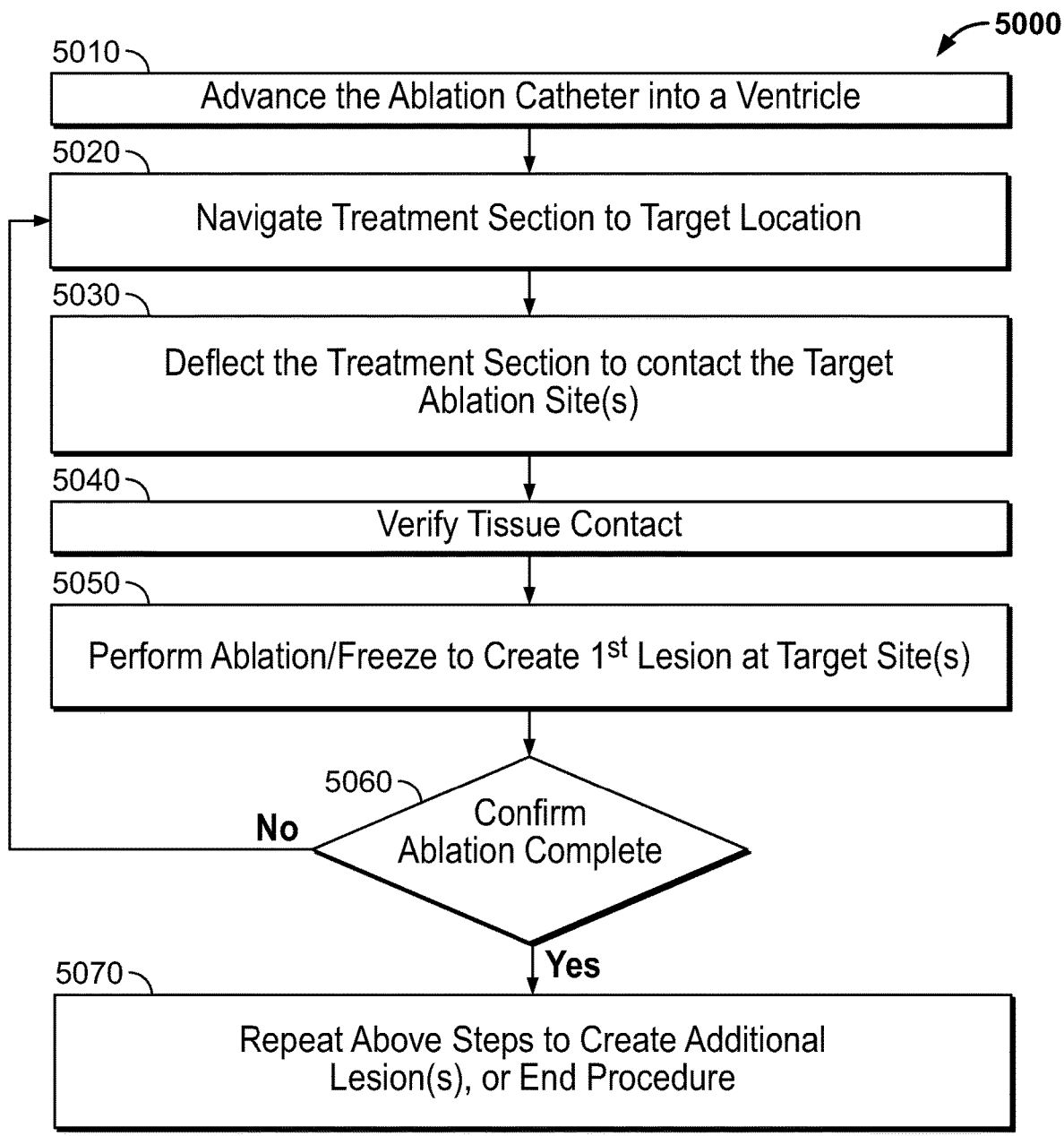
FIG. 42 is flow diagram showing a method of creating a lesion in the left or right ventricle, according to an embodiment of the invention.

With reference to FIG. 42, a method 5000 for treating VT is described in accordance with an embodiment of the invention. Initially, as described above, an ablation catheter can be introduced both via retrograde or antegrade approaches.

Step 5010 states to advance the ablation catheter into a ventricle. The catheter is inserted into the left or right ventricle.

Step 5020 states to navigate the treatment section to the target location(s). Electrodes on the catheter can be used to navigate and identify locations where ablation is desirable. Examples of desirable locations for treating VT, and with reference to FIG. 28, include the RV septum 13, LV septum 15, LV lateral wall 17, and LV apex 19.

Next, and according to step 5030, the catheter will be placed in contact with the target ablation site(s). As described herein, in embodiments, the catheter may be deflected up to 180 degrees, as well as rotated, to hit desired ablation sites for effectively treating VT.

Step 5040 states to verify tissue contact. As described herein, tissue contact can be verified with electrograms obtained from the electrodes on the treatment section of the catheter.

Step 5050 states to perform treatment. The treatment will be delivered to the targeted tissue.

Step 5060 queries whether the ablation is complete. Electrograms can be obtained from the electrodes on the distal section of the catheter, and observed for whether the ablation was effective as described herein. If the ablation is not complete, the treatment section may be further navigated or adjusted to make better contact or position as indicated by returning to step 5020 or step 5030 as the case may be.

If the ablation is complete, as verified by the electrograms or other means, the method proceeds to Step 5070 and an entire new lesion may be formed at another target location, or the procedure may be ended.

Many modifications and variations of the present invention are possible in light of the above teachings. It is therefore to be understood that within the scope of the appended claims the invention may be practiced otherwise than as specifically described.

For example, although the devices described herein can be for use as cryoablation catheters to create lesions by freezing tissue with suitable cryogen, these devices can be used in conjunction with other non-cryogen ablation energies such as, for example, radiofrequency, microwave, laser, high frequency ultrasound (HIFU), and pulse field ablation (PFA). Indeed, combinations of types of lesions may be created whether continuous and elongate or more focal in nature such as one or more points.

The invention claimed is:

1. An ablation apparatus for creating a lesion in target tissue, the ablation apparatus comprising:
   an elongate shaft comprising a proximal portion, an intermediate portion, and a distal ablation portion;
   an outer sheath extending from the proximal portion of the shaft to the distal ablation portion of the shaft;
   a first ablation fluid transport lumen extending through the shaft to the distal end for transporting a fluid in a first direction; and
   a second ablation fluid transport lumen extending through the shaft to the distal end for transporting a fluid in a second direction; and wherein the distal ablation portion comprises:
   a sleeve tip comprising a hollow cavity defined by an inner surface having a first cross sectional type shape and a closed distal end; and
   an insert disposed within said hollow cavity of said sleeve tip, said insert comprising:
      a body comprising a proximal end, an intermediate section, and a distal end,
      a hub arranged at the proximal end and defining a proximal side and a distal side;
         wherein a proximal end of the sleeve tip mates with the distal side of the hub of the insert, thereby enclosing the distal end and intermediate section of the insert, and
         wherein a distal end of the outer sheath mates with the proximal side of the hub of the insert;
      a channel extending through the body of the insert and comprising a proximal port, and a distal port, and wherein the proximal port of the channel is in fluid communication with said first ablation fluid transport lumen,
      an exterior surface defining a second cross sectional type shape different than the first cross sectional type shape;
   a plurality of discrete fluid pathways defined between the inner surface of the sleeve tip and the intermediate section of the insert, wherein the plurality of discrete fluid pathways are in fluid communication with the distal port of said channel and in fluid communication with the second ablation fluid transport lumen such that a fluid may be circulated through the plurality of discrete fluid pathways between the first and second ablation fluid transport lumens to provide ablation energy to the target tissue, thereby creating said lesion.

2. The ablation apparatus of claim 1, wherein the first cross sectional type shape is a circle and the second cross section type shape is a polygon.

3. The ablation apparatus of claim 2, wherein the polygon has a plurality of flat sides and a plurality of bowed sides.

4. The ablation apparatus of claim 3, wherein each of the plurality of fluid pathways defined between the flat sides of the insert and a curved inner surface of the sleeve tip has an effective gap in the range from 0.05 to 1 mm.

5. The ablation apparatus of claim 1, wherein the ablation portion has a length in the range from 5-25 mm.

6. The ablation apparatus of claim 1, wherein the ablation portion has an outer diameter of 1 to 5 mm.

7. The ablation apparatus of claim 1, wherein the ablation portion is rigid and straight.

8. The ablation apparatus of claim 1, wherein the sleeve tip further comprises a dome shaped distal surface, and defines a space to fluidly connect the plurality of fluid pathways and the distal port of the channel.

9. The ablation apparatus of claim 1, wherein the first and second ablation fluid transport lumens each comprise an inner tube having an outer tube surrounding the inner tube thereby defining a gap between the inner tube and the outer tube.

10. The ablation apparatus of claim 9, wherein the gap is empty or under vacuum.

11. The ablation apparatus of claim 1, further comprising a plurality of axially spaced electrodes along an exterior surface of the ablation portion.

12. The ablation apparatus of claim 11, further comprising a semi-thermally and electrically insulating material between the plurality of axially spaced electrodes.

13. The ablation apparatus of claim 1, wherein a cryogen is configured to be circulated through the plurality of discrete fluid pathways.

14. The ablation apparatus of claim 1, wherein the shaft has a shape and flexibility sufficient to be manipulated from an entry in a vessel of the patient, through the patient's vasculature, and into a chamber in the patient's heart.

15. The ablation apparatus of claim 1, further comprising a temperature sensor in the ablation portion.

16. The ablation apparatus of claim 1, further comprising
a control wire extending through the shaft from the proximal portion to the ablation portion, and operable to bend the shaft to a target angle up to 180 degrees when the control wire is manipulated from a proximal region of the control wire; and
a handle having an actuator, and said actuator is connected to the proximal region of the control wire and adapted to cause the shaft to incrementally bend an amount corresponding to the degree or amount that the actuator is adjusted.

17. The ablation apparatus of claim 16, wherein the handle further comprises a brake lock for holding the ablation portion at the target angle.

18. An ablation system comprising the ablation apparatus as recited in claim 1; a fluid source in communication with the ablation apparatus, and a controller operable to control the amount of cooling power delivered from the ablation apparatus to the tissue.

19. The ablation apparatus as recited in claim 1, wherein the shaft has a length and flexibility operable to be advanced from a peripheral vessel, through the vasculature, and to the heart.

\* \* \* \* \*